United States Patent
Wang et al.

(10) Patent No.: US 11,166,924 B2
(45) Date of Patent: Nov. 9, 2021

(54) N-METHYL-D-ASPARTATE RECEPTOR ALLOSTERIC MODULATORS AND METHODS FOR THEIR USE

(71) Applicant: Qingdao Primedicine Pharmaceutical Company, Ltd., Qingdao Shandong (CN)

(72) Inventors: Yu Tian Wang, Vancouver (CA); Peter Axerio-Cilies, Lions Bay (CA)

(73) Assignee: Qingdao Primedicine Pharmaceutical Company, Ltd., Qingdao Shandong (CN)

(*) Notice: Subject to any disclaimer, the term of this patent is extended or adjusted under 35 U.S.C. 154(b) by 0 days.

(21) Appl. No.: 16/336,418

(22) PCT Filed: Sep. 26, 2017

(86) PCT No.: PCT/CN2017/103398
§ 371 (c)(1),
(2) Date: Mar. 25, 2019

(87) PCT Pub. No.: WO2018/107853
PCT Pub. Date: Jun. 21, 2018

(65) Prior Publication Data
US 2019/0216753 A1  Jul. 18, 2019

Related U.S. Application Data

(60) Provisional application No. 62/399,654, filed on Sep. 26, 2016.

(51) Int. Cl.
| *A61K 31/165* | (2006.01) |
| *A61K 31/166* | (2006.01) |
| *A61K 31/4406* | (2006.01) |
| *A61K 31/4409* | (2006.01) |
| *A61K 31/655* | (2006.01) |
| *A61P 25/24* | (2006.01) |
| *A61P 25/28* | (2006.01) |
| *A61P 25/30* | (2006.01) |

(52) U.S. Cl.
CPC .......... *A61K 31/166* (2013.01); *A61K 31/165* (2013.01); *A61K 31/4406* (2013.01); *A61K 31/4409* (2013.01); *A61K 31/655* (2013.01); *A61P 25/24* (2018.01); *A61P 25/28* (2018.01); *A61P 25/30* (2018.01)

(58) Field of Classification Search
CPC .............. A61K 31/166; A61K 31/4406; A61K 31/4409; A61K 31/165; A61K 31/655; A61P 25/28; A61P 25/30; A61P 25/24
See application file for complete search history.

(56) References Cited

U.S. PATENT DOCUMENTS

| 8,648,198 B2 | 2/2014 | Furukawa et al. |
| 2002/0155172 A1* | 10/2002 | Yuan .................. A61K 31/00 424/692 |
| 2003/0144262 A1 | 7/2003 | Sui et al. |
| 2003/0158237 A1 | 8/2003 | Saragovi et al. |
| 2005/0043369 A1 | 2/2005 | Markham et al. |
| 2007/0037785 A1* | 2/2007 | Ansorge ............... C07C 311/08 514/183 |
| 2007/0161697 A1 | 7/2007 | Marguerie et al. |

FOREIGN PATENT DOCUMENTS

| WO | WO-02070464 A3 * | 1/2004 | .......... C07C 251/86 |
| WO | WO-2006121684 A2 * | 11/2006 | ............ A61K 31/44 |
| WO | WO 2012/027548 | 3/2012 | |

OTHER PUBLICATIONS

Taghavi et al. "N-Benzylidene-Benzohydrazides as Novel and Selective Tau-PHF Ligands" J. Alz. Dis. 2011, 27, 835-843. (Year: 2011).*
International Search Report corresponding to International Application No. PCT/CN2017/103398 dated Sep. 26, 2017.
Extended European Search Report and Opinion for EP 3 515 427 dated Sep. 11, 2020.
Gitto et al. (2011) Synthesis and Biological Characterization of 3-Substituted-1H-indoles as Ligands of GluN2B-Containing N-Methyl-d-aspartate Receptors. J. Med. Chem. 2011, 54, 24, 8702-8706.
Gitto et al. (2013) Synthesis, modelling and biological characterization of 3-substituted-1H-indoles as ligands of GluN2B-containing N-methyl-d-aspartate receptors. Bioorganic & Medicinal Chemistry 22(3):1040-1048.
International Preliminary Report on Patentability corresponding to International Application No. PCT/CN2017/103398 dated Mar. 26, 2019.
Partial Supplementary European Search Report and Opinion for EP 3 515 427 dated Apr. 17, 2020.
Semina et al. (1999) Mechanism of Action of Phosphorylacetic Acid Hydrazides as Memory Enhancers and Neuroptotectors. Phosphorus, Sulfur and Silicon and the Related Elements 144(1):753-756.
Written Opinion corresponding to International Application No. PCT/CN2017/103398 dated Jun. 27, 2018.
Colottaa et al. (1997) Glycine-NMDA Antagonists Synthesis and Biological Evaluation of a Series of Quinazoline-2-carboxylic Acids and Quinazoline-2,4-diones as Glycine-NMDA Antagonists: A Pharmacophore Model Based Approach. Archiv Der Pharmazie 330(5):129-134.

(Continued)

*Primary Examiner* — Amanda L. Aguirre
(74) *Attorney, Agent, or Firm* — Jenkins, Wilson, Taylor & Hunt, P.A.

(57) ABSTRACT

This invention relates to therapeutic compounds and compositions, and methods for their use in the prevention or treatment of neurological disorders. In particular, the invention relates to N-methyl-D-aspartate receptor (NMDAR) allosteric modulators and methods for their use in the prevention or treatment of disorders or conditions caused by or related to NMDAR dysfunctions. The invention also relates to a method for identifying NMDAR allosteric modulators.

6 Claims, 31 Drawing Sheets

Specification includes a Sequence Listing.

(56) References Cited

OTHER PUBLICATIONS

Li et al. (2004) Effect of MS-153 on the acquisition and expression of conditioned fear in rats. European Journal of Pharmacology 505(1-3):145-149.

* cited by examiner 2D chemical structure of Npam02

GluN1

PTPISYTAGFYRIPV·····SIHLSFLR
　　109　　　　　　　　　　135

GluN2A

GDDTDQEAVAQMLDF·····LVTTIFPG
　　109　　　　　　　　　　177

— GluN2A-NTD　— GluN1-NTD　— Pose-Npam43

FIGURE 13
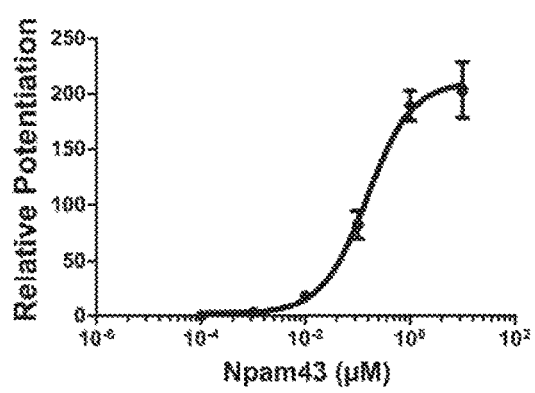
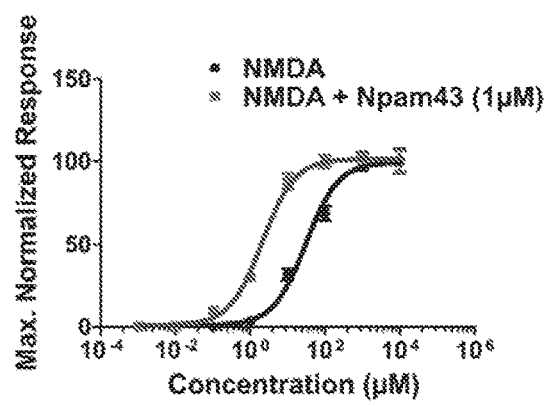

SEQUENCE LISTING

<160> NUMBER OF SEQ ID NOS: 2

<210> SEQ ID NO 1
<211> LENGTH: 938
<212> TYPE: PRT
<213> ORGANISM: Rattus norvegicus

<400> SEQUENCE: 1

```
Met Ser Thr Met His Leu Leu Thr Phe Ala Leu Leu Phe Ser Cys Ser
1               5                   10                  15

Phe Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
        35                  40                  45

Ala Asn Lys Arg His Gly Ser Trp Lys Ile Gln Leu Asn Ala Thr Ser
    50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Asn Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Arg Glu Leu Glu Ala Arg Val Ile Ile Leu Ser Ala Ser
    210                 215                 220

Glu Asp Asp Ala Ala Thr Val Tyr Arg Ala Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Ile Gly Leu Gln Leu Ile
            260                 265                 270

Asn Gly Lys Asn Glu Ser Ala His Ile Ser Asp Ala Val Gly Val Val
        275                 280                 285

Ala Gln Ala Val His Glu Leu Leu Glu Lys Glu Asn Ile Thr Asp Pro
    290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
        355                 360                 365
```

-continued

```
Gly Thr His Val Ile Pro Asn Asp Arg Lys Ile Ile Trp Pro Gly Gly
    370                 375                 380

Glu Thr Glu Lys Pro Arg Gly Tyr Gln Met Ser Thr Arg Leu Lys Ile
385                 390                 395                 400

Val Thr Ile His Gln Glu Pro Phe Val Tyr Val Lys Pro Thr Met Ser
                405                 410                 415

Asp Gly Thr Cys Lys Glu Glu Phe Thr Val Asn Gly Asp Pro Val Lys
                420                 425                 430

Lys Val Ile Cys Thr Gly Pro Asn Asp Thr Ser Pro Gly Ser Pro Arg
                435                 440                 445

His Thr Val Pro Gln Cys Cys Tyr Gly Phe Cys Ile Asp Leu Leu Ile
    450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
                485                 490                 495

Glu Trp Asn Gly Met Met Gly Glu Leu Leu Ser Gly Gln Ala Asp Met
            500                 505                 510

Ile Val Ala Pro Leu Thr Ile Asn Asn Glu Arg Ala Gln Tyr Ile Glu
                515                 520                 525

Phe Ser Lys Pro Phe Lys Tyr Gln Gly Leu Thr Ile Leu Val Lys Lys
    530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Val Ala Val Met
                565                 570                 575

Leu Tyr Leu Leu Asp Arg Phe Ser Pro Phe Gly Arg Phe Lys Val Asn
            580                 585                 590

Ser Glu Glu Glu Glu Asp Ala Leu Thr Leu Ser Ser Ala Met Trp
                595                 600                 605

Phe Ser Trp Gly Val Leu Leu Asn Ser Gly Ile Gly Glu Gly Ala Pro
    610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
            660                 665                 670

Arg Asn Pro Ser Asp Lys Phe Ile Tyr Ala Thr Val Lys Gln Ser Ser
    675                 680                 685

Val Asp Ile Tyr Phe Arg Arg Gln Val Glu Leu Ser Thr Met Tyr Arg
690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
            740                 745                 750

Phe Phe Arg Ser Gly Phe Gly Ile Gly Met Arg Lys Asp Ser Pro Trp
    755                 760                 765

Lys Gln Asn Val Ser Leu Ser Ile Leu Lys Ser His Glu Asn Gly Phe
770                 775                 780

Met Glu Asp Leu Asp Lys Thr Trp Val Arg Tyr Gln Glu Cys Asp Ser
```

```
                785                 790                 795                 800
Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
                820                 825                 830

Ile Glu Ile Ala Tyr Lys Arg His Lys Asp Ala Arg Arg Lys Gln Met
                835                 840                 845

Gln Leu Ala Phe Ala Ala Val Asn Val Trp Arg Lys Asn Leu Gln Asp
    850                 855                 860

Arg Lys Ser Gly Arg Ala Glu Pro Asp Pro Lys Lys Ala Thr Phe
865                 870                 875                 880

Arg Ala Ile Thr Ser Thr Leu Ala Ser Ser Phe Lys Arg Arg Ser
                885                 890                 895

Ser Lys Asp Thr Ser Thr Gly Gly Gly Arg Gly Ala Leu Gln Asn Gln
                900                 905                 910

Lys Asp Thr Val Leu Pro Arg Arg Ala Ile Glu Arg Glu Gly Gln
                915                 920                 925

Leu Gln Leu Cys Ser Arg His Arg Glu Ser
    930                 935

<210> SEQ ID NO 2
<211> LENGTH: 1464
<212> TYPE: PRT
<213> ORGANISM: Rattus norvegicus

<400> SEQUENCE: 2

Met Gly Arg Leu Gly Tyr Trp Thr Leu Leu Val Leu Pro Ala Leu Leu
1               5                   10                  15

Val Trp Arg Asp Pro Ala Gln Asn Ala Ala Glu Lys Gly Pro Pro
                20                  25                  30

Ala Leu Asn Ile Ala Val Leu Leu Gly His Ser His Asp Val Thr Glu
                35                  40                  45

Arg Glu Leu Arg Asn Leu Trp Gly Pro Glu Gln Ala Thr Gly Leu Pro
    50                  55                  60

Leu Asp Val Asn Val Val Ala Leu Leu Met Asn Arg Thr Asp Pro Lys
65                  70                  75                  80

Ser Leu Ile Thr His Val Cys Asp Leu Met Ser Gly Ala Arg Ile His
                85                  90                  95

Gly Leu Val Phe Gly Asp Asp Thr Asp Gln Glu Ala Val Ala Gln Met
                100                 105                 110

Leu Asp Phe Ile Ser Ser Gln Thr Phe Ile Pro Ile Leu Gly Ile His
                115                 120                 125

Gly Gly Ala Ser Met Ile Met Ala Asp Lys Asp Pro Thr Ser Thr Phe
    130                 135                 140

Phe Gln Phe Gly Ala Ser Ile Gln Gln Gln Ala Thr Val Met Leu Lys
145                 150                 155                 160

Ile Met Gln Asp Tyr Asp Trp His Val Phe Ser Leu Val Thr Thr Ile
                165                 170                 175

Phe Pro Gly Tyr Arg Asp Phe Ile Ser Phe Ile Lys Thr Thr Val Asp
                180                 185                 190

Asn Ser Phe Val Gly Trp Asp Met Gln Asn Val Ile Thr Leu Asp Thr
                195                 200                 205

Ser Phe Glu Asp Ala Lys Thr Gln Val Gln Leu Lys Lys Ile His Ser
    210                 215                 220
```

-continued

Ser Val Ile Leu Leu Tyr Cys Ser Lys Asp Glu Ala Val Leu Ile Leu
225                 230                 235                 240

Ser Glu Ala Arg Ser Leu Gly Leu Thr Gly Tyr Asp Phe Phe Trp Ile
            245                 250                 255

Val Pro Ser Leu Val Ser Gly Asn Thr Glu Leu Ile Pro Lys Glu Phe
            260                 265                 270

Pro Ser Gly Leu Ile Ser Val Ser Tyr Asp Asp Trp Asp Tyr Ser Leu
            275                 280                 285

Glu Ala Arg Val Arg Asp Gly Leu Gly Ile Leu Thr Thr Ala Ala Ser
    290                 295                 300

Ser Met Leu Glu Lys Phe Ser Tyr Ile Pro Glu Ala Lys Ala Ser Cys
305                 310                 315                 320

Tyr Gly Gln Ala Glu Lys Pro Glu Thr Pro Leu His Thr Leu His Gln
            325                 330                 335

Phe Met Val Asn Val Thr Trp Asp Gly Lys Asp Leu Ser Phe Thr Glu
            340                 345                 350

Glu Gly Tyr Gln Val His Pro Arg Leu Val Val Ile Val Leu Asn Lys
            355                 360                 365

Asp Arg Glu Trp Glu Lys Val Gly Lys Trp Glu Asn Gln Thr Leu Ser
    370                 375                 380

Leu Arg His Ala Val Trp Pro Arg Tyr Lys Ser Phe Ser Asp Cys Glu
385                 390                 395                 400

Pro Asp Asp Asn His Leu Ser Ile Val Thr Leu Glu Glu Ala Pro Phe
            405                 410                 415

Val Ile Val Glu Asp Ile Asp Pro Leu Thr Glu Thr Cys Val Arg Asn
            420                 425                 430

Thr Val Pro Cys Arg Lys Phe Val Lys Ile Asn Asn Ser Thr Asn Glu
            435                 440                 445

Gly Met Asn Val Lys Lys Cys Cys Lys Gly Phe Cys Ile Asp Ile Leu
    450                 455                 460

Lys Lys Leu Ser Arg Thr Val Lys Phe Thr Tyr Asp Leu Tyr Leu Val
465                 470                 475                 480

Thr Asn Gly Lys His Gly Lys Lys Val Asn Asn Val Trp Asn Gly Met
            485                 490                 495

Ile Gly Glu Val Val Tyr Gln Arg Ala Val Met Ala Val Gly Ser Leu
            500                 505                 510

Thr Ile Asn Glu Glu Arg Ser Glu Val Val Asp Phe Ser Val Pro Phe
    515                 520                 525

Val Glu Thr Gly Ile Ser Val Met Val Ser Arg Ser Asn Gly Thr Val
    530                 535                 540

Ser Pro Ser Ala Phe Leu Glu Pro Phe Ser Ala Ser Val Trp Val Met
545                 550                 555                 560

Met Phe Val Met Leu Leu Ile Val Ser Ala Ile Ala Val Phe Val Phe
            565                 570                 575

Glu Tyr Phe Ser Pro Val Gly Tyr Asn Arg Asn Leu Ala Lys Gly Lys
            580                 585                 590

Ala Pro His Gly Pro Ser Phe Thr Ile Gly Lys Ala Ile Trp Leu Leu
    595                 600                 605

Trp Gly Leu Val Phe Asn Asn Ser Val Pro Val Gln Asn Pro Lys Gly
    610                 615                 620

Thr Thr Ser Lys Ile Met Val Ser Val Trp Ala Phe Phe Ala Val Ile
625                 630                 635                 640

Phe Leu Ala Ser Tyr Thr Ala Asn Leu Ala Ala Phe Met Ile Gln Glu

-continued

```
                645                 650                 655
Glu Phe Val Asp Gln Val Thr Gly Leu Ser Asp Lys Lys Phe Gln Arg
                660                 665                 670
Pro His Asp Tyr Ser Pro Pro Phe Arg Phe Gly Thr Val Pro Asn Gly
                675                 680                 685
Ser Thr Glu Arg Asn Ile Arg Asn Asn Tyr Pro Tyr Met His Gln Tyr
                690                 695                 700
Met Thr Arg Phe Asn Gln Arg Gly Val Glu Asp Ala Leu Val Ser Leu
705                 710                 715                 720
Lys Thr Gly Lys Leu Asp Ala Phe Ile Tyr Asp Ala Ala Val Leu Asn
                725                 730                 735
Tyr Lys Ala Gly Arg Asp Glu Gly Cys Lys Leu Val Thr Ile Gly Ser
                740                 745                 750
Gly Tyr Ile Phe Ala Ser Thr Gly Tyr Gly Ile Ala Leu Gln Lys Gly
                755                 760                 765
Ser Pro Trp Lys Arg Gln Ile Asp Leu Ala Leu Leu Gln Phe Val Gly
                770                 775                 780
Asp Gly Glu Met Glu Glu Leu Glu Thr Leu Trp Leu Thr Gly Ile Cys
785                 790                 795                 800
His Asn Glu Lys Asn Glu Val Met Ser Ser Gln Leu Asp Ile Asp Asn
                805                 810                 815
Met Ala Gly Val Phe Tyr Met Leu Ala Ala Ala Met Ala Leu Ser Leu
                820                 825                 830
Ile Thr Phe Ile Trp Glu His Leu Phe Tyr Trp Lys Leu Arg Phe Cys
                835                 840                 845
Phe Thr Gly Val Cys Ser Asp Arg Pro Gly Leu Leu Phe Ser Ile Ser
850                 855                 860
Arg Gly Ile Tyr Ser Cys Ile His Gly Val His Ile Glu Glu Lys Lys
865                 870                 875                 880
Lys Ser Pro Asp Phe Asn Leu Thr Gly Ser Gln Ser Asn Met Leu Lys
                885                 890                 895
Leu Leu Arg Ser Ala Lys Asn Ile Ser Asn Met Ser Asn Met Asn Ser
                900                 905                 910
Ser Arg Met Asp Ser Pro Lys Arg Ala Thr Asp Phe Ile Gln Arg Gly
                915                 920                 925
Ser Leu Ile Val Asp Met Val Ser Asp Lys Gly Asn Leu Ile Tyr Ser
                930                 935                 940
Asp Asn Arg Ser Phe Gln Gly Lys Asp Ser Ile Phe Gly Asp Asn Met
945                 950                 955                 960
Asn Glu Leu Gln Thr Phe Val Ala Asn Arg His Lys Asp Asn Leu Ser
                965                 970                 975
Asn Tyr Val Phe Gln Gly Gln His Pro Leu Thr Leu Asn Glu Ser Asn
                980                 985                 990
Pro Asn Thr Val Glu Val Ala Val Ser Thr Glu Ser Lys Gly Asn Ser
                995                 1000                1005
Arg Pro Arg Gln Leu Trp Lys Lys Ser Met Glu Ser Leu Arg Gln
                1010                1015                1020
Asp Ser Leu Asn Gln Asn Pro Val Ser Gln Arg Asp Glu Lys Thr
                1025                1030                1035
Ala Glu Asn Arg Thr His Ser Leu Lys Ser Pro Arg Tyr Leu Pro
                1040                1045                1050
Glu Glu Val Ala His Ser Asp Ile Ser Glu Thr Ser Ser Arg Ala
                1055                1060                1065
```

-continued

```
Thr Cys His Arg Glu Pro Asp Asn Asn Lys Asn His Lys Thr Lys
1070                1075                1080

Asp Asn Phe Lys Arg Ser Met Ala Ser Lys Tyr Pro Lys Asp Cys
    1085                1090                1095

Ser Asp Val Asp Arg Thr Tyr Met Lys Thr Lys Ala Ser Ser Pro
1100                1105                1110

Arg Asp Lys Ile Tyr Thr Ile Asp Gly Glu Lys Glu Pro Ser Phe
    1115                1120                1125

His Leu Asp Pro Pro Gln Phe Val Glu Asn Ile Thr Leu Pro Glu
1130                1135                1140

Asn Val Gly Phe Pro Asp Thr Tyr Gln Asp His Asn Glu Asn Phe
    1145                1150                1155

Arg Lys Gly Asp Ser Thr Leu Pro Met Asn Arg Asn Pro Leu His
1160                1165                1170

Asn Glu Asp Gly Leu Pro Asn Asn Asp Gln Tyr Lys Leu Tyr Ala
    1175                1180                1185

Lys His Phe Thr Leu Lys Asp Lys Gly Ser Pro His Ser Glu Gly
1190                1195                1200

Ser Asp Arg Tyr Arg Gln Asn Ser Thr His Cys Arg Ser Cys Leu
    1205                1210                1215

Ser Asn Leu Pro Thr Tyr Ser Gly His Phe Thr Met Arg Ser Pro
1220                1225                1230

Phe Lys Cys Asp Ala Cys Leu Arg Met Gly Asn Leu Tyr Asp Ile
    1235                1240                1245

Asp Glu Asp Gln Met Leu Gln Glu Thr Gly Asn Pro Ala Thr Arg
1250                1255                1260

Glu Glu Val Tyr Gln Gln Asp Trp Ser Gln Asn Asn Ala Leu Gln
    1265                1270                1275

Phe Gln Lys Asn Lys Leu Arg Ile Asn Arg Gln His Ser Tyr Asp
1280                1285                1290

Asn Ile Leu Asp Lys Pro Arg Glu Ile Asp Leu Ser Arg Pro Ser
    1295                1300                1305

Arg Ser Ile Ser Leu Lys Asp Arg Glu Arg Leu Leu Glu Gly Asn
1310                1315                1320

Leu Tyr Gly Ser Leu Phe Ser Val Pro Ser Ser Lys Leu Leu Gly
    1325                1330                1335

Asn Lys Ser Ser Leu Phe Pro Gln Gly Leu Glu Asp Ser Lys Arg
1340                1345                1350

Ser Lys Ser Leu Leu Pro Asp His Ala Ser Asp Asn Pro Phe Leu
    1355                1360                1365

His Thr Tyr Gly Asp Asp Gln Arg Leu Val Ile Gly Arg Cys Pro
1370                1375                1380

Ser Asp Pro Tyr Lys His Ser Leu Pro Ser Gln Ala Val Asn Asp
    1385                1390                1395

Ser Tyr Leu Arg Ser Ser Leu Arg Ser Thr Ala Ser Tyr Cys Ser
1400                1405                1410

Arg Asp Ser Arg Gly His Ser Asp Val Tyr Ile Ser Glu His Val
    1415                1420                1425

Met Pro Tyr Ala Ala Asn Lys Asn Thr Met Tyr Ser Thr Pro Arg
1430                1435                1440
```

| | | | | | | | | | | | |
|---|---|---|---|---|---|---|---|---|---|---|---|
| Val | Leu | Asn | Ser | Cys | Ser | Asn | Arg | Arg | Val | Tyr | Lys | Lys | Met | Pro |
| | 1445 | | | | 1450 | | | | | 1455 | | | | |
| Ser | Ile | Glu | Ser | Asp | Val | | | | | | |
| | 1460 | | | | | | | | | | |

N-METHYL-D-ASPARTATE RECEPTOR ALLOSTERIC MODULATORS AND METHODS FOR THEIR USE

FIELD OF THE INVENTION

This invention relates to therapeutic compounds and compositions, and methods for their use in the prevention or treatment of neurological disorders. In particular, the invention relates to N-methyl-D-aspartate receptor (NMDAR) allosteric modulators and methods for their use in the prevention or treatment of disorders or conditions caused by or related to NMDAR dysfunctions. The invention also relates to a method for identifying NMDAR allosteric modulators.

BACKGROUND OF THE INVENTION

N-methyl-D-aspartate receptors (NMDARs) are a subfamily of ionotropic glutamate receptors in the brain that have critical roles in both mediating brain functions such as learning and memory (Tang, Y. P. et al. Nature (1999) 401(6748): 63-69), and in the pathogenesis of chronic brain degenerative diseases such as Alzheimer's disease (Paoletti, P. et al. Nat Rev Neurosci (2013) 14(6): 383-400), Huntington's disease (Fan, M. & Raymond, L. Prog Neurobiol (2007) 81(5-): 272-293), and Parkinson's disease (Schmidt, B. J. Ann NY Acad Sci (1998) 860: 189-202), as well as disorders including brain trauma (Shohami, E. & Biegon, A. CNS Neurol Disord Drug Targets (2014) 13(4): 567-573), and acute brain insults such as stroke (Liu, Y. et al. J Neurosci (2007) 27(11): 2846-2857).

Stroke is a leading cause of serious long-term disability (Mozaffarian, D. et al. Circulation (2015) 131(4): e29-322). Moreover, 87% of all strokes are ischemic, and are caused by blood clots formed inside the vessels that block blood flow to the brain (Haast, et al. J Cereb Blood Flow Metab (2012) 32(12): 2100-2107; Mozaffarian, D. et al. Circulation (2015) 131(4): e29-322; Zhang, Y. et al. Circulation (2008) 118(15): 1577-1584). This blockage ultimately leads to a rapid loss of brain function and slow cell death caused by lack of oxygen to the cells, programmed cell death, free radical formation and uncontrollable cell death (necrosis), all contributing to detrimental effects to the brain (Northington, F. J. et al. Ann Neurol (2011) 69(5): 743-758).

NMDAR subunits form a heterotetrameric transmembrane channel composed of combinations of the obligatory GluN1 subunit (previously known as NR1) with GluN2A-D (previously known as NR2A-D) and/or GluN3 (A & B) subunits (Collingridge, G. L. et al. Neuropharmacology (2009) 56(1): 2-5). Different GluN2 subunits (GluN2A-D) confer distinct electrophysiological and pharmacological properties on the receptor complexes and couple them with different signaling machineries (Bliss, T. & Schoepfer, R Science (2004) 304(5673): 973-974; Seeburg, P. H. Trends Neurosci (1993) 16(9): 359-365; Seeburg, P. H. Trends Pharmacol Sci (1993) 14(8): 297-303). Recent evidence suggests that NMDARs exert differential functions in mediating synaptic plasticity and cell survival depending on the presence of GluN2 subunits. In general, GluN2B-containing NMDARs activate cell death signaling, thereby mediating excitotoxic neuronal injuries, whereas GluN2A-containing NMDARs promote the induction of long-term potentiation important for learning, memory and neuronal survival, thereby protecting neurons against excitotoxic injuries.

The dual function of NMDARs in neuronal survival and death may at least in part attribute to the lack of success of NMDAR modulators in recent clinical trials. Conventional NMDAR antagonists target the surface receptor, essentially blocking both neuronal survival-signaling and death-signaling pathways, and normal functioning of the receptor, causing undesirable side effects. In contrast, enhancement of GluN2A-containing NMDARs may protect neurons against ischemic insults by specifically promoting neuronal survival mechanisms and thereby have fewer side effects and wider therapeutic window.

Current treatments options for ischemic strokes have been limited to either restoring blood flow by reperfusion after the onset of stroke through a vascular-based therapy or by blocking the signaling pathways that lead to ischemic cell death through a neuroprotection strategy (Woodruff T. M. et al. Mol Neurodegener (2011) 6(1): 11). To date, there has been no advancement in pharmacological enhancement of the function of NMDARs using a strategy of positive modulation of the receptor channel.

SUMMARY OF THE INVENTION

This invention relates to compounds that modulate NMDAR activity. Specifically, compounds identified herein, show positive modulation of the NMDAR GluN1/GluN2A and/or GluN1/GluN2B subtypes.

In one aspect of the invention, there is provided compounds of formula 1 or pharmaceutically acceptable salts thereof for use in the prevention or treatment of disorders or conditions caused by or related to NMDAR dysfunctions in a subject in need thereof,

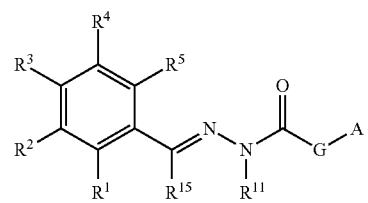

1 wherein $R^1$, $R^2$, $R^3$, $R^4$, and $R^5$ are each independently H, OH, halo, CN, $NO_2$, NRR', COOR, CONRR', $C_1$-$C_6$ alkyl, $C_2$-$C_6$ alkenyl, $C_2$-$C_6$ alkynyl, $C_1$-$C_6$ alkoxy, $C_2$-$C_6$ alkenoxy or $C_2$-$C_6$ alkynoxy;

$R^{15}$ is H or $C_1$-$C_6$ alkyl;

$R^{11}$ is H or $C_1$-$C_6$ alkyl;

G is a direct bond, O, NR, S, OCR'R", SCR'R", NRCR'R", NRC(O), NRC(O)NR', NRC(O)CR'R" or NRC(O)CR'R"O, and G is attached to the carbonyl and A in either direction;

A is A-1

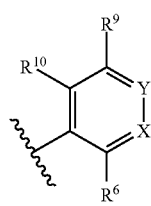

A-1;

X is $CR^7$ or N;

Y is $CR^8$ or N;

$R^6$, $R^7$, $R^8$, $R^9$, and $R^{10}$ are each independently H, OH, halo, CN, $NO_2$, NRR', $NRC(O)R^{14}$, COOR, CONRR', $C_1$-$C_6$ alkyl, $C_2$-$C_6$ alkenyl, $C_2$-$C_6$ alkynyl, $C_1$-$C_6$ alkoxy, $C_2$-$C_6$ alkenoxy or $C_2$-$C_6$ alkynoxy; or $R^7$ and $R^8$ together, or $R^8$ and $R^9$ together, can form a 5- or 6-membered saturated, partially unsaturated or aromatic monocyclic ring optionally containing 1 to 3 heteroatoms selected from the group consisting of O, N and S;

$R^{14}$ is H, $C_1$-$C_6$ alkyl, or $C_5$-$C_{10}$ aryl optionally substituted with one or more $C_1$-$C_6$ alkyl;

R, R' and R" at each occurrence are independently H or $C_1$-$C_6$ alkyl; and the alkyl, alkenyl, alkynyl, alkoxy, alkenoxy, and alkynoxy are each optionally substituted with one or more groups selected from the group consisting of OH and halo.

In a further aspect of the invention, there is provided a method for preventing or treating a disorder or condition caused by or related to NMDAR dysfunctions in a subject, comprising administering a prophylactically or therapeutically effective amount of a compound of the invention or a pharmaceutically acceptable salt thereof to the subject.

In still a further aspect of the invention, there is provided use of a compound of the invention or a pharmaceutically acceptable salt thereof in the manufacture of a medicament for the prevention or treatment of a disorder or condition caused by or related to NMDAR dysfunctions in a subject in need thereof.

In yet a further aspect of the invention, there is provided a pharmaceutical composition comprising a compound of the invention or a pharmaceutically acceptable salt thereof and a pharmaceutically acceptable carrier or adjuvant. The pharmaceutical composition can be used for modulating NMDAR activity, and thus for the prevention or treatment of disorder or conditions caused by or related to NMDAR dysfunctions in a subject in need thereof.

In yet a further aspect of the invention, there is provided a compound which specifically binds to a target site at the interface between the GluN1 and GluN2A subunits in the N-terminal domain (NTD), wherein said target site is defined at least by one or more of amino acid residue 135 of GluN1 and amino acid residues 79, 111, 115, 177 and 178 of GluN2A. In some embodiments, said compound specifically potentiates GluN1/GluN2A-containing NMDARs.

In yet a further aspect of the invention, there is provided a computer-assisted method of identifying a compound that specifically potentiates GluN1/GluN2A-containing NMDARs, the method comprising the steps of:

i) docking the structure of a candidate compound to a binding pocket between the GluN1 and GluN2A interface of NMDAR receptors in the NTD, wherein said binding pocket is defined by at least by one or more of amino acid residue 135 of GluN1 subunit and amino acid residues 79, 111, 115, 177 and 178 of GluN2A subunit, and ii) identifying a candidate compound which may specifically potentiate GluN1/GluN2A-containing NMDARs.

Said method may further comprise synthesizing or obtaining an identified candidate compound and determining if the compound specifically potentiates GluN1/GluN2A-containing NMDARs.

BRIEF DESCRIPTION OF THE DRAWINGS

FIG. 7 2D chemical structure of Npam02.

FIG. 9 Modulation effects of Npam43 in HEK293 cells expressing GluN1/GluN2A and GluN1/GluN2B NMDARs and its dose dependency curve in both expression systems.

FIG. 13 Npam43 dose-dependently potentiates NMDAR mediated currents in cultured hippocampal neurons and modulates NMDA agonist binding.

DETAILED DESCRIPTION OF THE INVENTION

Figure 1:
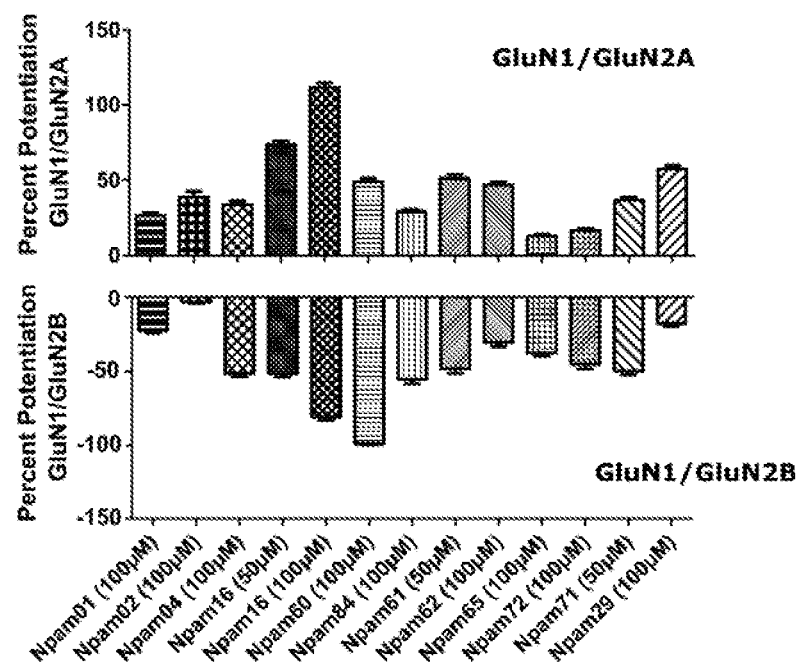
FIG. 1 Potentiation and inhibition effects of the "hit" compounds from the initial screen using whole-cell voltage clamp recordings.

Novel Modulation Binding Site on the GluN1/GluN2A NMDARs

The structural architecture of NMDARs can be characterized as having an extracellular N-terminal domain (NTD), three transmembrane domains (M1, M3, M4) with a pore channel-forming re-entrant loop (M2), a bi-lobed ligand-binding domain formed by a distal segment after the NTD (termed the S1 domain) and a large extracellular loop linking M3 and M4 (termed the S2 domain) plus the intracellular C-terminal domain (CTD) (Paoletti et al., 2013).

By 3D structural analysis and site-directed mutagenesis experiments, the present inventor identified a novel allosteric modulation binding site at the interface between GluN1 and GluN2A subunits of the NTD. Specifically, the binding pocket are formed by amino acid residues including (not limited to) GluN1 (Leu135) and GluN2A (Phe177, Pro79, Phe115, Gln11, and Pro178) in the interface between the GluN1 and GluN2A NTDs of NMDAR receptors. A modulator fits to this pocket and interacts with Leu135 of GluN1, Phe177, Pro79, Phe115, Gln111, or Pro178 of GluN2A may be capable of potentiating NMDARs, for example, specifically potentiating GluN2A-containing GluN2A.

Therefore, in one aspect of the invention, there is provided a compound which specifically binds to a target site at the interface between the GluN1 and GluN2A subunits in the N-terminal domain (NTD).

In some embodiments, the amino acid sequence of the GluN1 subunit is set forth in SEQ ID NO:1 (UniProtKB/Swiss-Prot: P35439). In some embodiments, the amino acid sequence of the GluN2A subunit is set forth in SEQ ID NO:2 (UniProtKB/Swiss-Prot: Q00959).

In some embodiments, said target site is defined at least by one or more of amino acid residue 135 of GluN1 and amino acid residues 79, 111, 115, 177 and 178 of GluN2A. In some preferred embodiments, said target site is defined at least by L135 of GluN1 and one or more of P79, Q111, F115, F177 and P178 of GluN2A. In some preferred embodiments, said target site is defined at least by L135 of GluN1 and P79, Q111, F115, F177 and P178 of GluN2A. In some embodiments, said compound interacts with one or more of amino acid residue 135 of GluN1 and amino acid residues 79, 111, 115, 177 and 178 of GluN2A. In some embodiments, said compound interacts with amino acid residues Q111 and F177 of GluN2A. In some embodiments, said compound interacts with amino acid residue L135 of GluN1 and amino acid residues P79, Q111, F115, F177 and P178 of GluN2A.

In some embodiments, said compound is an allosteric modulator of GluN1/GluN2A-containing N-methyl-D-aspartate receptor (NMDAR). In some embodiments, said modulator specifically potentiates GluN1/GluN2A-containing NMDARs.

In another aspect of the invention, there is provided a computer-assisted method of identifying a compound that specifically potentiates GluN1/GluN2A-containing NMDARs, the method comprising the steps of:
i) docking the structure of a candidate compound to a binding pocket between the GluN1 and GluN2A interface of NMDAR receptors in the NTD, wherein said binding pocket is defined by at least by one or more of amino acid residue 135 of GluN1 subunit and amino acid residues 79, 111, 115, 177 and 178 of GluN2A subunit, and
ii) identifying a candidate compound which may specifically potentiate GluN1/GluN2A-containing NMDARs.

In some preferred embodiments, said binding pocket is defined at least by L135 of GluN1 and one or more of P79, Q111, F115, F177 and P178 of GluN2A. In some preferred embodiments, said binding pocket is defined at least by L135 of GluN1 and P79, Q111, F115, F177 and P178 of GluN2A.

It is known in the art that substrates, co-factors, antagonists or agonists or allosteric modulators can be identified through the use of computer modeling using a docking program such as GRAM, DOCK, or AUTODOCK (Dunbrack et al., 1997). Computer programs can also be employed to estimate the attraction, repulsion, and steric hindrance of a candidate compound to the receptor.

In some embodiments, said method further comprises synthesizing or obtaining an identified candidate compound and determining if the compound specifically potentiates GluN1/GluN2A-containing NMDARs.

To determine whether a candidate specifically potentiates GluN1/GluN2A-containing NMDARs, methods described in the working examples of the present application can be used.

Compounds

The present invention further provides compounds of formula 1 or pharmaceutically acceptable salts thereof for use in the prevention or treatment of disorders or conditions caused by or related to NMDAR dysfunctions in a subject in need thereof,

1 wherein
$R^1$, $R^2$, $R^3$, $R^4$, and $R^5$ are each independently H, OH, halo, CN, $NO_2$, NRR', COOR, CONRR', $C_1$-$C_6$ alkyl, $C_2$-$C_6$ alkenyl, $C_2$-$C_6$ alkynyl, $C_1$-$C_6$ alkoxy, $C_2$-$C_6$ alkenoxy or $C_2$-$C_6$ alkynoxy;
$R^{15}$ is H or $C_1$-$C_6$ alkyl;
$R^{11}$ is H or $C_1$-$C_6$ alkyl;
G is a direct bond, O, NR, S, OCR'R", SCR'R", NRCR'R", NRC(O), NRC(O)NR', NRC(O)CR'R" or NRC(O)CR'R"O, and G is attached to the carbonyl and A in either direction;
A is A-1

A-1;

X is $CR^7$ or N;

Y is $CR^8$ or N;

$R^6$, $R^7$, $R^8$, $R^9$, and $R^{10}$ are each independently H, OH, halo, CN, $NO_2$, NRR', $NRC(O)R^{14}$, COOR, CONRR', $C_1$-$C_6$ alkyl, $C_2$-$C_6$ alkenyl, $C_2$-$C_6$ alkynyl, $C_1$-$C_6$ alkoxy, $C_2$-$C_6$ alkenoxy or $C_2$-$C_6$ alkynoxy; or $R^7$ and $R^8$ together, or $R^8$ and $R^9$ together, can form a 5- or 6-membered saturated, partially unsaturated or aromatic monocyclic ring optionally containing 1 to 3 heteroatoms selected from the group consisting of O, N and S;

$R^{14}$ is H, $C_1$-$C_6$ alkyl, or $C_5$-$C_{10}$ aryl optionally substituted with one or more $C_1$-$C_6$ alkyl;

R, R' and R" at each occurrence are independently H or $C_1$-$C_6$ alkyl; and the alkyl, alkenyl, alkynyl, alkoxy, alkenoxy, and alkynoxy are each optionally substituted with one or more groups selected from the group consisting of OH and halo.

In preferred embodiments, G is a direct bond, NMeC(O), $NHC(O)CH_2$, $NHCH_2$, $NHC(O)CH_2O$ or $CH_2C(O)NH$.

In preferred embodiments, X and Y are not simultaneously N.

In preferred embodiments, $R^{11}$ and $R^{15}$ are both H; $R^4$ is H, halo, $NO_2$, or $C_2$-$C_4$ alkenyl; $R^5$ is H or halo; $R^6$ is H or $C_1$-$C_4$ alkyl; and $R^{10}$ is H, OH, halo, $NH_2$, $C_1$-$C_4$ alkyl or $C_1$-$C_4$ alkoxy.

In preferred embodiments, $R^1$ is H, OH, $C_1$-$C_4$ alkoxy or $C_2$-$C_4$ alkynoxy; $R^2$ is H, OH, $C_1$-$C_4$ alkoxy or halo; and $R^3$ is H or OH; and halo represents F, Cl, Br or I, preferably Cl or Br.

In preferred embodiments, $R^7$ is H, OH, halo or $C_1$-$C_4$ alkyl; $R^8$ is H, OH, halo, $C_1$-$C_4$ alkyl, $C_1$-$C_4$ alkoxy or $NHC(O)R^{14}$ wherein $R^{14}$ is phenyl substituted with a $C_1$-$C_4$ alkyl; $R^9$ is H, OH, halo, $NO_2$ or $C_1$-$C_4$ alkyl; or $R^7$ and $R^8$ together form phenyl; or $R^8$ and $R^9$ together form 1,4-dioxanyl; and halo represents F, Cl, Br or I.

In some embodiments, the compounds of the invention have the structure of Formula I, Formula I wherein R1=H, OH, OMe, $OC_2H_2$, OEt, $NH_2$, $NEt_2$, NHEt, NHMe, COOH, $CH_2OH$, $NMe_2$, $NO_2$, $CONH_2$;

R2=H, OH, OMe, OEt, OtBu, OPr, Pr, Me, Et, NHMe, NHEt, $NEt_2$, $NMe_2$, COOH, $NO_2$, I, tBu, $CF_3$, OIsoPr, IsoPr, $CH_2OH$, CN, $CBr_3$, $CCl_3$;

R3=H, OH, $NH_2$, Me, OMe, OEt, F, Cl, Br, NHMe, NHEt, Et, $NEt_2$, $NMe_2$, COOH, $NO_2$, I, tBu, $CF_3$, $CH_2OH$, CN, $CBr_3$, $CCl_3$;

R4=H, OH, $NH_2$, OMe, OEt, F, Cl, Br, Me, $CH_2C_2H_4$, NHMe, NHEt, Et, $NEt_2$, $NMe_2$, COOH, $NO_2$, I, tBu, $CF_3$, OtBu, OisoPr, IsoPr, CN, $CH_2OH$, $CBr_3$, $CCl_3$;

R5=H, OH, $NH_2$, OMe, F, Cl, Br, Me, Et, NHMe, NHEt, $NEt_2$, $NMe_2$, COOH, $NO_2$, I, tBu, $CF_3$, CN, $CH_2OH$, $CBr_3$, $CCl_3$;

R6=H, OH, $NH_2$, F, Cl, Br, Me, OMe, Et, OEt, NHMe, NHEt, $NEt_2$, $NMe_2$, COOH, $NO_2$, I, tBu, $CF_3$, CN, $CH_2OH$, $CBr_3$, $CCl_3$;

R7=H, OH, $NH_2$, F, Cl, Br, Me, OMe, Et, OEt, NHMe, NHEt, $NEt_2$, $NMe_2$, COOH, $NO_2$, I, tBu, $CF_3$, CN, $CH_2OH$, $CBr_3$, $CCl_3$;

R8=H, OH, $NH_2$, OMe, F, Cl, Br, Me, Et, OEt, NHMe, NHEt, $NEt_2$, $NMe_2$, COOH, $NO_2$, I, tBu, $CF_3$, CN, $CH_2OH$, $CBr_3$, $CCl_3$;

R9=H, OH, $NH_2$, F, Cl, Br, Me, OMe, Et, OEt, NHMe, NHEt, $NEt_2$, $NMe_2$, COOH, $NO_2$, I, tBu, $CF_3$, CN, $CH_2OH$, $CBr_3$, $CCl_3$;

R10=H, OH, $NH_2$, F, Cl, Br, Me, OMe, Et, OEt, NHMe, NHEt, $NEt_2$, $NMe_2$, COOH, $NO_2$, I, tBu, $CF_3$, CN, $CH_2OH$, $CCl_3$, $CBr_3$;

R11=H, Me;

R12=(=O);

R15=H, Me, Et, tert-Bu.

In some embodiments, the compounds of the invention have the structure of Formula II, Formula II wherein R1=H, OH, OMe, $OC_2H_2$, OEt, $NH_2$, $NEt_2$, NHEt, NHMe, COOH, $CH_2OH$, $NMe_2$, $NO_2$, $CONH_2$;

R2=H, OH, OMe, OEt, OtBu, OPr, Pr, Me, Et, NHMe, NHEt, $NEt_2$, $NMe_2$, COOH, $NO_2$, I, tBu, $CF_3$, OIsoPr, IsoPr, $CH_2OH$, CN, $CBr_3$, $CCl_3$;

R3=H, OH, $NH_2$, Me, OMe, OEt, F, Cl, Br, NHMe, NHEt, Et, $NEt_2$, $NMe_2$, COOH, $NO_2$, 1, tBu, $CF_3$, $CH_2OH$, CN, $CBr_3$, $CCl_3$;

R4=H, OH, $NH_2$, OMe, OEt, F, Cl, Br, Me, $CH_2C_2H_4$, NHMe, NHEt, Et, $NEt_2$, $NMe_2$, COOH, $NO_2$, I, tBu, $CF_3$, OtBu, OisoPr, IsoPr, CN, $CH_2OH$, $CBr_3$, $CCl_3$;

R5=H, OH, $NH_2$, OMe, F, Cl, Br, Me, Et, NHMe, NHEt, $NEt_2$, $NMe_2$, COOH, $NO_2$, I, tBu, $CF_3$, CN, $CH_2OH$, $CBr_3$, $CCl_3$;

R11=H, Me;

R12=(=O);

R15=H, Me, Et, tert-Bu;

R14=

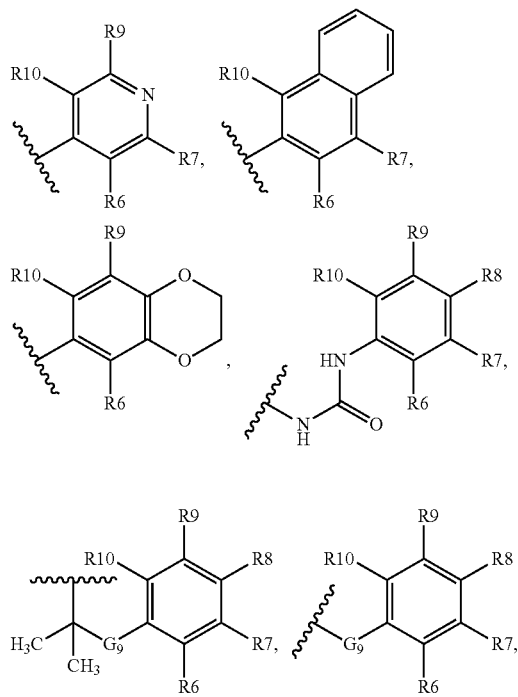

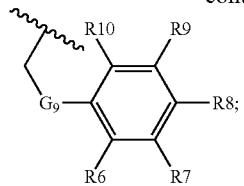

R6=H, OH, $NH_2$F, Cl, Br, Me, OMe, Et, OEt, NHMe, NHEt, $NEt_2$, $NMe_2$, COOH, $NO_2$, I, tBu, $CF_3$, CN, $CH_2OH$, $CBr_3$, $CCl_3$;

R7=H, OH, $NH_2$, F, Cl, Br, Me, OMe, Et, OEt, NHMe, NHEt, $NEt_2$, $NMe_2$, COOH, $NO_2$, I, tBu, $CF_3$, CN, $CH_2OH$, $CBr_3$, $CCl_3$;

R8=H, OH, $NH_2$, OMe, F, Cl, Br, Me, Et, OEt, NHMe, NHEt, $NEt_2$, $NMe_2$, COOH, $NO_2$, I, tBu, $CF_3$, CN, $CH_2OH$, $CBr_3$, $CCl_3$;

R9=H, OH, $NH_2$, F, Cl, Br, Me, OMe, Et, OEt, NHMe, NHEt, $NEt_2$, $NMe_2$, COOH, $NO_2$, I, tBu, $CF_3$, CN, $CH_2OH$, $CBr_3$, $CCl_3$;

R10=H, OH, $NH_2$, F, Cl, Br, Me, OMe, Et, OEt, NHMe, NHEt, $NEt_2$, $NMe_2$, COOH, $NO_2$, I, tBu, $CF_3$, CN, $CH_2OH$, $CCl_3$, $CBr_3$;

R15=H, Me, Et, tert-Bu;

G9=O, N, S.

In some embodiments, the compounds of the invention are one of more of the compounds shown in Table A or Table B:

TABLE A

Npam01
C

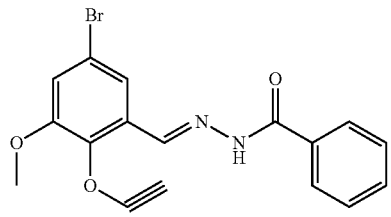 [SMILES: C#COc1c(/C=N/NC(=O)c2ccccc2)cc(Br)cc1OC]

(E)-N'-(5-bromo-2-(ethynyloxy)-3-methoxybenzylidene)benzohydrazide

Npam02
C

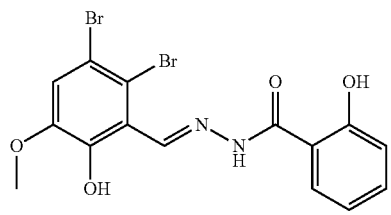 [SMILES: COc1cc(Br)c(Br)c(/C=N/NC(=O)c2ccccc2O)c1O]

(E)-N'-(2,3-dibromo-6-hydroxy-5-methoxybenzylidene)-2-hydroxybenzohydrazide

Npam03

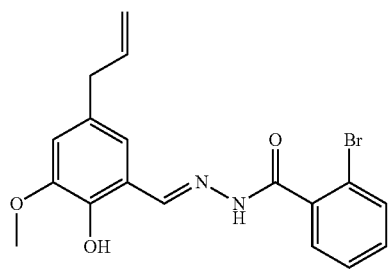 [SMILES: C=CCc1cc(/C=N/NC(=O)c2ccccc2Br)c(O)c(OC)c1]

(E)-N'-(5-allyl-2-hydroxy-3-methoxybenzylidene)-2-bromobenzohydrazide

TABLE A-continued

Npam04C

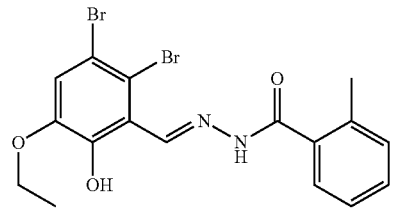 [SMILES: CCOc1cc(Br)c(Br)c(/C=N/NC(=O)c2ccccc2C)c1O]

(E)-N'-(2,3-dibromo-5-ethoxy-6-hydroxybenzylidene)-2-methylbenzohydrazide

Npam05

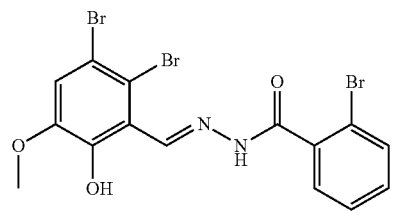 [SMILES: COc1cc(Br)c(Br)c(/C=N/NC(=O)c2ccccc2Br)c1O]

(E)-2-bromo-N'-(2,3-dibromo-6-hydroxy-5-methoxybenzylidene)benzohydrazide

Npam06

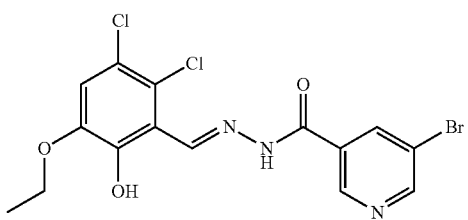 [SMILES: CCOc1cc(Cl)c(Cl)c(/C=N/NC(=O)c2cncc(Br)c2)c1O]

(E)-5-bromo-N'-(2,3-dichloro-5-ethoxy-6-hydroxybenzylidene)nicotinohydrazide

Npam07

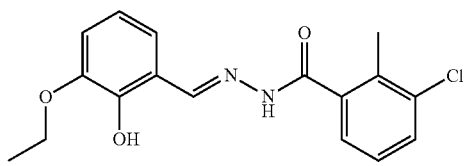 [SMILES: CCOc1cccc(/C=N/NC(=O)c2cccc(Cl)c2C)c1O]

(E)-3-chloro-N'-(3-ethoxy-2-hydroxybenzylidene)-2-methylbenzohydrazide

Npam10

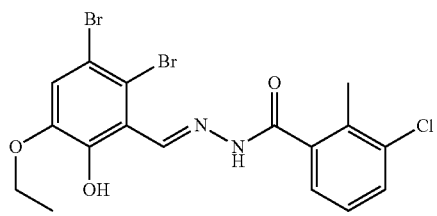 [SMILES: CCOc1cc(Br)c(Br)c(/C=N/NC(=O)c2cccc(Cl)c2C)c1O]

3-chloro-N'-[(1E)-(2,3-dibromo-5-ethoxy-6-hydroxyphenyl)methylidene]-2-methylbenzohydrazide Npam12

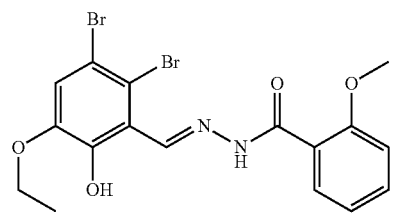 [SMILES: CCOc1cc(Br)c(Br)c(/C=N/NC(=O)c2ccccc2OC)c1O]

(E)-N'-(2,3-dibromo-5-ethoxy-6-hydroxybenzylidene)-2-methoxybenzohydrazide

TABLE A-continued

Npam15
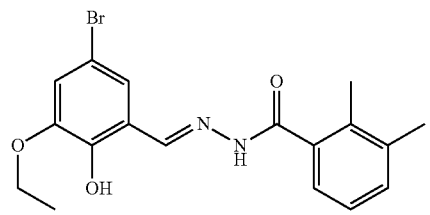 [SMILES: CCOc1cc(Br)cc(/C=N/NC(=O)c2cccc(C)c2C)c1O]
(E)-N'-(5-bromo-3-ethoxy-2-hydroxybenzylidene)-2,3-dimethylbenzohydrazide Npam17
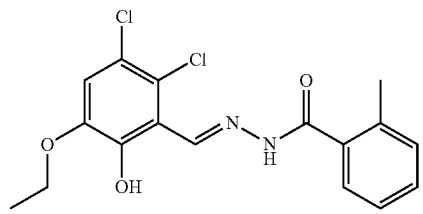
(E)-N'-(2,3-dichloro-5-ethoxy-6-hydroxybenzylidene)-2-methylbenzohydrazide Npam18
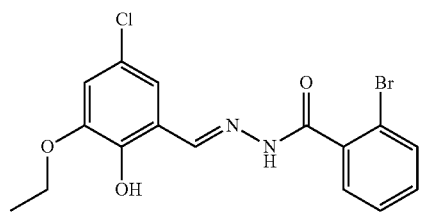 [SMILES: CCOc1cc(Cl)cc(/C=N/NC(=O)c2ccccc2Br)c1O]
(E)-2-bromo-N'-(5-chloro-3-ethoxy-2-hydroxybenzylidene)benzohydrazide Npam20
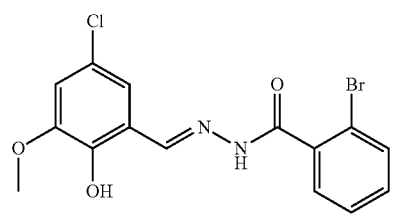 [SMILES: COc1cc(Cl)cc(/C=N/NC(=O)c2ccccc2Br)c1O]
(E)-2-bromo-N'-(5-chloro-2-hydroxy-3-methoxybenzylidene)benzohydrazide Npam28
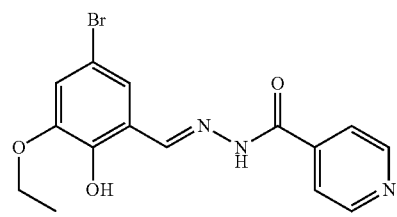 [SMILES: CCOc1cc(Br)cc(/C=N/NC(=O)c2ccncc2)c1O]
N'-[(1E)-(5-bromo-3-ethoxy-2-hydroxyphenyl)methylidene]pyridine-4-carbohydrazide Npam29
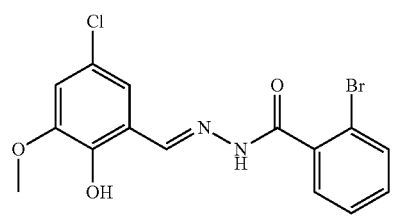 [SMILES: COc1cc(Cl)cc(/C=N/NC(=O)c2ccccc2Br)c1O]
(E)-2-bromo-N'-(5-chloro-2-hydroxy-3-methoxybenzylidene)benzohydrazide TABLE A-continued Npam31
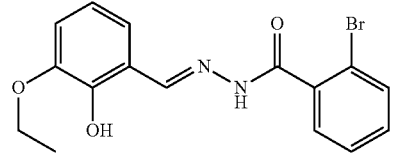 [SMILES: CCOc1cccc(/C=N/NC(=O)c2ccccc2Br)c1O]
2-bromo-N'-[(1E)-(3-ethoxy-2-hydroxyphenyl)methylidene]benzohydrazide Npam32
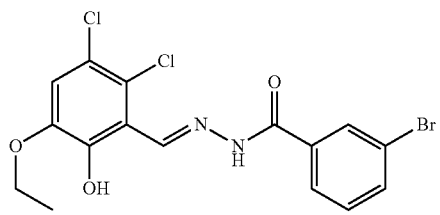
(E)-bromo-N'-(2,3-dichloro-5-ethoxy-6-hydroxybenzylidene)benzohydrazide Npam38
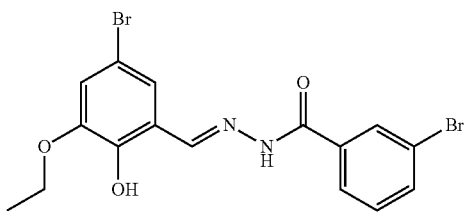 [SMILES: CCOc1cc(Br)cc(/C=N/NC(=O)c2cccc(Br)c2)c1O]
(E)-3-bromo-N'-(5-bromo-3-ethoxy-2-hydroxybenzylidene)benzohydrazide Npam43
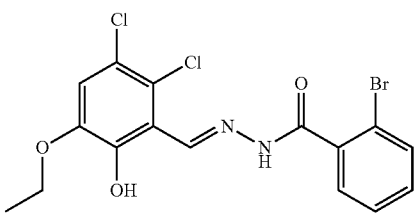 [SMILES: CCOc1cc(Cl)c(Cl)c(/C=N/NC(=O)c2ccccc2Br)c1O]
(E)-2-bromo-N'-(2,3-dichloro-5-ethoxy-6-hydroxybenzylidene)benzohydrazide Npam44
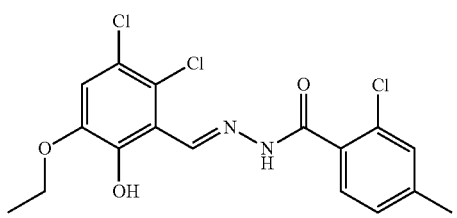 [SMILES: CCOc1cc(Cl)c(Cl)c(/C=N/NC(=O)c2ccc(C)cc2Cl)c1O]
(E)-2-chloro-N'-(2,3-dichloro-5-ethoxy-6-hydroxybenzylidene)-4-methylbenzohydrazide Npam46
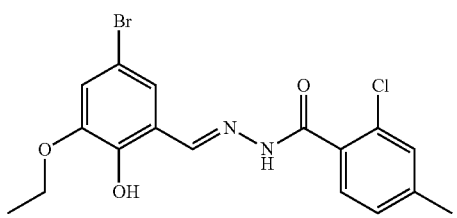 [SMILES: CCOc1cc(Br)cc(/C=N/NC(=O)c2ccc(C)cc2Cl)c1O]
(E)-N'-(5-bromo-3-ethoxy-2-hydroxybenzylidene)-2-chloro-4-methylbenzohydrazide TABLE A-continued Npam48

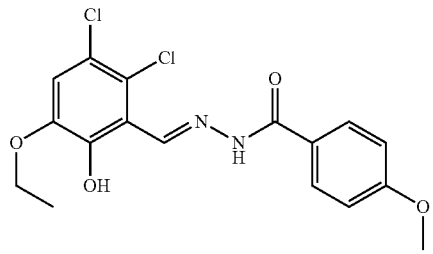 [SMILES: CCOc1cc(Cl)c(Cl)c(/C=N/NC(=O)c2ccc(OC)cc2)c1O]

(E)-N'-(2,3-dichloro-5-ethoxy-6-hydroxybenzylidene)-4-methoxybenzohydrazide

Npam49

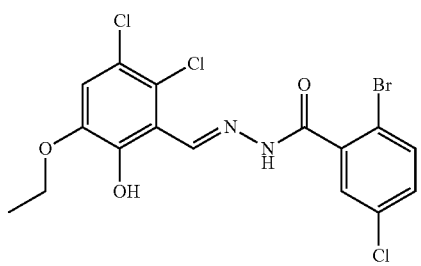 [SMILES: CCOc1cc(Cl)c(Cl)c(/C=N/NC(=O)c2cc(Cl)ccc2Br)c1O]

2-bromo-5-chloro-N'-[(1E)-(2,3-dichloro-5-ethoxy-6-hydroxyphenyl)methylidene]benzohydrazide Npam50

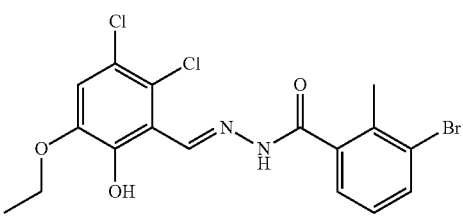 [SMILES: CCOc1cc(Cl)c(Cl)c(/C=N/NC(=O)c2cccc(Br)c2C)c1O]

3-bromo-N'-[(1E)-(2,3-dichloro-5-ethoxy-6-hydroxyphenyl)methylidene]-2-methylbenzohydrazide Npam51

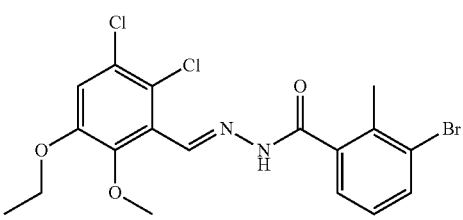 [SMILES: CCOc1cc(Cl)c(Cl)c(/C=N/NC(=O)c2cccc(Br)c2C)c1OC]

3-bromo-N'-[(1E)-(2,3-dichloro-5-ethoxy-6-methoxyphenyl)methylidene]-2-methylbenzohydrazide Npam52

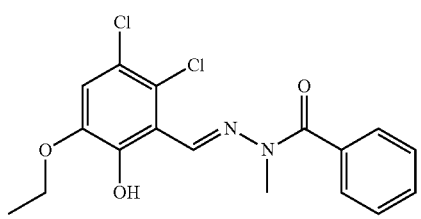 [SMILES: CCOc1cc(Cl)c(Cl)c(/C=N/N(C)C(=O)c2ccccc2)c1O]

N'-[(1E)-(2,3-dichloro-5-ethoxy-6-hydroxyphenyl)methylidene]-N-methylbenzohydrazide TABLE A-continued Npam53

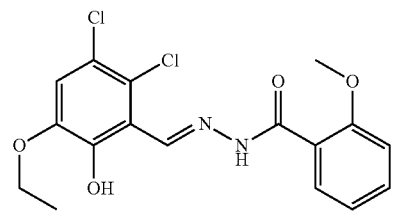 [SMILES: CCOc1cc(Cl)c(Cl)c(/C=N/NC(=O)c2ccccc2OC)c1O]

(E)-N'-(2,3-dichloro-5-ethoxy-6-hydroxybenzylidene)-2-methoxybenzohydrazide

Npam54

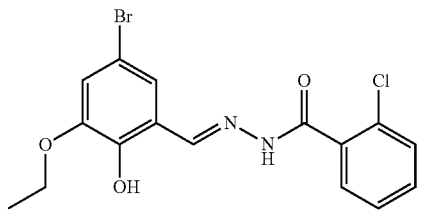 [SMILES: CCOc1cc(Br)cc(/C=N/NC(=O)c2ccccc2Cl)c1O]

N'-[(1E)-(5-bromo-3-ethoxy-2-hydroxyphenyl)methylidene]-2-chlorobenzohydrazide

Npam55

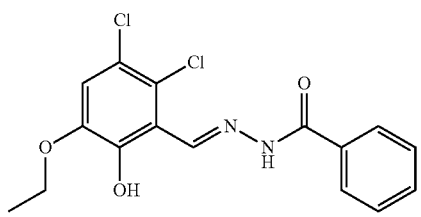 [SMILES: CCOc1cc(Cl)c(Cl)c(/C=N/NC(=O)c2ccccc2)c1O]

(E)-N'-(2,3-dichloro-5-ethoxy-6-hydroxybenzylidene)benzohydrazide

Npam56

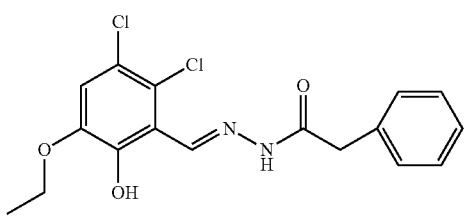 [SMILES: CCOc1cc(Cl)c(Cl)c(/C=N/NC(=O)Cc2ccccc2)c1O]

N'-[(1E)-(2,3-dichloro-5-ethoxy-6-hydroxyphenyl)methylidene]-2-phenylacetohydrazide Npam57

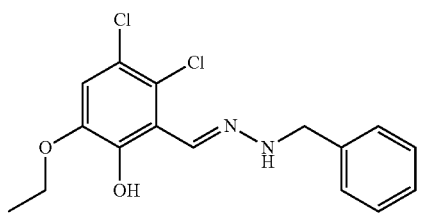 [SMILES: CCOc1cc(Cl)c(Cl)c(/C=N/NCc2ccccc2)c1O]

2-[(1E)-(2-benzylhydrazin-1-ylidene)methyl]-3,4-dichloro-6-ethoxyphenol

Npam80

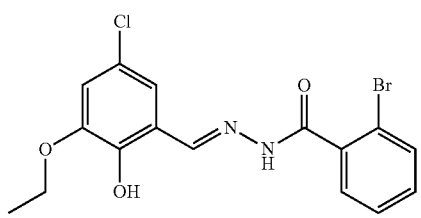 [SMILES: CCOc1cc(Cl)cc(/C=N/NC(=O)c2ccccc2Br)c1O]

(E)-2-bromo-N'-(5-chloro-3-ethoxy-2-hydroxybenzylidene)benzohydrazide

TABLE A-continued

Npam82

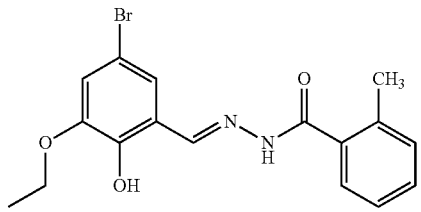 [SMILES: CCOc1cc(Br)cc(/C=N/NC(=O)c2ccccc2C)c1O]

(E)-N'-(5-bromo-3-ethoxy-2-hydroxybenzylidene)-2-methylbenzohydrazide

TABLE B

Npam01

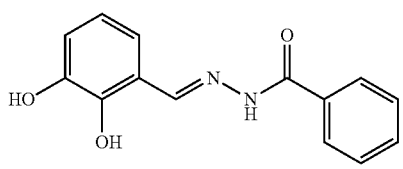 [SMILES: O=C(N/N=C/c1cccc(O)c1O)c1ccccc1]

(E)-N'-(2,3-dihydroxybenzylidene)benzohydrazide

Npam02

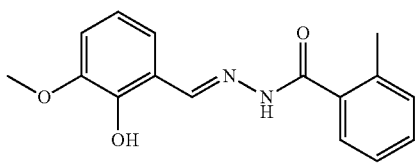 [SMILES: COc1cccc(/C=N/NC(=O)c2ccccc2C)c1O]

(E)-N'-(2-hydroxy-3-methoxybenzylidene)-2-methylbenzohydrazide

Npam04

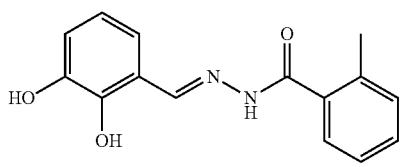 [SMILES: Cc1ccccc1C(=O)N/N=C/c1cccc(O)c1O]

(E)-N'-(2,3-dihydroxybenzylidene)-2-methylbenzohydrazide

Npam08

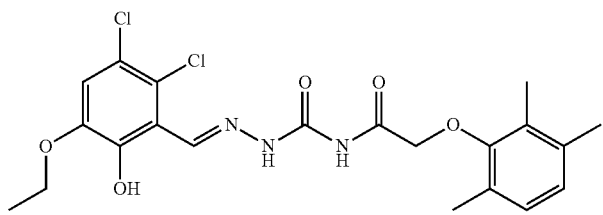 [SMILES: CCOc1cc(Cl)c(Cl)c(/C=N/NC(=O)NC(=O)COc2c(C)ccc(C)c2C)c1O]

(E)-2-(2,3-dichloro-5-ethoxy-6-hydroxybenzylidene)-N-(2-(2,3,6-trimethylphenoxy)acetyl)hydrazinecarboxamide Npam13

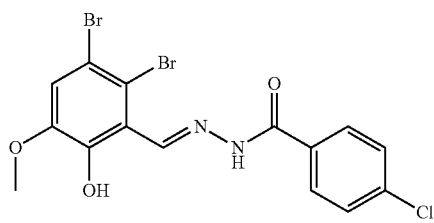 [SMILES: COc1cc(Br)c(Br)c(/C=N/NC(=O)c2ccc(Cl)cc2)c1O]

(E)-4-chloro-N'-(2,3-dibromo-6-hydroxy-5-methoxybenzylidene)benzohydrazide

TABLE B-continued

Npam16

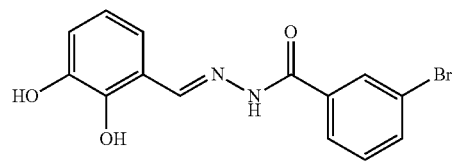 [SMILES: O=C(N/N=C/c1cccc(O)c1O)c1cccc(Br)c1]

(E)-3-bromo-N'-(2,3-dihydroxybenzylidene)benzohydrazide

Npam21

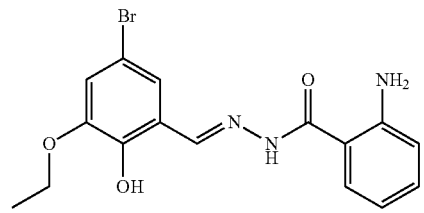

(E)-2-amino-N'-(5-bromo-3-ethoxy-2-hydroxybenzylidene)benzohydrazide

Npam22

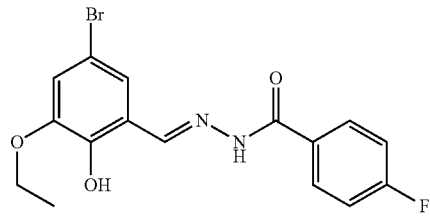 [SMILES: CCOc1cc(Br)cc(/C=N/NC(=O)c2ccc(F)cc2)c1O]

(E)-N'-(5-bromo-3-ethoxy-2-hydroxybenzylidene)-4-fluorobenzohydrazide

Npam23

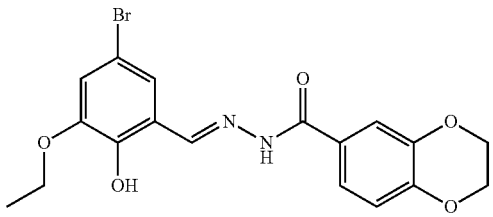 [SMILES: CCOc1cc(Br)cc(/C=N/NC(=O)c2ccc3c(c2)OCCO3)c1O]

(E)-N'-(5-bromo-3-ethoxy-2-hydroxybenzylidene)-2,3-dihydrobenzo[b][1,4]dioxine-6-carbohydrazide Npam24

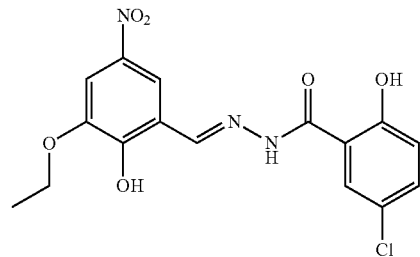 [SMILES: CCOc1cc([N+](=O)[O-])cc(/C=N/NC(=O)c2cc(Cl)ccc2O)c1O]

(E)-5-chloro-N'-(3-ethoxy-2-hydroxy-5-nitrobenzylidene)-2-hydroxybenzohydrazide

TABLE B-continued

Npam25
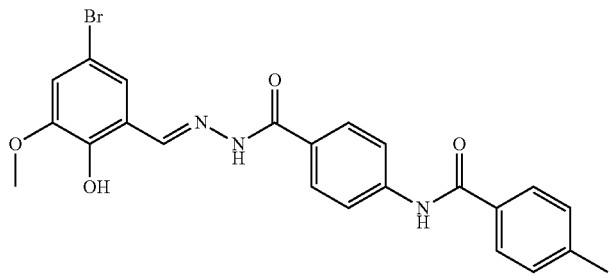 [SMILES: COc1cc(Br)cc(/C=N/NC(=O)c2ccc(NC(=O)c3ccc(C)cc3)cc2)c1O]
(E)-N-(4-(2-(5-bromo-2-hydroxy-3-methoxybenzylidene)hydrazinecarbonyl)phenyl)-
4-methylbenzamide Npam26
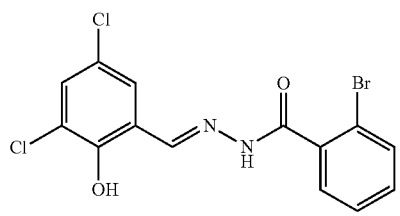 [SMILES: O=C(N/N=C/c1cc(Cl)cc(Cl)c1O)c1ccccc1Br]
(E)-2-bromo-N'-(3,5-dichloro-2-hydroxybenzylidene)benzohydrazide Npam27
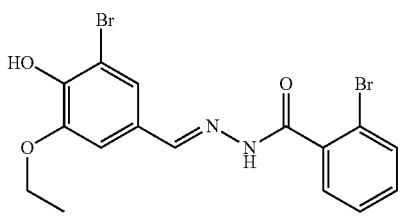 [SMILES: CCOc1cc(/C=N/NC(=O)c2ccccc2Br)cc(Br)c1O]
(E)-2-bromo-N'-(3-bromo-5-ethoxy-4-hydroxybenzylidene)benzohydrazide Npam30
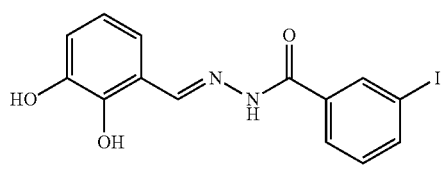 [SMILES: O=C(N/N=C/c1cccc(O)c1O)c1cccc(I)c1]
(E)-N'-(2,3-dihydroxybenzylidene)-3-iodobenzohydrazide Npam31
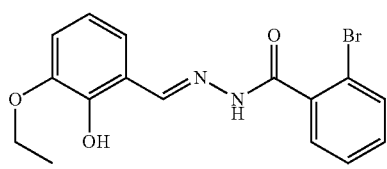 [SMILES: CCOc1cccc(/C=N/NC(=O)c2ccccc2Br)c1O]
(E)-2-bromo-N'-(3-ethoxy-2-hydroxybenzylidene)benzohydrazide Npam34
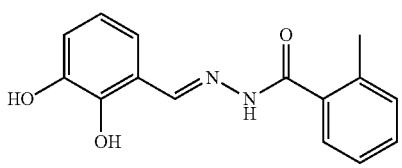 [SMILES: Cc1ccccc1C(=O)N/N=C/c1cccc(O)c1O]
(E)-N'-(2,3-dihydroxybenzylidene)-2-methylbenzohydrazide TABLE B-continued Npam35
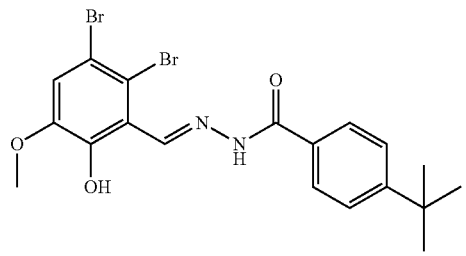 [SMILES: COc1cc(Br)c(Br)c(/C=N/NC(=O)c2ccc(C(C)(C)C)cc2)c1O]
(E)-4-(tert-butyl)-N'-(2,3-dibromo-6-hydroxy-5-methoxybenzylidene)benzohydrazide Npam36
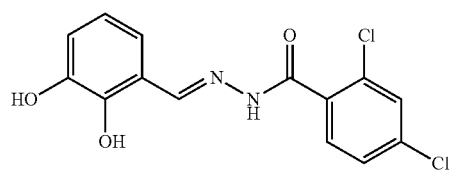 [SMILES: O=C(N/N=C/c1cccc(O)c1O)c1ccc(Cl)cc1Cl]
(E)-2,4-dichloro-N'-(2,3-dihydroxybenzylidene)benzohydrazide Npam37
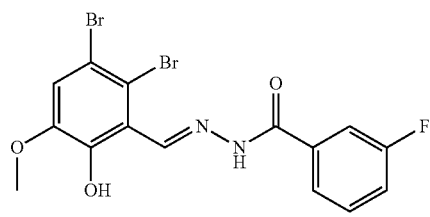 [SMILES: COc1cc(Br)c(Br)c(/C=N/NC(=O)c2cccc(F)c2)c1O]
(E)-N'-(2,3-dibromo-6-hydroxy-5-methoxybenzylidene)-3-fluorobenzohydrazide Npam39
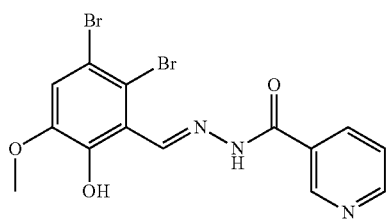 [SMILES: COc1cc(Br)c(Br)c(/C=N/NC(=O)c2cccnc2)c1O]
(E)-N'-(2,3-dibromo-6-hydroxy-5-methoxybenzylidene)nicotinohydrazide Npam40
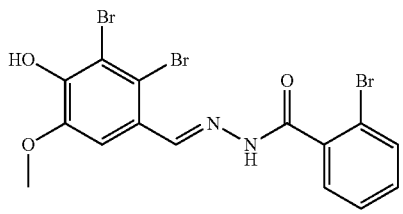 [SMILES: COc1cc(/C=N/NC(=O)c2ccccc2Br)c(Br)c(Br)c1O]
(E)-2-bromo-N'-(2,3-dibromo-4-hydroxy-5-methoxybenzylidene)benzohydrazide Npam42
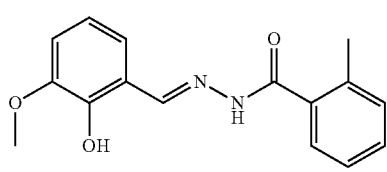 [SMILES: COc1cccc(/C=N/NC(=O)c2ccccc2C)c1O]
(E)-N'-(2-hydroxy-3-methoxybenzylidene)-2-methylbenzohydrazide TABLE B-continued Npam45

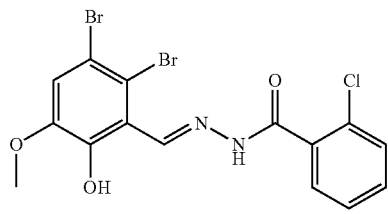

(E)-2-chloro-N'-(2,3-dibromo-6-hydroxy-5-methoxybenzylidene)benzohydrazide

Npam47

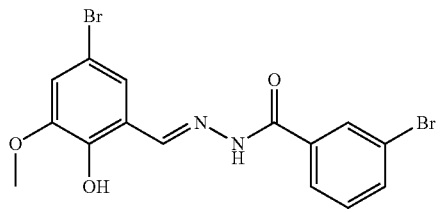 [SMILES: COc1cc(Br)cc(/C=N/NC(=O)c2cccc(Br)c2)c1O]

(E)-3-bromo-N'-(5-bromo-2-hydroxy-3-methoxybenzylidene)benzohydrazide

Npam58

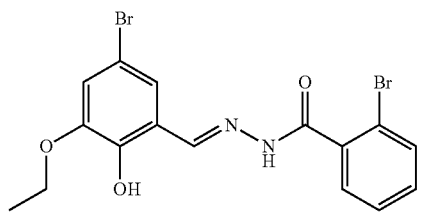

(E)-2-bromo-N'-(5-bromo-3-ethoxy-2-hydroxybenzylidene)benzohydrazide

Npam59

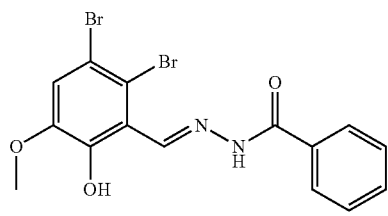 [SMILES: COc1cc(Br)c(Br)c(/C=N/NC(=O)c2ccccc2)c1O]

(E)-N'-(2,3-dibromo-6-hydroxy-5-methoxybenzylidene)benzohydrazide

Npam64

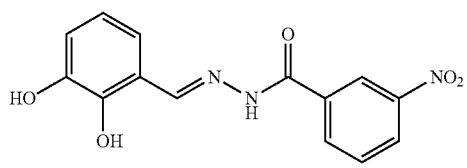 [SMILES: O=C(N/N=C/c1cccc(O)c1O)c1cccc([N+](=O)[O-])c1]

(E)-N'-(2,3-dihydroxybenzylidene)-3-nitrobenzohydrazide

Npam65

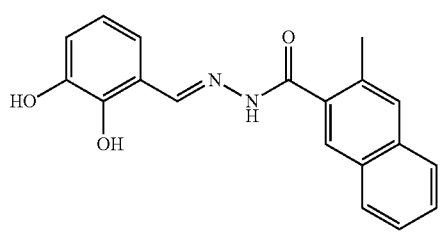 [SMILES: Cc1cc2ccccc2cc1C(=O)N/N=C/c1cccc(O)c1O]

(E)-N'-(2,3-dihydroxybenzylidene)-3-methyl-2-naphthohydrazide

TABLE B-continued

Npam66
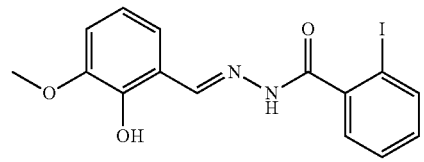 [SMILES: COc1cccc(/C=N/NC(=O)c2ccccc2I)c1O]
(E)-N'-(2-hydroxy-3-methoxybenzylidene)-2-iodobenzohydrazide

Npam68
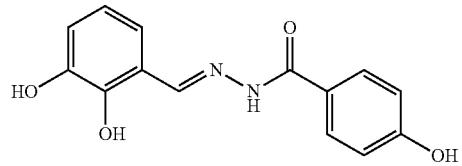 [SMILES: O=C(N/N=C/c1cccc(O)c1O)c1ccc(O)cc1]
(E)-N'-(2,3-dihydroxybenzylidene)-4-hydroxybenzohydrazide

Npam69
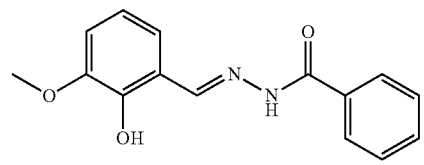 [SMILES: COc1cccc(/C=N/NC(=O)c2ccccc2)c1O]
(E)-N'-(2-hydroxy-3-methoxybenzylidene)benzohydrazide

Npam70
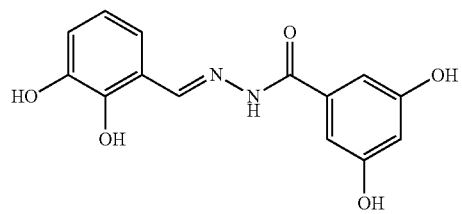 [SMILES: O=C(N/N=C/c1cccc(O)c1O)c1cc(O)cc(O)c1]
(E)-N'-(2,3-dihydroxybenzylidene)-3,5-dihydroxybenzohydrazide Npam71
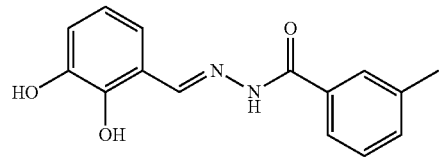 [SMILES: Cc1cccc(C(=O)N/N=C/c2cccc(O)c2O)c1]
(E)-N'-(2,3-dihydroxybenzylidene)-3-methylbenzohydrazide Npam72
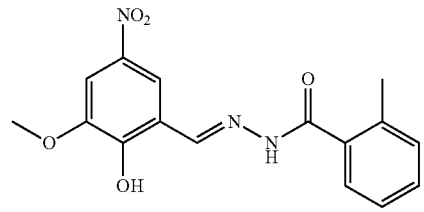 [SMILES: COc1cc([N+](=O)[O-])cc(/C=N/NC(=O)c2ccccc2C)c1O]
(E)-N'-(2-hydroxy-3-methoxy-5-nitrobenzylidene)-2-methylbenzohydrazide Npam73
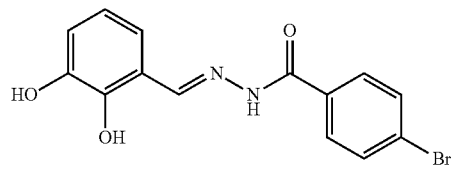 [SMILES: O=C(N/N=C/c1cccc(O)c1O)c1ccc(Br)cc1]
(E)-4-bromo-N'-(2,3-dihydroxybenzylidene)benzohydrazide TABLE B-continued Npam75

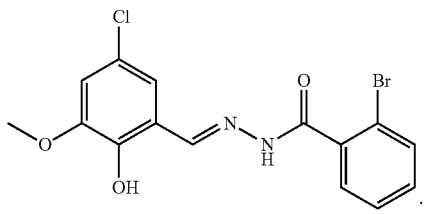 [SMILES: COc1cc(Cl)cc(/C=N/NC(=O)c2ccccc2Br)c1O]

(E)-2-bromo-N'-(5-chloro-2-hydroxy-3-methoxybenzylidene)benzohydrazide

The compounds of the invention are NMDAR allosteric modulators, and preferably, are selective GluN2A-containing NMDAR positive modulators and/or selective GluN2B-containing NMDAR positive modulators.

As used herein the following definitions are applicable.

The term "alkyl" refers to both branched and straight-chain saturated aliphatic hydrocarbon groups having the specified number of carbon atoms. Unless otherwise specified, "alkyl" refers to $C_1$-$C_6$ alkyl. For example, "$C_1$-$C_6$ alkyl" is defined to include groups having 1, 2, 3, 4, 5 or 6 carbons in a linear or branched arrangement. For example, "$C_1$-$C_6$ alkyl" includes but is not limited to methyl, ethyl, n-propyl, i-propyl, n-butyl, t-butyl, i-butyl, pentyl, and hexyl.

The term "alkenyl" refers to both branched and straight-chain hydrocarbon groups having the specified number of carbon atoms and at least one carbon-carbon double bond. In some embodiments, one carbon-carbon double bond is present, and up to three carbon-carbon double bonds may be present. Thus, "$C_2$-$C_6$ alkenyl" means an alkenyl radical having 2, 3, 4, 5 or 6 carbon atoms and 1, 2 or 3 carbon-carbon double bonds. For example, "$C_2$-$C_6$ alkenyl" includes but is not limited to ethenyl, propenyl, butenyl and 2-methylbutenyl.

The term "alkynyl" refers to both branched and straight-chain hydrocarbon groups having the specified number of carbon atoms and at least one carbon-carbon triple bond. In some embodiments, one carbon-carbon triple bond is present, and up to three carbon-carbon triple bonds may be present. Thus, "$C_2$-$C_6$ alkynyl" means an alkynyl radical having 2, 3, 4, 5 or 6 carbon atoms and 1, 2 or 3 carbon-carbon triple bonds. For example, "$C_2$-$C_6$ alkynyl" includes but is not limited to ethynyl, propynyl, butynyl, and 3-methylbutynyl.

The terms "alkoxyl", "alkenoxy" and "alkynoxy" respectively refer to an alkyl radical, an alkenyl radical and an alkynl radical defined above but attached through an oxygen bridge at any of the available carbon atoms. Thus, for example, "$C_1$-$C_6$ alkoxy" means an alkyl radical having 1, 2, 3, 4, 5 or 6 carbon atoms and attached through an oxygen bridge, and includes but is not limited to methoxy, ethoxy, n-propoxy, i-propoxy, n-butoxy, t-butoxy, i-butoxy, pentoxy, and hexoxy.

It will be understood by a person of skill that COOH and NRR' in the compounds of the invention may be present in the form of the corresponding ions, for example carboxylate ions and ammonium ions, respectively. Alternatively, where the ions are shown, a person of skill in the art will appreciate that the counter ion may also be present.

Those skilled in the art will appreciate that the point of covalent attachment of the moiety to the compounds as described herein may be, for example, and without limitation, cleaved under specified conditions. Specified conditions may include, for example, and without limitation, in vivo enzymatic or non-enzymatic means. Cleavage of the moiety may occur, for example, and without limitation, spontaneously, or it may be catalyzed, induced by another agent, or a change in a physical parameter or environmental parameter, for example, an enzyme, light, acid, temperature or pH. The moiety may be, for example, and without limitation, a protecting group that acts to mask a functional group, a group that acts as a substrate for one or more active or passive transport mechanisms, or a group that acts to impart or enhance a property of the compound, for example, solubility, bioavailability or localization.

Compounds as described herein may be in the free form or in the form of a salt thereof. In some embodiments, compounds as described herein may be in the form of a pharmaceutically acceptable salt, which are known in the art (Berge S. M. et al., J Pharm Sci (1977) 66(1):1-19).

Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt.

Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid.

Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N-dibenzylethylenediamine or polyamine resins.

In some embodiments, compounds as described herein may contain both acidic and basic groups and may be in the form of inner salts or zwitterions, for example, and without limitation, betaines.

Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) may be in the solvent addition form, for example, solvates. Solvates contain either stoichiometric or non-stoichiometric amounts of a solvent in physical association with the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

Pharmaceutical Compositions and Preparations

The present invention provides a pharmaceutical composition comprising a compound or a pharmaceutically acceptable salt thereof as set out herein and a pharmaceutically acceptable carrier or excipient. The pharmaceutical composition is useful for modulating NMDAR activity, for example, specifically potentiating NMDARs such as GluN2A-containing NMDARs.

The pharmaceutical composition of the invention can be provided in the form of a commercial package, which comprises instructions for the use of the composition for modulating NMDAR activity.

Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents (used interchangeably herein) are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one skilled in the art are described in Remington: the Science & Practice of Pharmacy by Alfonso Gennaro, 20th ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene polyoxypropylene copolymers may be used to control the release of the compounds. Other potentially useful parenteral delivery systems for modulatory compounds include ethylene vinyl acetate copolymer particles, osmotic pumps, implantable infusion systems, and liposomes. Formulations for inhalation may contain excipients, for example, lactose, or may be aqueous solutions containing, for example, polyoxyethylene 9 lauryl ether, glycocholate and deoxycholate, or may be oily solutions for administration in the form of nasal drops, or as a gel.

Compounds or pharmaceutical compositions as described herein or for use as described herein may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

An "effective amount" of a pharmaceutical composition as described herein includes a therapeutically effective amount. A "therapeutically effective amount" refers to an amount effective, at dosages and for periods of time necessary, to achieve the desired therapeutic result, such as reduced infarct size, reduced neuronal damage, improved behavioral performance, increased life span or increased life expectancy. A therapeutically effective amount of a compound may vary according to factors such as the brain insult or disease state, age, sex, and weight of the subject, and the ability of the compound to elicit a desired response in the subject.

Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, reduced infarct size, reduced neuronal damage, improved behavioral performance, increased life span or increased life expectancy. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In some embodiments, compounds and all different forms thereof as described herein may be used, for example, and without limitation, in combination with other treatment methods for at least one indication selected from the group consisting of: Alzheimer's disease, Huntington's disease, Parkinson's disease, brain trauma, and acute brain insults such as stroke. For example, compounds and all their different forms as described herein may be used as neoadjuvant (prior), adjunctive (during), and/or adjuvant (after) therapy with tissue plasminogen activator (TPA) or other therapies.

Medical Uses

The present invention provides a method for modulating NMDAR activity, for example, specifically potentiating NMDARs such as GluN2A-containing NMDARs, the method comprising administering to a mammalian cell, a compound or pharmaceutically acceptable salt thereof as set out herein, or a pharmaceutical composition as set out herein.

Alternatively, the present invention provides a method for modulating NMDAR activity, for example, specifically potentiating NMDARs such as GluN2A-containing NMDARs, the method comprising administering to a subject in need thereof, a compound or pharmaceutically acceptable salt thereof as set out herein, or a pharmaceutical composition as set out herein.

By modulating NMDAR activity, the compounds and compositions of the invention may be used for the prevention or treatment of a disorder or condition caused by or related to NMDAR dysfunctions. In particular, the disorder or condition can be at least one selected from the group consisting of: impairments in learning and memory, migraine, epilepsy, Alzheimer's disease, Huntington's disease, Parkinson's disease, brain trauma, acute brain insults such as stroke, schizophrenia, neuropathic pain, depression, and drug addiction. For example, the disorder or condition is stroke, especially ischemic stroke. The compounds and compositions of the invention may also be used for improving learning, cognition or memory.

The mammalian cell may be a human cell. The cell may be a neuron.

The subject may be suspected of having or at risk of having a neuropathological condition or neurodegenerative disease. The neuropathological condition may be an acute brain insult including stroke or a traumatic brain injury. The neurodegenerative disease may be Alzheimer's Disease, Parkinson's Disease or Huntington's Disease or mental illnesses such as schizophrenia, anxiety and depression.

In general, compounds as described herein should be used without causing substantial toxicity. Toxicity of the compounds as described herein can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be appropriate to administer substantial excesses of the compositions. Some compounds as described herein may be toxic at some concentrations. Titration studies may be used to determine toxic and non-toxic concentrations. Toxicity may be evaluated by examining a particular compound's or composition's specificity across cell lines. Animal studies may be used to provide an indication if the compound has any effects on other tissues.

Compounds as described herein may be administered to a subject. As used herein, a "subject" may be a human, non-human primate, rat, mouse, cow, horse, pig, sheep, goat, dog, cat, etc. The subject may be suspected of having or at risk for having a neurodegenerative disease such as Alzheimer's Disease, Parkinson's Disease, Huntington's Disease or mental illnesses, or a neuropathological condition such as traumatic brain injury or acute brain insults such as stroke. Diagnostic methods for various neuropathological and neurodegenerative conditions such as Alzheimer's Disease, Parkinson's Disease, Huntington's Disease, mental illnesses, traumatic brain injuries or acute brain insults such as stroke are known to those of ordinary skill in the art.

Various alternative embodiments and examples of the invention are described herein. These embodiments and examples are illustrative and should not be construed as limiting the scope of the invention.

EXAMPLES

General Methods and Materials

1. In Silico Pipeline 1.1 Selection of Compounds from the ZINC Library

A subset of lead-like compounds was filtered from the ZINC library based on various molecular descriptors. The lead-like subset was then further filtered using Lupinski's rule of three for developing CNS compounds (Pajouhesh & Lenz, 2005) plus additional chemical properties including, no carboxylic groups, no peptide bond-like structures, polar surface area between 60-80 A2 and possession of at least 1 nitrogen, 1 oxygen and 1 aromatic ring. All candidate compounds were filtered based on whether they incorporated chemical motifs or known toxicophores. The resulting database was finalized by adding hydrogens along with removal of minor components (salts), de-pronating strong acids and protonating strong bases. Finally, the filtered database was energy minimized to attain the three-dimensional structures of the compounds at their lowest energy state. The finalized optimized structures were then ready for docking against the interstice interface of the GluN1/GluN2A heterodimer N-terminal domain (NTD).

1.2 Homology Model.

A homology model was created based on the crystal structure of the GluN1/GluN2B. The homology model of the rat NMDAR N-terminal extracellular domain of the NR1/NR2A receptor was constructed using the X-ray structure of the analogous GluN1/GluN2B N-terminal domain (PDB code: 3QEK). Even though the GluN1/GluN2A receptor is a tetrameric receptor, the homology model was done on one dimer consisting of 1 subunit of GluN1 and 1 subunit of GluN2A. The NTDs of GluN2A and GluN2B show 72% sequence identity and 82% homology in the sequence alignment.

1.3 Virtual Screening (Docking) for Selective Modulators for GluN1/GluN2A-Containing NMDARs Using a previously described consensus-based in silico methodology, (Axerio-Cilies et al., 2011; Lack et al., 2011) the inventors conducted a virtual screen of 200,000 purchasable chemical substances pre-filtered (Axerio-Cilies et al., 2009; Pajouhesh & Lenz, 2005) from the lead-like ZINC chemical library (Irwin & Shoichet, 2005) to identify specific binders that may be capable of positive allosteric modulation (PAM) of GluN1/GluN2A-containing NMDARs. The results from each stage of this multiparametric approach were compiled, and the compounds were ranked using a consensus scoring procedure. The ~10,000 highest ranked compounds were visualized, and 200 initial candidates, predicted to have a high potential for binding to the GluN1/GluN2A interface, were selected for empirical testing.

1.4 Analog Search

An analog search was conducted to obtain a large pool of chemicals from which to generate structure-activity-relationships (SAR). The active compound (Npam02) was used as a template/query to search against a database of chemicals using molecular fingerprint-based similarity searching. If a feature is present in a molecule the bit is set to '1' and if the feature is not present, the bit is set to '0' forming a distinctive and unique fingerprint profile for each chemical structure. The similarity between two molecules is identified by comparing bit strings of molecules and quantified as Tanimoto coefficient (Tc) (Bajusz, Racz, & Heberger, 2015). The compounds generated in the search were combined with the chemically synthesized compounds designed in silico to generate a list of compounds that could be tested by whole-cell voltage clamp recordings in cortical neurons to generate SARs.

1.5 Chemical Synthesis of Npam Compounds

Chemical synthesis of the Npam compounds was carried out by reacting an appropriate substituted benzaldehyde with an appropriate substituted hydrazide, or alternatively, by reacting an appropriate substituted benzaldehyde with hydrazine, followed by reacting the product with an appropriate acyl halide. Proton Nuclear magnetic resonance $^1$H-NMR and electrospray mass spectrometry (EST-MS) were performed to validate each compound's structure and purity.

5.1 Synthesis of Npam 43

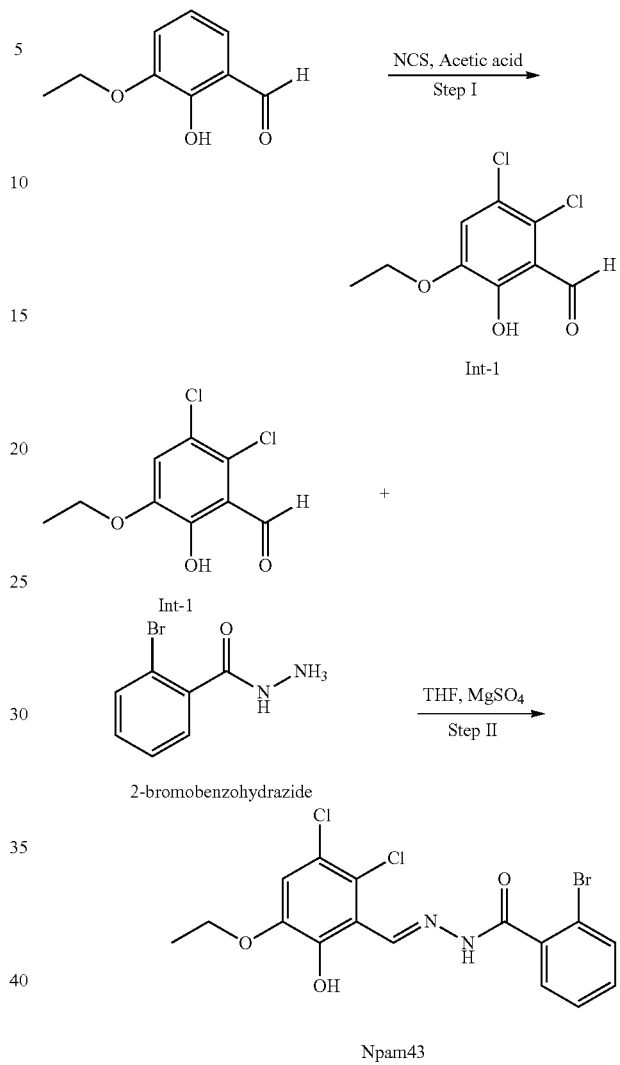

Step I:
2,3-dichloro-5-ethyoxy-6-hydroxy-benzaldehyde (Int-1)

2-hydroxy-3-ethoxybenzaldehyde (1.0 g, 5.2 mmol) was dissolved in acetic acid (20 mL) and N-chlorosuccinimide (NCS) (1.4 g, 11 mmol) was added all at once. The reaction mixture was stirred overnight at 80° C., and then cooled to room temperature. Water and $CH_2Cl_2$ were then added, the phases were separated and the water phase was further extracted with $CH_2Cl_2$, dried over $MgSO_4$ and evaporated under vacuo. The crude product was purified by flash chromatography ($CH_2Cl_2$/hexane) to afford the pure product (1.2 g, 89%) as a yellow solid.

Step II: (E)-2-bromo-N'-(2,3dichlor-5-ethoxy-6-hydroxybenzylidene)benzohydrazide (Npam43)

Dissolve equimolar amounts of 2-bromobenzohydrazide (0.30 mmol) and Int-1 (0.30 mmol) in THF (0.5 M solution). Add 2 equivalents of $MgSO_4$ and heat to reflux for 1 h. The product may precipitate. If not, the reaction was checked by TLC or NMR to ascertain consumption of Int-1. If the product precipitated, it was recovered by filtration and washed with water (2×2 ml) to remove residual MgSO$_4$. If the product did not precipitate, the reaction mixture was diluted with water until the product precipitated. The mixture was acidified to pH 3 with dilute HCl for the removal of residual hydrazine and consequently filtered and if necessary it was recrystallized. The compound is a high-melting solid (mp 210-212° C.). Extraction was avoided. If no precipitation was observed, the solvent was evaporated in vacuo and the compound was purified by flash column chromatography.

$^1$H NMR (400 MHz, DMSO-d$_6$): δ=12.59 (s, 1H), 10.41 (s, 1H), 8.89 (s, 1H), 7.61-7.34 (m, 4H), 7.08 (s, 1H), 4.11 (q, J=6.9 Hz, 2H), 1.41 (t, J=7.0 Hz, 3H).

MS (EI): calcd for (C$_{16}$H$_{13}$BrCl$_2$N$_2$O$_3$+H)$^+$ 433.0, found 433.0; calcd for (C$_{16}$H$_{13}$BrCl$_2$N$_2$O$_3$+Na) 455.0, found 455.0.

5.2 Synthesis of Other Npam Compounds

The following compounds were synthesized in a similar way.

Npam03

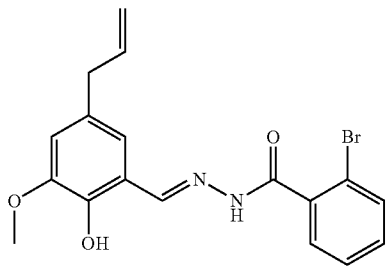 [SMILES: C=CCc1cc(/C=N/NC(=O)c2ccccc2Br)c(O)c(OC)c1]

(E)-N'-(5-allyl-2-hydroxy-3-methoxybenzylidene)-2-bromobenzohydrazide $^1$H NMR (400 MHz, DMSO-d$_6$): δ = 12.030 (s, 1H), 10.293 (s, 1H), 8.472 (s, 1H), 7.993-7.248 (m, 4H), 7.008 (d, J = 1.69 Hz, 1H), 6.868 (d, J = 1.69 Hz, 1H), 5.968 (ddt, J = 17.14, 10.57, 7.80 Hz, 1H), 5.134 (dd, J = 17.14, 2.41 Hz, 1H), 4.980 (dd, J = 10.57, 2.41 Hz, 1H), 3.807 (s, 3H), 3.195 (d, J = 7.8 Hz, 2H).

MS (EI): calcd for (C$_{18}$H$_{17}$BrN$_2$O$_3$) 389.2, found 389.1; calcd for (C$_{18}$H$_{17}$BrN$_2$O$_3$ + Na)$^+$ 411.0, found 411.1.

Npam04 C

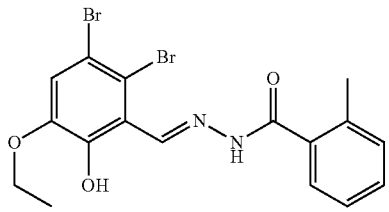 [SMILES: CCOc1cc(Br)c(Br)c(/C=N/NC(=O)c2ccccc2C)c1O]

(E)-N'-(2,3-dibromo-5-ethoxy-6-hydroxybenzylidene)-2-methylbenzohydrazide $^1$H NMR (400 MHz, DMSO-d$_6$): δ = 13.03 (s, 1H), 10.20 (s, 1H), 8.95 (s, 1H), 7.98 (d, 1H), 7.56-7.25 (m, 5H), 4.105 (q, J = 6.9 Hz, 2H), 3.321 (s, 1H), 2084 (s, 1H), 1.35 (t, J = 7.0 Hz, 3H).

MS (EI): calcd for (C$_{17}$H$_{16}$Br$_2$N$_2$O$_3$) 456.1, found 455.9.

Npam05

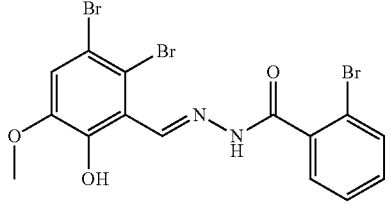 [SMILES: COc1cc(Br)c(Br)c(/C=N/NC(=O)c2ccccc2Br)c1O]

(E)-2-bromo-N'-(2,3-dibromo-6-hydroxy-5-methoxybenzylidene)benzohydrazide $^1$H NMR (400 MHz, DMSO-d$_6$): δ = 12.0 (s, 1H), 10.6 (s, 1H), 8.07 (s, 1H), 7.68 (ddd, J = 8.5, 1.5, 0.5 Hz, 1H), 7.64-7.52 (7.57 (ddd, J = 8.5, 7.6, 1.4 Hz), 7.62 (ddd, J = 8.1, 1.4, 0.5 Hz, 2H)), 7.39 (ddd, J = 8.1, 7.6, 1.5 Hz, 1H), 6.91 (s, 1H), 3.82 (s, 3H).

MS (EI): calcd for (C$_{15}$H$_{11}$Br$_3$N$_2$O$_3$) 507.0, found 507.0.

Npam06

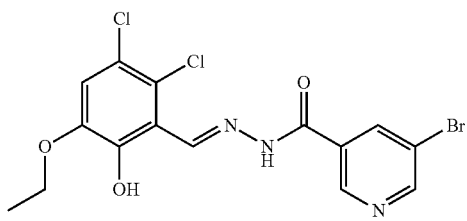 [SMILES: CCOc1cc(Cl)c(Cl)c(/C=N/NC(=O)c2cncc(Br)c2)c1O]

(E)-5-bromo-N'-(2,3-dichloro-5-ethoxy-6-hydroxybenzylidene)nicotinohydrazide $^1$H NMR (400 MHz, DMSO-d$_6$): δ = 12.0 (s, 1H), 10.1 (s, 1H), 9.00 (t, J = 2.0 Hz, 1H), 8.54 (dd, J = 2.0, 1.5 Hz, 1H), 8.12 (s, 1H), 8.03 (dd, J = 2.0, 1.5 Hz, 1H), 7.04 (s, 1H), 4.12 (q, J = 7.0 Hz, 2H), 1.27 (t, J = 7.0 Hz, 3H).

MS (EI): calcd for (C$_{15}$H$_{12}$BrCl$_2$N$_3$O$_3$) 433.1, found 433.1.

Npam07

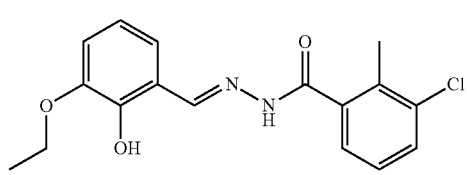 [SMILES: CCOc1cccc(/C=N/NC(=O)c2cccc(Cl)c2C)c1O]

(E)-3-chloro-N'-(3-ethoxy-2-hydroxybenzylidene)-2-methylbenzohydrazide $^1$H NMR (400 MHz, DMSO-d$_6$): δ = 10.252 (s, 1H), 8.522 (s, 1H), 7.602-6.708 (m, 6H), 4.082 (q, J = 7.0 Hz, 2H), 3.322 (s, 3H), 2.083 (s, 1H), 1.349 (t, J = 7.0 Hz, 3H).

MS (EI): calcd for (C$_{17}$H$_{17}$ClN$_2$O$_3$) 333.0, found 333.2.

Npam10

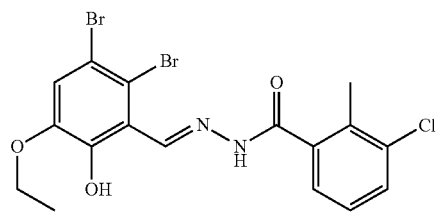 [SMILES: CCOc1cc(Br)c(Br)c(/C=N/NC(=O)c2cccc(Cl)c2C)c1O]

3-chloro-N'-[(1E)-(2,3-dibromo-5-ethoxy-6-hydroxyphenyl)methylidene]-2-methylbenzohydrazide $^1$H NMR (400 MHz, DMSO-d$_6$): δ = 10.287 (s, 1H), 8.05 (s, 1H), 7.59 (dd, J = 7.8, 1.5 Hz, 1H), 7.45-7.36 (7.40 (dd, J = 7.4. 1.5 Hz), 7.41 (dd, J = 7.8, 7.4 Hz), 2H), 6.92 (s, 1H), 4.10 (q, J = 7.0 Hz, 2H), 2.46 (s, 3H), 1.28 (t, J = 7.0 Hz, 3H).

MS (EI): calcd for (C$_{17}$H$_{15}$Br$_2$ClN$_2$O$_3$) 490.6, found 491.0.

Npam12

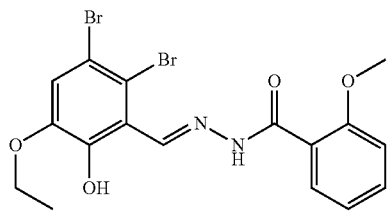 [SMILES: CCOc1cc(Br)c(Br)c(/C=N/NC(=O)c2ccccc2OC)c1O]

(E)-N'-(2,3-dibromo-5-ethoxy-6-hydroxybenzylidene)-2-methoxybenzohydrazide $^1$H NMR (400 MHz, DMSO-d$_6$): δ = 13.074 (s, 1H), 12.135 (s, 1H), 8.996 (s, 1H), 7.662-6.968 (m, 5H), 4.095 (q, J = 6.9 Hz, 2H), 3.891 (s, 3H), 1.343 (t, J = 6.9 Hz, 3H).

MS (EI): calcd for (C$_{17}$H$_{16}$Br$_2$N$_2$O$_4$ + H)$^+$ 473.0, found 473.0.

Npam15 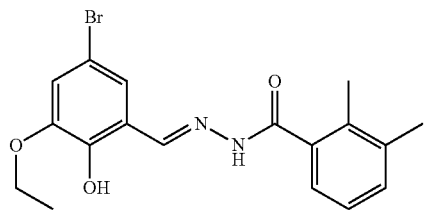 [SMILES: CCOc1cc(Br)cc(/C=N/NC(=O)c2cccc(C)c2C)c1O]

(E)-N'-(5-bromo-3-ethoxy-2-hydroxybenzylidene)-2,3-dimethylbenzohydrazide $^1$H NMR (400 MHz, DMSO-$d_6$): δ = 12.023 (s, 1H), 10.199 (s, 1H), 8.463 (s, 1H), 8.232 (s, 1H), 7.378-6.960 (m, 5H), 4.103 (q, J = 7.0 Hz, 2H), 3.322 (s, 3H), 2.290 (s, 1H), 2.249 (s, 1H), 1.349 (t, J = 7.0 Hz, 3H).

MS (EI): calcd for ($C_{18}H_{19}BrN_2O_3$) 391.3, found 391.2.

Npam17 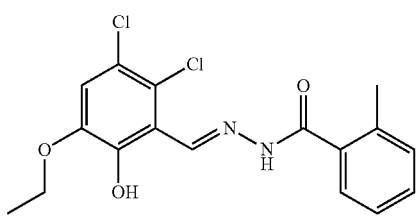 [SMILES: CCOc1cc(Cl)c(Cl)c(/C=N/NC(=O)c2ccccc2C)c1O]

(E)-N'-(2,3-dichloro-5-ethoxy-6-hydroxybenzylidene)-2-methylbenzohydrazide $^1$H NMR (400 MHz, DMSO-$d_6$): δ 12.84 (s, 1H), 8.865 (s, 1H), 7.608-7.184 (m, 4H), 4.076 (q, J = 6.9 Hz, 2H), 2.496 (s, 3H), 1.361 (t, J = 7.0 Hz, 3H).

(EI): calcd for ($C_{17}H_{16}Cl_2N_2O_3$) 367.1, found 367,1; calcd for ($C_{17}H_{16}Cl_2N_2O_3$ + Na)$^+$ 389.1, found 389.1.

Npam18 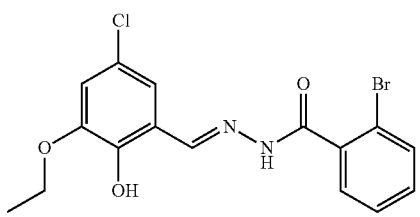

(E)-2-bromo-N'-(5-chloro-3-ethoxy-2-hydroxybenzylidene)benzohydrazide $^1$H MHz (400 MHz, DMSO-$d_6$): δ = 8.488 (s, 1H), 7.749-6.816 (m, 4H), 4.095 (q, J = 7.0 Hz, 2H), 3.320 (s, 3H), 2.084 (s, 1H), 1.355 (t, J = 7.0 Hz, 3H).

MS (EI): calcd for ($C_{16}H_{14}BrClN_2O_3$) 397.6, found 397.1.

Npam20 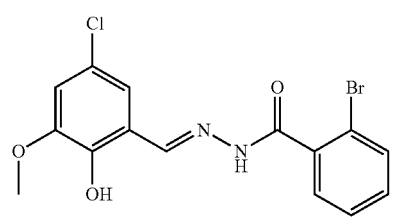 [SMILES: COc1cc(Cl)cc(/C=N/NC(=O)c2ccccc2Br)c1O]

(E)-2-bromo-N'-(5-chloro-2-hydroxy-3-methoxybenzylidene)benzohydrazide $^1$H NMR (400 MHz, DMSO-$d_6$): δ = $^1$H NMR (400 MHz, DMSO-$d_6$): δ =12.2 (s, 1H), 10.35 (s, 1H), 8.08 (s, 1H), 7.80 (d, J = 2.2 Hz, 1H), 7.68 (ddd, J = 8.5, 1.5, 0.5 Hz, 1H), 7.64-7.52 (7.57(ddd, J = 8.5, 7.6, 1.4 Hz), 7.61 (ddd, J = 8.1, 1.4, 0.5 Hz, 2H), 7.39 (ddd, J = 8.1, 1.4, 0.5 Hz, 1H), 6.78 (d, J = 2.2 Hz, 1H), 3.80 (s, 3H).

MS (EI): calcd for ($C_{15}H_{12}BrClN_2O_3$) 383.6, found 383.5.

Npam28

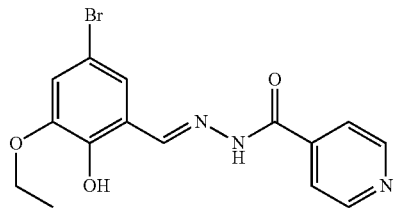 [SMILES: CCOc1cc(Br)cc(/C=N/NC(=O)c2ccncc2)c1O]

N'-[(1E)-(5-bromo-3-ethoxy-2-hydroxyphenyl)methylidene]pyridine-4-carbohydrazide
$^{1}$H NMR (400 MHz, DMSO-d$_{6}$): δ = 12.344 (s, 1H), 10.618 (s, 1H), 8.73 (ddd, J = 4.5, 1.8, 0.4 Hz, 2H), 8.08 (s, 1H), 7.93 (ddd, J = 4.5, 2.7, 0.4 Hz, 2H), 7.81 (d, J = 2.2 Hz, 1H), 6.66 (d, J = 2.2 Hz, 1H), 4.09 (q, J = 7.6 Hz, 2H), 1.25 (t, J = 7.0 Hz, 3H).
MS (EI): calcd for (C$_{15}$H$_{14}$BrN$_{3}$O$_{3}$) 364.1, found 364.1.

Npam29

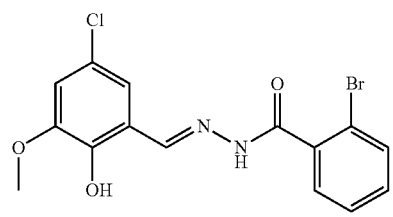 [SMILES: COc1cc(Cl)cc(/C=N/NC(=O)c2ccccc2Br)c1O]

(E)-2-bromo-N'-(5-chloro-2-hydroxy-3-methoxybenzylidene)benzohydrazide
$^{1}$H NMR (400 MHz, DMSO-d$_{6}$): δ = 12.2 (s, 1H), 10.35 (s, 1H), 8.08 (s, 1H), 7.80 (d, J = 2.2 Hz, 1H), 7.68 (ddd, J = 8.5, 1.5, 0.5 Hz, 1H), 7.64-7.52 (7.57(ddd, J = 8.5, 7.6, 1.4 Hz), 7.61 (ddd, J = 8.1, 1.4, 0.5 Hz, 2H), 7.39 (ddd, J = 8.1, 1.4, 0.5 Hz, 1H), 6.78 (d, J = 2.2 Hz, 1H), 3.80 (s, 3H).
MS (EI): calcd for (C$_{15}$H$_{12}$BrClN$_{2}$O$_{3}$) 383.6, found 383.5.

Npam31

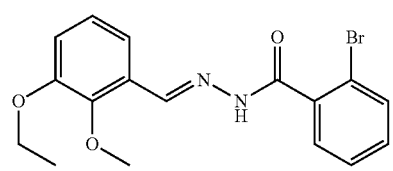 [SMILES: CCOc1cccc(/C=N/NC(=O)c2ccccc2Br)c1OC]

2-bromo-N'-[(1E)-(3-ethoxy-2-hydroxyphenyl)methylidene]benzohydrazide
$^{1}$H NMR (400 MHz, DMSO-d$_{6}$): δ = 12.086 (s, 1H), 8.482 (s, 1H), 7.743-7.144 (m, 7H), 6.843 (dd, J = 8.61, 2.19 Hz, 1H), 4.013 (q, J = 6.9 Hz, 2H), 1.336 (t, J = 7.0 Hz, 3H).
MS (EI): calcd for (C$_{16}$H$_{15}$BrN$_{2}$O$_{3}$) 363.2, found 363.0.

Npam32

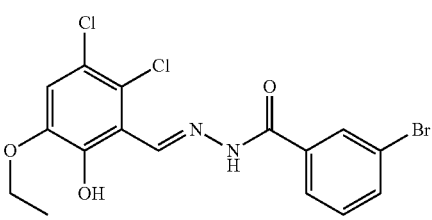 [SMILES: CCOc1cc(Cl)c(Cl)c(/C=N/NC(=O)c2cccc(Br)c2)c1O]

(E)-3-bromo-N'-(2,3-dichloro-5-ethoxy-6-hydroxybenzylidene)benzohydrazide
$^{1}$H NMR (400 MHz, DMSO-d$_{6}$): δ = 12.5 (s, 1H), 10.7 (s, 1H), 8.12 (s, 1H), 7.93 (ddd, J = 8.4, 1.8. 1.2 Hz, 1H), 7.78 (ddd, J = 1.8, 1.7, 0.4 Hz, 1H), 7.58-7.49(7.58(ddd, J = 7.8, 1.7, 1.2 Hz), 7.49 (ddd, J = 8.4, 7.8, 0.4 Hz), 2H), 7.04 (s, 1H), 4.12 (q, J = 7.0 Hz, 2H), 1.27 (t, J = 7.0 Hz, 3H).
MS (EI): calcd for (C$_{16}$H$_{13}$BrCl$_{2}$N$_{2}$O$_{3}$) 432.1 found 432.0.

Npam38

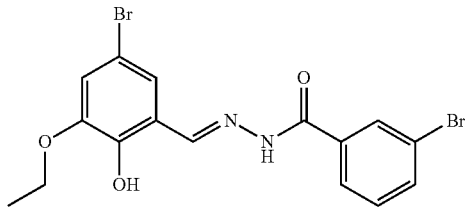 [SMILES: CCOc1cc(Br)cc(/C=N/NC(=O)c2cccc(Br)c2)c1O]

(E)-3-bromo-N'-(5-bromo-3-ethoxy-2-hydroxybenzylidene)benzohydrazide
Npam38 $^1$H NMR (400 MHz, DMSO-d$_6$): δ = 12.2 (s, 1H), 10.35 (s, 1H), 8.59 (s, 1H), 8.15-7.35 (m, 5H), 7.05 (s, 1H), 4.11 (q, J = 6.9 Hz, 2H), 1.41 (t, J = 7.0 Hz, 3H).
MS (EI): calcd for (C$_{16}$H$_{14}$Br$_2$N$_2$O$_3$) 442.1, found 441.9; calcd for (C$_{16}$H$_{14}$Br$_2$N$_2$O$_3$ − H)$^-$ 441.11, found 441.0.

Npam44

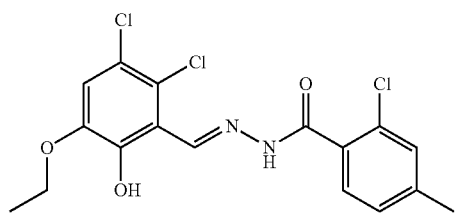 [SMILES: CCOc1cc(Cl)c(Cl)c(/C=N/NC(=O)c2ccc(C)cc2Cl)c1O]

(E)-2-chloro-N'-(2,3-dichloro-5-ethoxy-6-hydroxybenzylidene)-4-methylbenzohydrazide
$^1$H NMR (400 MHz, DMSO-d$_6$): δ = 12.65 (s, 1H), 10.5 (s, 1H), 8.9 (s, 1H), 7.5-7.25 (m, 3H), 7.12 (s, 1H), 4.11 (q, J = 6.9 Hz, 2H), 2.50 (s, 3H), 1.40 (t, J = 7.0 Hz, 3H).
MS (EI): calcd for (C$_{17}$H$_{15}$Cl$_3$N$_2$O$_3$) 401.6, found 401.2; calcd for (C$_{17}$H$_{15}$Cl$_3$N$_2$O$_3$ + Na)$^+$ 423.6, found 423.1.

Npam46

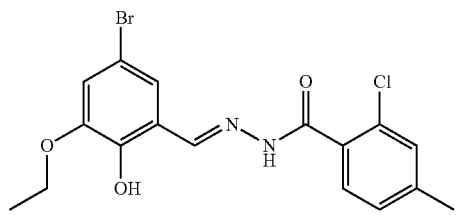 [SMILES: CCOc1cc(Br)cc(/C=N/NC(=O)c2ccc(C)cc2Cl)c1O]

(E)-N'-(5-bromo-3-ethoxy-2-hydroxybenzylidene)-2-chloro-4-methylbenzohydrazide
$^1$H NMR (400 MHz, DMSO-d$_6$): δ = 12.0 (s, 1H), 10.6 (s, 1H), 8.42 (s, 1H), 7.5-6.9 (m, 5H), 4.20 (q, J = 6.9 Hz, 2H), 2.50 (s, 3H), 1.40 (dt, J = 7.0 Hz, 3H).
MS (EI): calcd for (C$_{17}$H$_{16}$BrClN$_2$O$_3$) 411.6, found 411.1; calcd for (C$_{17}$H$_{16}$BrClN$_2$O$_3$ + Na)$^+$ 435.6, found 435.1.

Npam48

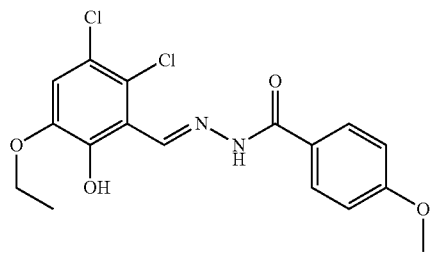 [SMILES: CCOc1cc(Cl)c(Cl)c(/C=N/NC(=O)c2ccc(OC)cc2)c1O]

(E)-N'-(2,3-dichloro-5-ethoxy-6-hydroxybenzylidene)-4-methoxylbenzohydrazide
$^1$H NMR (400 MHz, DMSO-d$_6$): δ = 12.2 (s, 1H), 10.1 (s, 1H), 8.11 (s, 1H), 8.04 (ddd, J = 8.6, 1.8, 0.4 Hz, 2H), 7.07-7.01 (7.04 (s), 7.04 (ddd, J = 8.6, 1.2, 0.4 Hz, 3H), 4.12 (q, J = 7.0 Hz, 2H), 3.86 (s, 3H), 1.27 (t, J = 7.0 Hz, 3H).
MS (EI): calcd for (C$_{17}$H$_{16}$Cl$_2$N$_2$O$_4$) 383.2, found 383.1.

Npam49

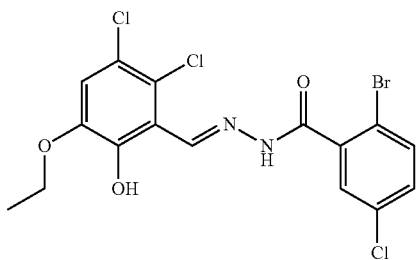 [SMILES: CCOc1cc(Cl)c(Cl)c(/C=N/NC(=O)c2cc(Cl)ccc2Br)c1O]

2-bromo-5-chloro-N'-[(1E)-(2,3-dichloro-5-ethoxy-6-hydroxyphenyl)methylidene]benzohydrazide $^1$H NMR (400 MHz, DMSO-d$_6$): δ = 8.75 (s, 1H), 7.62 (m, 1H), 7.54 (m, 1H), 7.41-7.35 (m, 1H), 7.07 (s, 1H), 4.02 (q, J = 6.9 Hz, 2H), 1.33 (t, J = 7.0 Hz, 3H).

HRMS (EI): called for (C$_{16}$H$_{13}$BrCl$_3$N$_2$O$_3$) 467.0, found 466.9085.

Npam50

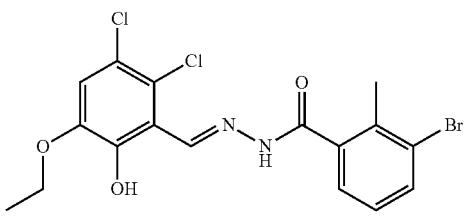 [SMILES: CCOc1cc(Cl)c(Cl)c(/C=N/NC(=O)c2cccc(Br)c2C)c1O]

3-bromo-N'-[(1E)-(2,3-dichloro-5-ethoxy-6-hydroxyphenyl)methylidene]-2-methylbenzohydrazide $^1$H NMR (400 MHz, DMSO-d$_6$): δ = 8.88 (s, 1H), 7.78-7.73 (m, 1H), 7.53-7.48 (m, 1H), 7.29-7.24 (m, 1H), 7.17 (s, 1H), 4.12 (q, J = 6.9 Hz, 2H), 2.53 (s, 3H), 1.47 (t, J = 7.0 Hz, 3H).

HRMS (EI): calcd for (C$_{17}$H$_{15}$BrCl$_2$N$_2$O$_3$ + H)$^+$ 447.0, found 446.9648.

Npam51

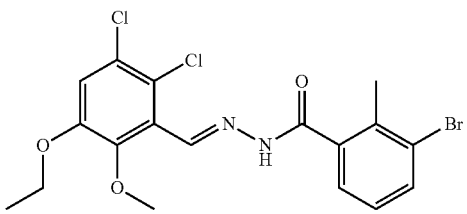 [SMILES: CCOc1cc(Cl)c(Cl)c(/C=N/NC(=O)c2cccc(Br)c2C)c1OC]

3-bromo-N'-[(1E)-(2,3-dichloro-5-ethoxy-6-methoxyphenyl)methylidene]-methybenzohydrazide $^1$H NMR (400 MHz, DMSO-d$_6$): δ = 8.13 (s, 1H), 7.31-7.44 (7.39 (dd, J = 7.8, 7.5 Hz), (7.34 (dd, J = 7.8, 1.5 Hz) 2H), 7.28 (dd, J = 7.5, 1.5 Hz, 1H), 7.03 (s, 1H), 4.11 (q, J = 7.0 Hz, 2H), 3.89 (s, 3H), 2.42 (s, 3H), 1.28 (t, J = 7.0 Hz, 3H).

MS (EI): calcd for (C$_{18}$H$_{17}$BrCl$_2$N$_2$O$_3$) 460.1, found 460.1.

Npam52

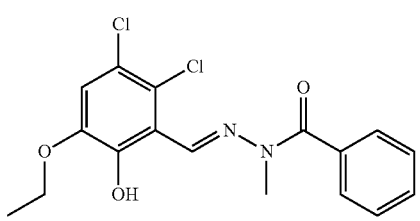 [SMILES: CCOc1cc(Cl)c(Cl)c(/C=N/N(C)C(=O)c2ccccc2)c1O]

N'-[(1E)-(2,3-dichloro-5-ethoxy-6-hydroxyphenyl)methylidene]-N-methylbenzohydrazide $^1$H NMR (400 MHz, DMSO-d$_6$): δ = 12.0 (s, 1H), 8.3 (s, 1H), 7.733-6.885 (m, 8H), 4.02 (q, J = 6.9 Hz, 2H), 3.60 (s, 1H), 1.27 (t, J = 6.9 Hz, 3H).

(EI): calcd for (C$_{17}$H$_{16}$Cl$_2$N$_2$O$_3$) 367.2, found 367.1.

Npam53

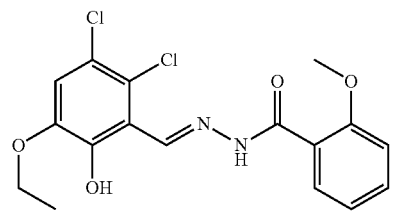 [SMILES: CCOc1cc(Cl)c(Cl)c(/C=N/NC(=O)c2ccccc2OC)c1O]

(E)-N'-(2,3-dichloro-5-ethoxy-6-hydroxybenzylidene)-2-methoxybenzohydrazide
$^1$H NMR (400 MHz, DMSO-$d_6$): δ = 12.906 (s, 1H), 8.973 (s, 1H), 7.695-7.052 (m, 4H), 4.105 (q, J = 6.9 Hz, 2H), 3.902 (s, 3H), 1.289 (t, J = 6.9 Hz, 3H).
MS (EI): calcd for ($C_{17}H_{16}Cl_2N_2O_4$) 383.2, found 383.1; calcd for ($C_{17}H_{16}Cl_2N_2O_3$ + Na)$^+$ 405.2, found 405.1.

Npam54

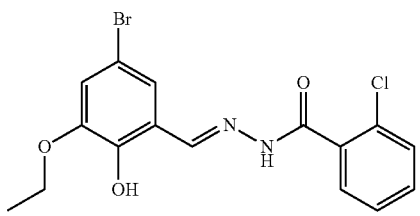 [SMILES: CCOc1cc(Br)cc(/C=N/NC(=O)c2ccccc2Cl)c1O]

N'-[(1E)-(5-bromo-3-ethoxy-2-hydroxyphenyl)methylidene]-2-chlorobenzohydrazide
$^1$H NMR (400 MHz, DMSO-$d_6$): δ = 12.3 (s, 1H), 10.4 (s, 1H), 8.07 (s, 1H), 7.90 (ddd, J = 8.1, 1.5, 0.5 Hz, 1H), 7.81 (d, J = 2.2 Hz, 1H), 7.58-7.48 (7.54 (ddd, J = 8.5, 1.4, 0.5 Hz), 7.53 (ddd, J = 8.5, 7.5, 1.5 Hz, 2H)), 7.36 (ddd, J = 8.1, 7.5, 1.4 Hz, 1H), 6.66 (d, J = 2.2 Hz, 1H), 4.09 (q, J = 7.0 Hz, 2H), 1.25 (t, J = 7.0 Hz, 3H).
MS (EI): calcd for ($C_{16}H_{14}BrClN_2O_3$) 397.7, found 397.1.

Npam55

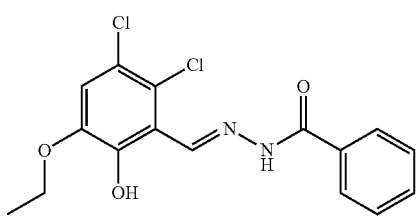 [SMILES: CCOc1cc(Cl)c(Cl)c(/C=N/NC(=O)c2ccccc2)c1O]

(E)-N'-(2,3-dichloro-5-ethoxy-6-hydroxybenzylidene)benzohydrazide
$^1$H NMR (400 MHz, DMSO-$d_6$): δ = 8.12 (s, 1H), 8.03 (dddd, J = 8.5, 1.9, 1.5, 0.4 Hz, 2H), 7.69 (tt, J = 7.5, 1.5 Hz, 1H), 7.59 (ddd, J = 8.5, 7.5, 1.3, 0.4 Hz, 2H), 7.04 (s, 1H), 4.12 (q, J = 7.0 Hz, 2H), 1.27 (t, J = 7.0 Hz, 3H).
MS (EI): calcd for ($C_{16}H_{14}Cl_2N_2O_3$) 353.2, found 353.1, Npam56

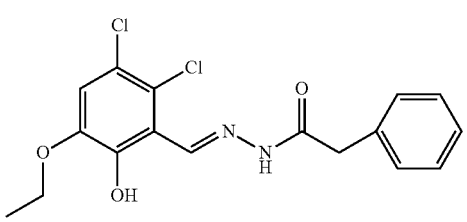 [SMILES: CCOc1cc(Cl)c(Cl)c(/C=N/NC(=O)Cc2ccccc2)c1O]

N'-[(1E)-(2,3-dichloro-5-ethoxy-6-hydroxyphenyl)methylidene]-2-phenylacetohydrazide
$^1$H NMR (400 MHz, DMSO-$d_6$): δ = 12.611 (s, 1H), 8.758 (s, 1H), 7.40-7.22 (7.35 (dddd, J = 7.7, 7.6, 1.8, 0.5 Hz), 7.32 (dddd, J = 7.6, 1.5, 1.2, 0.5 Hz), 5H)), 7.04 (s, 1H), 4.059 (q, J = 6.9 Hz, 2H), 3.588 (s, 2H), 1.318 (t, J = 7.0 Hz, 3H).
MS (EI): calcd for ($C_{17}H_{16}Cl_2N_2O_3$) 367.2, found 367.1.

Npam57

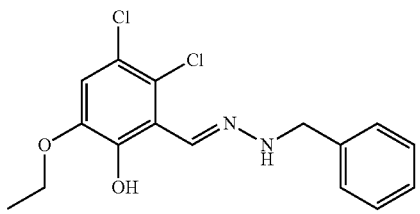 [SMILES: CCOc1cc(Cl)c(Cl)c(/C=N/NCc2ccccc2)c1O]

2-[(1E)-(2-benzylhydrazin-1-ylidene)methyl]-3,4-dichloro-6-ethoxyphenol
$^1$H NMR (400 MHz, DMSO-$d_6$): δ = 12.1 (s, 1H), 10.2 (s, 1H), 7.71 (s, 1H), 7.43-7.27 (7.38 (tdd, J = 7.7, 1.8, 0.5 Hz), 7.32 (tt, J = 7.7, 13 Hz), 3H)), 7.22 (dddd, J = 7.7, 1.3, 1.2, 0.5 Hz, 2H), 7.01 (s, 1H), 4.68 (s, 2H), 4.10 (q, J = 7.0 Hz, 2H), 1.27 (t, J = 7.0 Hz, 3H).
MS (EI): calcd for ($C_{16}H_{16}Cl_2N_2O_2$) 339.2, found 339.1.

Npam80

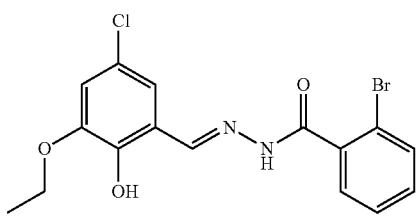 [SMILES: CCOc1cc(Cl)cc(/C=N/NC(=O)c2ccccc2Br)c1O]

(E)-2-bromo-N'-(5-chloro-3-ethoxy-2-hydroxybenzylidene)benzohydrazide
$^1$H NMR (400 MHz, DMSO-$d_6$): δ = 8.472 (s, 1H), 8.276 (d, J = 2.16 Hz. 1H), 7.733-6.826 (m, 5H), 4.094 (q, J = 6.9 Hz, 2H), 3.328 (s, 1H), 2.083 (s, 1H), 1.335 (t, J = 7.0 Hz, 3H).
MS (EI): calcd for ($C_{16}H_{14}BrClN_2O_3$) 397.7, found 397.0.

Npam82

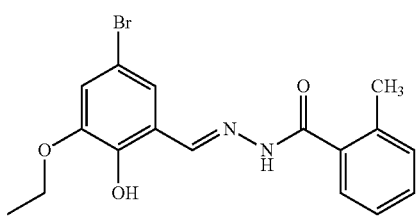

(E)-N'-(5-bromo-3-ethoxy-2-hydroxybenzylidene)-2-methylbenzohydrazide
$^1$H NMR (400 MHz, DMSO-$d_6$): δ = 12.03 (s, 1H), 10.75 (s, 1H), 8.49 (s, 1H), 7.97 (d, J = 2.15 Hz, 1H), 7.502-7.254 (m, 3H), 7.148 (d, J = 2.15 Hz, 1H), 4.102 (q, J = 6.9 Hz, 2H), 3.320 (s, 1H), 2.084 (s, 3H), 1.343 (t, J = 7.0 Hz, 3H).
MS (EI): calcd for ($C_{17}H_{17}BrN_2O_3$) 377.2, found 377.1.

2. In Vitro Identification of Compounds 2.1 HEK293 Cell Culture and Plasmid Transfection Cells were transfected with a combination of pcDNA3-CMV expression vectors, each of which expressed one of the rat recombinant (GluN2AWT, GluN1WT, GluN2BWT) subunits. The sequences of all plasmids were confirmed by automated DNA sequencing. Human Embryonic Kidney 293 (HEK293 cells) were cultured in Dulbecco's Modified Eagle's Medium (DMEM) (Invitrogen) supplemented with 10% fetal bovine serum (FBS). When HEK293 cells achieved 90% confluence, plasmids of either GluN1 & GluN2A or GluN1 & GluN2B were co-transfected into the cells using Lipofectamine 2000 (Invitrogen, 11668019) according to manufacturer's instructions. HEK293 cells were then maintained in the 37° C. incubator with 95% $O_2$ and 5% $CO_2$ for 48 hrs before being used in experiments. The transfection ratios for the NMDAR subunit combinations were all 1:1 (GluN1/GluN2A or GluN1/GluN2B).

2.2 Primary Culture of Cortical Neurons

Dissociated cultures of rat cortical neurons were prepared from 18 day-old Sprague Dawley rat embryos as described previously. To obtain mixed cortical cultures enriched with neurons, uridine (10 μM) and 5-Fluor-2'-deoxyuridine (10 μM) were added to the culture medium at 3 days in vitro (DIV) and maintained for 48 h to inhibit non-neuronal cell proliferation before the cultures were returned to the normal culture medium. Mature neurons (11-14 DIV) were used for experiments. Mouse cortical cultures were prepared using embryos at 18 days post-coitum from litters resulting from heterozygote GluN2A+/− or GluN2B+/− matings. To obtain homozygous and wild-type (WT) littermate control neuronal cultures, cortical cells from individual embryos were plated separately. Genotyping was performed as described previously using tail samples collected from each embryo. To induce neuronal apoptosis, cortical cultures were stimulated with NMDA (50 μM) and glycine (10 μM) for 20 min, or STS (100 nM) for 1 h in Mg2+-free extracellular solution (ECS) containing the following (in mM): 25 HEPES acid, 140 NaCl, 33 glucose, 5.4 KCl, and 1.3 CaCl2, with pH 7.35 and osmolarity 320-330 mOsm. Specific blockade of synaptic NMDA receptors was achieved by treatment with (+)-5-methyl-10,11-dihydro-5H-dibenzo [a,d] cyclohepten- 5,10-imine maleate (MK-801) (10 µM) in the presence of bicuculline (50 µM) for 10-15 min in Mg2+-free ECS, followed by thorough wash with ECS containing 1 mM MgCl2 (normal ECS) to remove any trace of MK-801. GluN2A-specific antagonist NVP-AAM077 (0.4 µM; generous gift from Y P Auberson, Novartis Pharma AG, Basel, Switzerland) or GluN2B-specific antagonist Ro 25-6981 (0.5 µM) was added to the bath medium 10 min before and throughout the treatments.

2.3 Electrophysiology In-Vitro

Whole cell patch-clamp recordings were performed under voltage-clamp mode using an Axopatch 200B or 1D patch-clamp amplifier (Molecular Devices). Whole-cell currents were recorded at a holding potential of −60 mV unless indicated elsewhere, and signals were filtered at 2 kHz, digitized at 10 kHz (Digidata 1322A). Recording pipettes (3-5 MΩ) were filled with intracellular solution containing (mM): CsCl 140, HEPES 10, Mg-ATP 4, QX-314 5, pH 7.20; osmolarity, 290-295 mOsm. BAPTA (10 mM) was added in the intracellular solution (unless otherwise specified). The coverslips were continuously superfused with extracellular solution containing (mM): NaCl 140, KCl 5.4, HEPES 10, CaCl2 1.3, glucose 20, pH 7.4; osmolarity, 305-315 mOsm. NMDA-induced currents were applied by NMDA through perfusion fast-step (Warner Instruments). With perfusion fast-step system, NMDA application was achieved by using a two-square barrel glass tubing and depending on the age of the cultured neurons, CNQX (10 µM), TTX (0.5 µM) or BIC (10 µM) were added in the extracellular solution to minimize the activation of ionotropic glutamate receptors and voltage-gated sodium channels, respectively. All experiments were performed at room temperature. Recordings from at least six HEK293 cells/neurons were performed for all active compounds. Data were pooled among HEK293 cells or primary neurons and composite dose-response data were fitted by the equation Percentage Response=100×Relative Efficacy/[1+(EC50/Concentration)nH], where EC50 is the concentration of agonist that produces a half-maximal response, relative efficacy is the response at maximally effective concentration relative to the maximal response of glutamate, and nH is the Hill slope.

2.4 Electrophysiology Ex-Vivo

Whole cell patch-clamp recordings were performed under voltage-clamp mode using an Axopatch 200B or 1D patch-clamp amplifier (Molecular Devices). Whole-cell currents were recorded at a holding potential of −60 mV unless indicated elsewhere, and signals were filtered at 2 kHz, digitized at 10 kHz (Digidata 1322A). Recording pipettes (3-5 MΩ) were filled with the intracellular solution that contained (mM): CsCl 140, HEPES 10, Mg-ATP 4, QX-314 5, pH 7.20; osmolarity, 290-295 mOsm. BAPTA (10 mM) was added in the intracellular solution (otherwise specified). The coverslips were continuously superfused with the extracellular solution containing (mM): NaCl 140, KCl 5.4, HEPES 10, $CaCl_2$ 1.3, glucose 20, pH 7.4; osmolarity, 305-315 mOsm. NMDA, GABA or AMPA induced currents were either applied by NMDA, GABA, AMPA either through perfusion fast-step (Warner Instruments). With perfusion fast-step system, NMDA, GABA, AMPA application was achieved by using a two-square barrel glass tubing and depending on age of the cultured neurons, CNQX (10 µM) and TTX (0.5 µM) were added in the extracellular solution to minimize the activation of ionotropic glutamate receptors and voltage-gated sodium channels, respectively. All experiments were performed at room temperature. Recordings from at least six HEK293 cells/neurons were performed for all active compounds. Data were pooled among HEK293 cells or primary neurons and composite dose-response data were fitted by the equation Percentage Response=100 K Relative Efficacy/[1+($EC_{50}$/Concentration)$^{nH}$], where $EC_{50}$ is the concentration of agonist that produces a half-maximal response, relative efficacy is the response at maximally effective concentration relative to the maximal response of glutamate, and $n_H$ is the Hill slope.

2.5 Slice Recordings:

6-8 week old C57/Bl6 mice or rats underwent cervical dislocation followed by decapitation. The brain was immediately transferred to an ice cold NMDG-based cutting solution consisting of: (in mM): 120 NMDG, 2.5 KCl, 1.2 NaH2PO4, 25 NaHCO3, 1.0 CaCl2, 7.0 MgCl2, 2.4 Na-pyruvate, 1.3 Na-ascorbate, 20 D-glucose with pH adjusted to 7.35 using HCl acid (unless stated, all chemicals and drugs were purchased from Sigma or BioShop, Canada). The hippocampus was dissected out and transverse hippocampal slices (400 µm) were obtained using a manual tissue chopper (Stoelting, Wood Dale, Ill., USA). Slices recovered in a heated (30° C.) incubating chamber for 1 hr which contained ACSF composed of (in mM): 124 NaCl, 3 KCl, 1.25 NaH2PO4, 1 MgSO47H2O, 2 $CaCl_2$), 26 NaHCO3 and 15 D-glucose which was bubbled continuously with carbogen (95% O2/5% CO2) (pH to 7.3). After 30 additional minutes at room temperature, slices were transferred to a submerged recording chamber and were perfused continuously with carbogenated ACSF (2-3 ml/min). Whole-cell recordings of CA1 pyramidal neurons were performed using the "blind" method with a Multi-Clamp 700B amplifier. EPSCs (excitatory post synaptic currents) were elicited by stimulating the SC pathway. For isolation of NMDAR currents, cells were voltage clamped at +40 mV. Recording pipettes were filled with solution containing (in mM): 122.5 Cs-methanesulfonate, 17.5 CsCl, 2 MgCl2, 10 EGTA, 10 HEPES, 4 ATP (K), and 5 QX-314, with pH adjusted to 7.2 by CsOH. Bicuculline methiodide (10 µM Abcam) to block GABA receptor-mediated inhibitory synaptic currents and CNQX (10 µM; Abcam) to block AMPAR mediated currents were used to further isolate NMDAR currents. To specifically isolate NR2A and NR2B components of NMDAR currents, NVP or ifenprodil were added to inhibit these receptors respectively. Confirmation that the residual synaptic current was conducted by NMDARs was confirmed through application of APV towards the end of experiments. EPSCs were recorded and analyzed using WinLTP. Statistical analyses were completed using GraphPad InStat. An ANOVA comparing NMDAR currents in response to the various drug cocktails with Tukey's posthoc test were conducted to determine differences between treatments. Statistical significance was set at p<0.05 with n=number of cells. Data are presented as mean±SEM. For extracellular recordings (fEPSPs) slicing conditions were similar to the whole-cell preparation. A stimulating electrode were positioned in SC pathway with the recording electrode positioned in stratum *radiatum* in CA1. Recordings were acquired and analyzed using WinLTP. The initial slope of the fEPSP was measured to quantify synaptic strength (Johnston and Wu, 1995). Student's t-test was used for statistical comparisons of mean fEPSP slopes between groups. All values shown are mean±SEM, with n=number of slices.

2.6 Electrophysiology Ex-Vivo (GluN2A-Knockout Mice)

Male and female wild-type or GluN2A KO mice 20-25-day old were anesthetized using Isoflurane and rapidly decapitated. Brains were removed and immersed for 30 sec in cold (2-4° C.) cutting solution containing: 92 mM NMDG, 2.5 mM KCl, 1.25 mM NaH2PO4, 30 mM NaHCO3, 20 mM HEPES, 4.5 mM D-glucose, 5 mM Na-ascorbate, 3 mM Na-pyruvate, 0.5 mM CaCl2, and 10 mM MgCl2. The brain was blocked in melted 3% agar-A (CAS #9002-18-0, Bio Basic Canada Inc.), then glued onto the slicing platform and sectioned coronally at 320 μm thickness with a vibratome (Leica VT 1000S) containing cold (2-4° C.) bubbled (95% O2/5% CO2) cutting solution. Sections that included the prefrontal cortex were transferred into continuously carbogenated pre-warmed (32-34° C.) cutting solution for a period of 12 min time for initial recovery. Then the slices were transferred into a room temperature carbogenated holding solution containing: 119 mM NaCl, 2.5 mM KCl, 1.2 mM NaH2PO4, 24 mM NaHCO3, 12.5 mM D-glucose, 5 mM Na-ascorbate, 3 mM Na-pyruvate, 2 mM CaCl2, and 2 mM MgCl2 for at least 30 min recovery before recording.

2.7 GluN2A-Knockout Mice

Wild-type (WT) and GluN2A knockout (GluN2A−/−) mice with a C57BL/6J background (Sakimura et al., 1995; Townsend et al., 2003) were housed in standard cages (2-3 mice per cage, minimal enrichment) in a colony maintained at 21° C. Animals were maintained on a 12 hour light/dark cycle with access to food and water ad libitum. Each sample (2 μL DNA) was incubated in PCR master mix, consisting of: 14.85 μL Nuclease-free H2O, 2.5 μL 10$ PE Reaction Buffer, 1.4 μL (50 mM) MgCl2, 2.0 μL (2.5 mM) dNTP, 0.5 μL of NR2A1 Primer, 1.0 L of NR2A3 Primer, 0.5 μL of Neo2A Primer, and 0.25 μL (5 U/μL) Taq DNA polymerase (Invitrogen Canada; Burlington, Ontario, Canada). The cycling parameters employed were as follows: first cycle of 4 minutes at 94° C., then 29 cycles of: 30 s at 94° C., 40 s at 60° C. and 60 s at 72° C. Samples were left at 72° C. for 7 minutes and then stored at 4° C. until use. Primers used were NR2A1 (5'-TCT GGG GCC TGG TCT TCA ACA ATT CTG TGC-3'), NR2A3 (5'-CCC GTT AGC CCG TTG AGT CAC CCC T-3') and Neo2A (5'-GCC TGC TTG CCG AAT ATC ATG GTG GAA AAT-3') (Invitrogen Canada; Burlington, Ontario, Canada). PCR products were run on a 1.5% agarose gel with SYBR-safe and visualized using a transilluminator.

2.8 Brain Slice Preparation (GluN2A-Knockout Mice)

Male and female wild-type or GluN2A KO mice 20-25-day old were anesthetized using Isoflurane and rapidly decapitated. Brains were removed and immersed for 30 sec in cold (2-4° C.) cutting solution containing: 92 mM NMDG, 2.5 mM KCl, 1.25 mM NaH$_2$PO$_4$, 30 mM NaHCO$_3$, 20 mM HEPES, 4.5 mM D-glucose, 5 mM Na-ascorbate, 3 mM Na-pyruvate, 0.5 mM CaCl$_2$, and 10 mM MgCl$_2$. The brain was blocked in melted 3% agar-A (CAS #9002-18-0, Bio Basic Canada Inc.), then glued onto the slicing platform and sectioned coronally at 320 μm thickness with a vibratome (Leica VT 1000S) containing cold (2-4° C.) bubbled (95% O$_2$/5% CO$_2$) cutting solution. Sections that included the prefrontal cortex were transferred into continuously carbogenated pre-warmed (32-34° C.) cutting solution for a period of 12 min time for initial recovery. Then the slices were transferred into a room temperature carbogenated holding solution containing: 119 mM NaCl, 2.5 mM KCl, 1.2 mM NaH$_2$PO$_4$, 24 mM NaHCO$_3$, 12.5 mM D-glucose, 5 mM Na-ascorbate, 3 mM Na-pyruvate, 2 mM CaCl$_2$, and 2 mM MgCl$_2$ for at least 30 min recovery before recording.

2.9 Preparation of Hippocanmpal Slices for Immunoblotting with pCREB

Male Sprague Dawley rats 4-8 weeks old (125-200 gm) were decapitated, and their brains were dissected rapidly and placed into ice-cold chopping saline [containing (in mM): 110 sucrose, 60 NaCl, 3 KCl, 1.25 NaH$_2$PO$_4$, 28 NaHCO$_3$, 5 D-glucose, 0.5 CaCl$_2$, 7 MgCl$_2$, and 0.6 ascorbate, saturated with 95% O$_2$/5% CO$_2$]. Then 400 μm transverse slices were prepared with a Vibratome Series 1000 (Pelco, Ted Pella, Redding, Calif.). Slices were transferred immediately into a 1:1 mix of chopping saline and normal ACSF [containing (in mM): 125 NaCl, 2.5 KCl, 1.25 NaH$_2$PO$_4$, 25 NaHCO$_3$, 10 D-glucose, 2 CaCl$_2$, and 1 MgCl$_2$, saturated with 95% O2/5% CO$_2$] and maintained at room temperature for at least 90 min. Then the slices were transferred to ACSF at 32° C. in a submersion chamber for 45-60 min before pharmacological stimulation.

2.10 Electrophysiological Methods (GluN2A-Knockout Mice)

A brain slice was transferred onto a recording chamber on an upright Nikon FN1 microscope and the chamber was continuously perfused with 32° C. carbogenated aCSF recording solution containing: 121.85 mM NaCl, 2.5 mM KCl, 1.2 mM NaH2PO4, 24 mM NaHCO3, 12.5 mM D-glucose, 5 mM Na-ascorbate, 3 mM Na-pyruvate, 2 mM CaCl2, 0.1 mM MgCl2. Pyramidal neurons were identified in layer V of the prefrontal cortex via video monitored infra-red differential interference contrast illumination microscopy using a CFI APO 40× W NIR objective (0.80 numerical aperture, 3.5 mm working distance). Whole cell patch-clamp recordings were performed using patch pipettes with resistances between 5-8 MΩ. Recording pipettes were prepared from borosilicate glass capillaries (1B150F-4, WPI, USA) and filled with pipette solution (280-290 mosM, pH 7.4) containing: 135 mM CsMeSO4, 0.6 mM EGTA, 10 mM HEPES, 2.5 mM MgCl2, 5 mM phosphate Tris, 3 mM Mg-ATP, 0.2 mM GTP Tris, and 5 mM QX314 chloride. Voltage-clamp recordings of current signals were amplified using a MultiClamp 700B amplifier (Molecular Devices), low-pass filtered at 4 kHz, sampled at 10 kHz with a Digidata 1440A data acquisition system (Molecular Devices) and recorded using pCLAMP 10.2 acquisition software (Molecular Devices). Cells were held at −65 mV with correction for liquid junction potential and the series resistance was corrected 40%.

2.11 Site-Directed Mutagenesis.

The site-directed mutagenesis of GluN1 or GluN2A subunits were performed by using the QuikChange method (Stratagene). All mutant clones were confirmed by DNA sequencing. Wild-type or mutant subunits were transfected in HEK293 cells and subjected to electrophysiology examinations. Cells were transfected with a combination of pcDNA3-CMV expression vectors, each of which expressed one of the rat recombinant (GluN2A$_{WT}$, GluN1$_{WT}$, GluN2B$_{WT}$) subunits. An enhanced green fluorescent protein (GFP) pcDNA3-GFP was co-transfected to facilitate microscopic visualization. GluN2A$_{A108G}$, GluN2A$_{P79A}$, GluN2A$_{P178G}$, GluN2A$_{AQ111A}$, GluN2A$_{F115Y}$, GluN2A$_{F115S}$, GluN2A$_{F177S}$, GluN2A$_{J176Y}$, GluN2A$_{M112F}$, GluN1$_{R115E}$, GluN1$_{L135Q}$ plasmids were constructed by site-directed mutagenesis from either GluN1$_{WT}$ and GluN2A$_{WT}$ using PFU DNA polymerase. The sequences of all plasmids were confirmed by automated DNA sequencing.

2.12 Measurement of Ca$^{2+}$ in Rat Cortical Cultures Using a Ca$^{2+}$ Sensitive Dye Rat neurons isolated from the entire cortex were plated onto poly-d-lysine-coated 96-well plates. After 12-14 days in culture, the level of intracellular calcium was assayed using the Fluo-4 No Wash calcium assay kit according to the manufacturer's protocol (Thermo Fisher Scientific). In brief, the neuronal culture medium was removed and replaced with a calcium assay buffer (CAB) containing 1 Y HBSS, 20 mM HEPES, 2.5 mM probenacid, and Fluo4-NW dye mix (pH 7.4; Thermo Fisher Scientific). The cells were then incubated for 45 minutes at 37° C. for dye loading and then 15 minutes at 25° C. To isolate calcium signals mediated by NMDARs, NMDA was used as an agonist (10 μM), and 2 μM glycine were added. The antagonist NVP-AAM007 was used to block the GluN1/GluN2A NMDARs. The calcium fluorescence measurement was performed at 25° C. after 60 seconds of recording with a FLEXStation II benchtop scanning fluorometer (Molecular Devices); then, the NMDAR agonist NMDA (10 μM)/glycine (2 μM) was added at 180 seconds. Fluorescence plate reading continued for a total of 30 mins with use of an excitation of 485 nM, an emission of 538 nM, and a cutoff of 530 nM. The data were recorded using SoftMax Pro software (Molecular Devices).

2.13 Lactate Dehydrogenase Assay.

Lactate dehydrogenase (LDH) is a cytoplasmic enzyme that can convert nicotinamide adenine dinucleotide (NAD) into NADH (the reduced form). LDH is released from cells into culture medium when the plasma membrane integrity is compromised. Therefore, the amount of released LDH represents the degree of cell death. In this study, the extracellular LDH level was measured using an in vitro toxicology assay kit obtained from Sigma-Aldrich (no. TOX-7). The basis of this LDH assay is as follows: (1) LDH reduces NAD into NADH, (2) the resulting NADH is then used in the stoichiometric conversion of a tetrazolium dye, and (3) the resulting colored compound is measured by a spectrophotometric microplate reader at a wavelength of 490 nm. The cell death rate was expressed as a ratio (%) between the absorbance of the treated group and that of the control group.

2.14 Immunoblotting.

Brain tissues or cultured cells were lysed on ice in the lysis buffer and then the solution was centrifuged at 14,000 rpm for 10 min at 4° C. Next, the supernatant was collected and protein concentrations were determined using a BCA protein assay kit (Thermo Scientific, 23227). Equal amount of protein samples were mixed with 4 times sample buffer, boiled at 100° C. for 5 min, and separated on 10% sodium dodecyl sulphate-polyacrylamide gel electrophoresis (SDS-PAGE). Proteins were then transferred to Immobilon-PTM polyvynilidene fluoride (PVDF) membranes (Bio-Rad, 162-0177). The membranes were blocked with 5% non-fat milk in Tris-buffered saline containing 0.1% Tween-20 (TBST) for 1 hour at room temperature, and then incubated overnight at 4° C. with primary antibody. After washing 3×5 min in TBST, protein was visualized in the Bio-Rad Imager using ECL Western blotting substrate (Pierce, 32016). For the detection of phospho-CREB, samples prepared in the same day were used. The polyvinylidene difluoride membrane (Millipore, Bedford, Mass., USA) was incubated with primary antibody against phospho-CREB (Ser133) (Cell Signaling Technology, Beverly, Mass.). For the detection of total CREB, the same polyvinylidene difluoride membrane was stripped and then reprobed with primary antibody against total CREB (Cell Signaling Technology). The band density of each protein was quantified by the Bio-Rad Quantity One software and the relative optical density was analyzed relative to loading total-CREB on the same membrane.

2.15 Excitotoxcity Assays

Cortical cultures were treated with Npam43, and assessed for NMDA-induced excitotoxicity after 20-24 hrs by measuring lactate dehydrogenase (LDH) release. Briefly, cells were treated with 75 μM NMDA for 1.5 h, after which, neurons were washed once with fresh neural basal medium and the media was exchanged with conditional medium. LDH release was measured using an in vitro toxicology assay kit obtained from Sigma-Aldrich (no. TOX-7). The cell death rate was expressed as a ratio (%) between the absorbance of the treated group and that of the control group.

2.16 $H_2O_2$ Cytotoxicity Assay

Cultured cortical neurons were exposed to 600 μM $H_2O_2$ for 1 h to induce neuronal cell death. To show selectivity of Npam43 for GluN1/GluN2A NMDARs, neurons were treated with the GluN1/GluN2B selective antagonist, ifenprodril (3 μM), or the GluN1/GluN2A selective antagonists, NVP-AAM077 (0.2 μM) and TCN-201 (10 μM).

2.17 Reagents.

Phosphate buffer solution was prepared using $NaH_2PO_4.2H_2O$ and $Na_2HPO_4.12H_2O$, the pH of which was adjusted by changing the molar ratio of $NaH_2PO_4.2H_2O$ to $Na_2HPO_4.12H_2O$. Other chemicals used were of analytical grade or better quality and Milli-Q ultrapure water (>18 MU cm) was used throughout the experiments.

2.18 Instrumentation and Chromatographic Conditions.

Npam43 was isolated from the CSF and serum matrix using high performance liquid chromatography and quantified via electrochemical detection. The system consisted of an ESA 582 pump (Bedford, Mass.), a pulse damper (Scientific Systems Inc., State College, Pa.), a Rheodyne Inert manual injector (model 9125i, 20 μL injection loop; Rohnert Park, Calif.), a Tosoh Bioscience Super ODS TSK column (2 μm particle, 2 mm×10 mm; Montgomeryville, Pa.), and an Antec Leyden Intro Electrochemical detector with VT-03 flow cell with a Ag/AgCl reference electrode ($V_{applied}$=+800 mV; Leyden, The Netherlands). The mobile phase was a 20 mM phosphate buffer-acetonitrile (80:20, v/v) mixture, pH 7.0, flowed through the system at 0.1 mL/min. The column was maintained at 40° C. throughout the analysis and the injection volume was 8 uL. Prior to use, the mobile was filtered through a 0.22 mm membrane and degassed using a vacuum pump and maintained under helium purging during experimental testing. EZChrome Elite software (Scientific Software, Pleasanton, Calif.) was used to acquire and analyze chromatographic data.

2.19 Sample Preparation.

Samples were prepared by mixing aliquots (50:50) of the specimen with acetonitrile. The samples were mixed, allowed to rest at ambient temperature for 10 min and centrifuged at 5000 g for 5 min. Eight microliters of the supernatant was injected.

2.20 CSF and Serum Extraction and HPLC-ECD Analysis.

CSF and serum samples generated from the in vivo studies were thawed, and 8 μl was transferred to individual Eppendorf tubes. The internal standard (IS) of 2 μl of 0.5 μg/ml Npam50 was then added, followed by 22 μl of acetonitrile, after which samples were vortexed for 5-10 s and centrifuged for 5 min at 20,000×g to sediment precipitated protein. The clarified supernatant was transferred to HPLC vials for analysis. Standards were prepared in a similar fashion using blank rat csf and serum. Optima grade (Fisher Scientific) solvents and 18 MΩ water (Millipore) were used for sample preparation and subsequent HPLC-ECD analysis. Calibration standards ranged from 0.1-50 uM (6 points, csf equilvalent level) with $R^2$>0.99. The detection limit was >0.8 μM of Npam43. Comparisons of pre- and postspiked serum with neat standards indicated a suppression of about 10% and extraction efficiencies of 95%. Any samples out of the calibration range were diluted 10-fold for reanalysis.

3. In Vivo Analysis of Compounds

3.1 Cerebral Ischemia

Adult male Sprague Dawley rats weighting ~200 g were anesthetized, and the middle cerebral artery (MCA) was exposed by making a craniotomy window (2 mm in diameter) 1 mm rostral to the anterior junction of the zygoma and the squamosal bone. We used the suture ligation method to achieve three-vessel occlusion. The exposed MCA was ligated with a square knot using a 10-0 nylon suture. Next, the bilateral common carotid arteries (CCAs) were clamped with nontraumatic arterial clips. Successful surgery was confirmed by a marked drop in regional cerebral blood flow, monitored by a laser Doppler flowmeter (PF-5010, Periflux system; Perimed AB). After 90 min ischemia, the suture and clips were removed to allow instant reperfusion. Experimental rats were subdivided into groups to receive different doses of Npam43 or saline/vehicle (as indicated) via femoral vein injection. 2,3,5-Triphenyltetrazolium chloride (TTC) was used to evaluate infarct size in stained brain sections. The bolus of Npam43 and saline/vehicle was administered at 3.5 h after stroke onset. To achieve the optimal outcome, another two doses of Npam43 were administered on the second and third days, respectively. Rats were then allowed to recover for different periods of time until additional experiments.

3.2 Magnetic Resonance Imaging

The rats were anesthetized, with body temperature maintained at 37.0±0.5° C. with a heating pad during imaging. The T2-weighted spin-echo imaging sequence (T2WI) was performed by the 3.0 T General Electric imaging system (R4, GE) with the following parameters: repetition time, 4000 ms; echo time, 105 ms; 6-8 contiguous coronal slices with each 2 mm thick. At this stage of stroke development (7 d post-ischemia), brain infarct manifests as high signal (bright white) on the magnetic resonance image (MRI) images. The non-infarct areas were drawn manually from slice to slice and the volumes were measured with Voxtool analysis software (General Electric). The infarct size was quantified by subtracting the non-infarct volume of the ischemic hemisphere from the total volume of the contralateral hemisphere.

3.3 Neurological Behavioral Tests

To assess functional recovery of neural circuits damaged by ischemic insult, three locomotor activity (sensorimotor) deficit modalities were tested: 1) vertical activity (the total number of beam interruptions that occurred in the vertical sensor); 2) number of vertical movements (number of animal rears); and 3) vertical movement time (the amount of time, in seconds, the animal rears) using the VersaMax Animal Activity Monitor (Accuscan Instruments). An ischemic rat was placed into the recording chamber during the 'dark' phase of the day/night cycle, and vertical movement time (seconds) was automatically recorded by computer over a 2 h period. The total length of vertical movement represents the recovery of locomotor circuits injured by ischemic stroke.

Example 1 Identification of Positive Allosteric Modulators

GluN1/GluN2A NMDAR subtypes are an attractive target for positive allosteric modulation. The present inventors employed in silico computational drug discovery methods to conduct a virtual screen of purchasable lead-like compounds from the ZINC database (Irwin, J., et al. Abstr Pap Am Chem Soc (2005) 230:U1009) and some synthetic compounds to identify potential GluN1/GluN2A-NMDAR modulators. The in silico methods included large-scale docking against the interstice interface of the GluN1/GluN2A heterodimer and consensus scoring to select compounds for empirical testing. Candidate compounds were further screened by using GluN1/GluN2A transiently transfected in human embryonic kidney (HEK293) cells and tested by whole-cell patch clamp recordings.

Table 1 shows synthetic and ZINC database compounds that were identified as having a positive modulation effect on GluN1/GluN2A NMDARs.

TABLE 1

Potentiation effects of synthetic (syn) compounds and compounds from the ZINC database

|  | Normalized Potentiation | $EC_{50}$ (μM) | n |
| --- | --- | --- | --- |
| Npam01 | 2.61 ± 9.69% |  | 4.0 |
| Npam02 | 243.57 ± 24.81% |  | 4.0 |
| Npam03 | 97.62 ± 6.03% |  | 4.0 |
| Npam04C | 292.08 ± 44.70% |  | 4.0 |
| Npam05 | 196.54 ± 21.20% |  | 4.0 |
| Npam06 | 201.19 ± 14.63% |  | 4.0 |
| Npam07 | 103.77 ± 11.00% |  | 4.0 |
| Npam08 | 362.76 ± 38.44% |  | 4.0 |
| Npam10 | 206.28 ± 33.62% |  | 4.0 |
| Npam12 | 118.15 ± 35.54% |  | 4.0 |
| Npam13 | 195.38 ± 40.11% |  | 6.0 |
| Npam15 | 89.84 ± 27.86% |  | 4.0 |
| Npam16 | 36.90 ± 5.62% |  | 3.0 |
| Npam17 | 130.54 ± 13.63% |  | 4.0 |
| Npam18 | 213.58 ± 43.58% |  | 4.0 |
| Npam20 | 131.85 ± 23.20% |  | 5.0 |
| Npam21 | 37.27 ± 4.64% |  | 4.0 |
| Npam22 | 59.83 ± 7.55% |  | 4.0 |
| Npam23 | 87.00 ± 6.48% |  | 4.0 |
| Npam24 | 61.57 ± 8.15% |  | 4.0 |
| Npam25 | −14.32 ± 2.20% |  | 3.0 |
| Npam26 | 175.08 ± 14.42% |  | 4.0 |
| Npam27 | −0.278 ± 5.62% |  | 4.0 |
| Npam28 | 30.25 ± 2.87% |  | 4.0 |
| Npam29 | 120.68 ± 9.61% |  | 3.0 |
| Npam30 | 3.99 ± 4.92% |  | 4.0 |
| Npam31 | 15.11 ± 8.78% |  | 4.0 |
| Npam32 | 374.58 ± 19.07% | 0.25 | 4.0 |
| Npam34 | −12.47 ± 2.06% |  | 4.0 |
| Npam35 | 512.24 ± 28.67% | 0.22 | 4.0 |
| Npam36 | 4.02 ± 4.79% |  | 3.0 |
| Npam37 | 435.94 ± 156.01% |  | 4.0 |
| Npam38 | 426.44 ± 87.65% | 0.19 | 4.0 |
| Npam39 | 51.95 ± 11.29% |  | 4.0 |
| Npam40 | 2.51 ± 3.79% |  | 4.0 |
| Npam42 | 43.04 ± 6.55% |  | 4.0 |
| Npam43 | 363.52 ± 27.3% | 0.27 | 6.0 |
| Npam44 | 443.25 ± 83.42% | 0.15 | 4.0 |
| Npam45 | 284.50 ± 85.20% |  | 4.0 |
| Npam46 | 466.57 ± 37.78% | 0.25 | 4.0 |
| Npam47 | 224.79 ± 24.78% |  | 4.0 |
| Npam48 | 441.05 ± 150.41% | 0.10 | 4.0 |
| Npam49 | 530.06 ± 114.00% | 0.19 | 6.0 |
| Npam50 | 441.11 ± 36.50% | 0.25 | 5.0 |
| Npam51 | 33.37 ± 6.39% |  | 4.0 |
| Npam52 | 175.53 ± 25.9% |  | 4.0 |
| Npam53 | 110.23 ± 4.70% |  | 4.0 |
| Npam54 | 43.41 ± 13.48% |  | 4.0 |
| Npam55 | 32.10 ± 3.02% |  | 7.0 |
| Npam56 | 21.48 ± 2.89% |  | 4.0 |
| Npam57 | 105.85 ± 12.62% |  | 4.0 |
| Npam58 | 163.60 ± 13.94% | 0.8 | 4.0 |
| Npam59 | 441.71 ± 65.24% | 0.09 | 6.0 |
| Npam80 | 213.60 ± 29.34% |  | 4.0 |
| Npam82 | 196.21 ± 35.93% |  | 4.0 |

Example 2 Identification of Modulators Selectively Potentiate GluN1/GluN2A-Containing NMDARs The inventors used transiently transfected HEK293 cells expressing either GluN1/GluN2A or GluN1/GluN2B NMDARs and tested by whole-cell voltage patch clamp recordings to see whether selected compounds were controlling the subtype selectivity profile of the drugs.

Table 2 shows some identified compounds that showed a positive modulation of the GluN1/GluN2A NMDARs and/or inhibition effect of GluN1/GluN2B NMDARs. FIG. 1 shows various modulatory effects of several Npam compounds on NMDAR-mediated currents using data from whole-cell patch electrophysiological recordings. FIG. 1 demonstrates that Npam compounds may have a positive potentiation effect on recombinant GluN1/GluN2A NMDARs and/or an inhibitory effect on GluN1/GluN2B NMDARs, and/or little to no effect on GluN1/GluN2B NMDARs.

TABLE 2

Hit compounds identified in the first screen showing positive modulation of GluN1/GluN2A NMDARs and/or inhibition of GluN1/GluN2B NMDARs

| | Normalized Potentiation (100 μM) | | |
|---|---|---|---|
| | GluN1/GluN2A | GluN1/GluN2B | n |
| Npam01 | 26.18 ± 2.24% | −28.00 ± 5.11% | 6 |
| Npam02 | 36.88 ± %3.76 | −4.820 ± 2.83% | 6 |
| Npam04 | 33.71 ± 4.84% | −54.59 ± 5.48% | 6 |
| Npam30 | 52.67 ± 4.87% | −100 ± 2.83% | 4 |
| Npam64 | 28.17 ± 2.47% | −54.57 ± 5.87% | 4 |
| Npam65 | 51.83 ± 6.55%* | −46.87 ± 8.94%* | 4 |
| Npam66 | 45.69 ± 3.87% | −20.89 ± 3.69%** | 4 |
| Npam68 | 35.14 ± 4.85%* | −56.56 ± 7.45%* | 4 |
| Npam69 | 11.11 ± 1.98%* | −34.01 ± 2.47%* | 4 |
| Npam70 | −24.08 ± 2.47%* | −45.57 ± 3.67%* | 4 |
| Npam71 | 41.68 ± 6.78%* | −48.56 ± 4.77%* | 4 |
| Npam72 | 118.45 ± 18.46% | −24.24 ± 4.55% | 4 |
| Npam73 | 30.70 ± 4.76%* | −49.85 ± 6.87%* | 4 |
| Npam75 | 57.18 ± 3.78% | −17.00 ± 2.14% | 4 |

*50 μM
**25 μM

Figure 2:
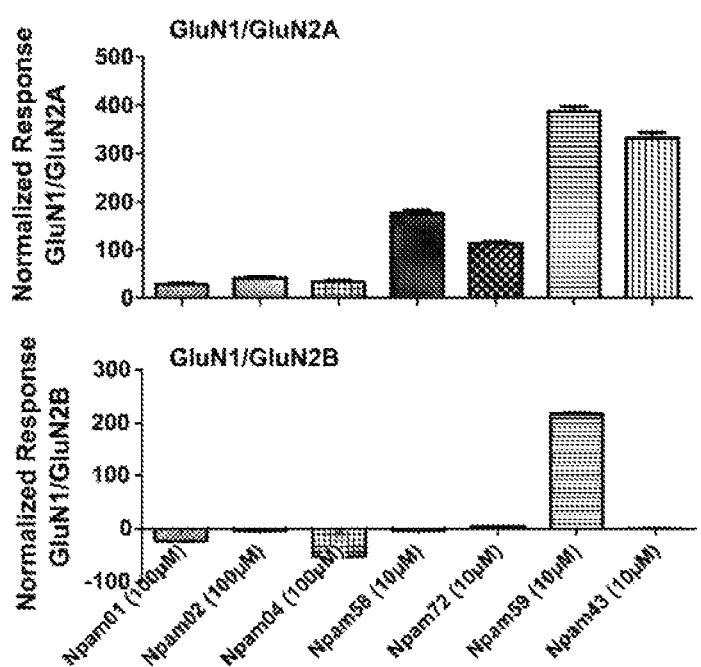
FIG. 2 Modulation effects of different analogs of Npam02 in HEK293 cells expressing GluN1/GluN2A and GluN1/GluN2B NMDARs.

FIG. 2 demonstrate selective potentiation of GluN1/GluN2A-containing NMDARs in the presence of selected Npam compounds. FIG. 2 demonstrates that Npam02, Npam58, Npam72, and Npam43 are selective for GluN1/GluN2A NMDARs in comparison to Npam01, Npam04, Npam59.

Two compounds selectively potentiate GluN1/GluN2A-containing NMDARs, Npam02 and Npam43 were subjected to further investigation. Npam43 is obtained through a structure-activity relationship (SAR) study based on Npam02.

Example 3 Characterization of Npam02

3.1 Evaluation of the Potentiation Effect of Npam02 in HEK293 Cells Transfected with GluN1/GluN2A or GluN1/GluN2B.

Whole-cell patch clamp recordings were performed to measure glutamate evoked currents with chloride-based pipette solutions at a holding potential of −60 mV.

Figure 3:
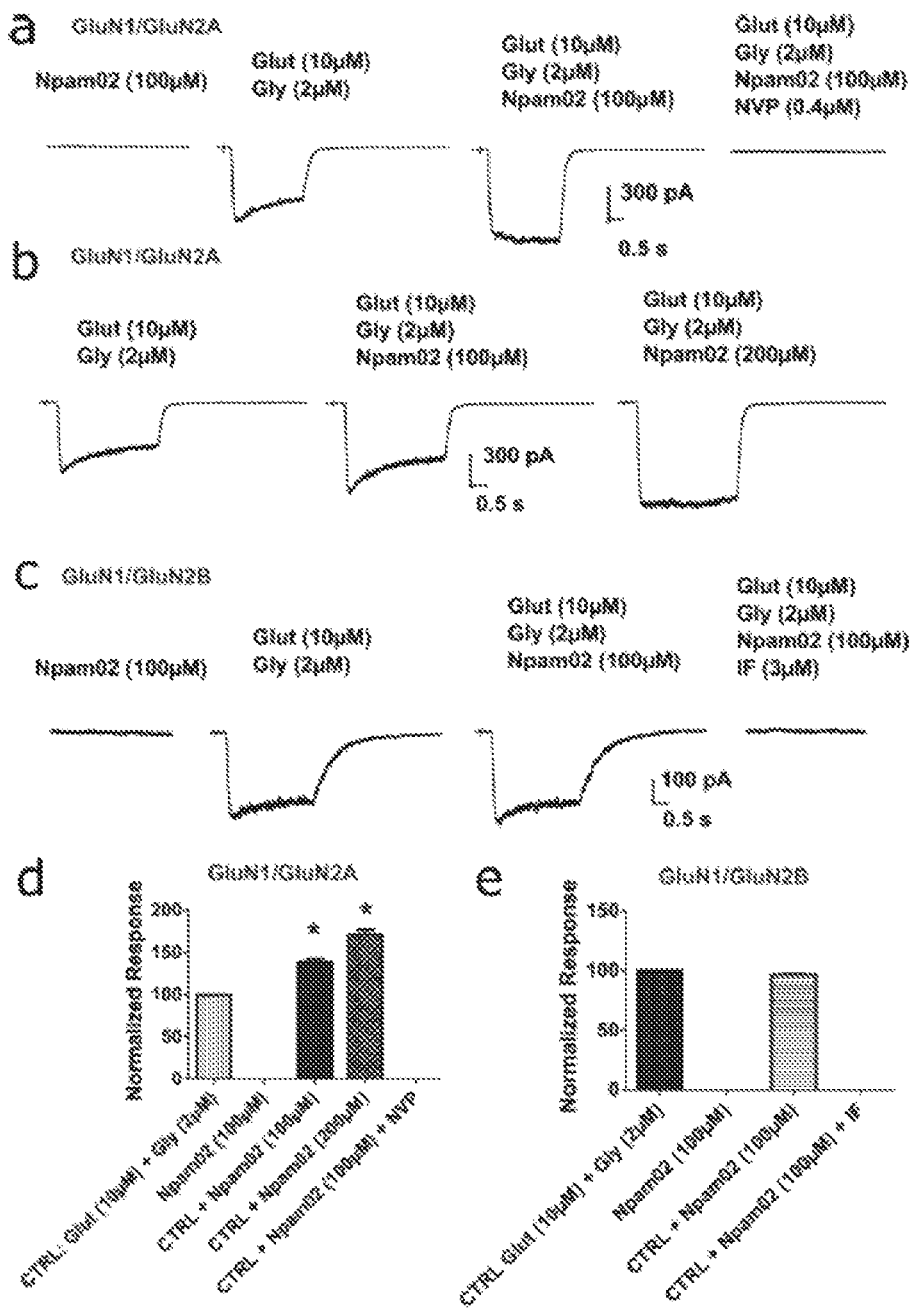
FIG. 3 Npam02 potentiated GluN1/GluN2A-mediated NMDAR currents via direct binding in HEK293 cells transfected with GluN1/GluN2A subunits and did not change GluN1/GluN2B-mediated NMDAR currents.

To rule out the possibility that Npam02 itself may induce any currents in the GluN1/GluN2A or GluN1/GluN2B expressing HEK293 cells, Npam02 (100 μM) was applied alone and no changes of inward or outward currents (FIG. 3a, d). Co-application of Npam02 (100 μM) with co-agonists modestly enhanced NMDA-mediated currents in HEK293 cells expressing GluN1/GluN2A receptors (100 μM; n=6; 38.85±3.70%; P<0.001; and (200 μM; n=6; 71.69±5.03%; P<0.001) (FIG. 3b, d) compared to glutamate application alone (FIG. 3a, d). The increased NMDAR currents could be completely blocked by the co-application of a selective GluN1/GluN2A antagonist of NVP-AAM007 (0.2 μM) in the presence of both co-agonists, confirming that there were no secondary effects attributed to endogenous proteins in HEK293 cells (FIG. 3a, d). In contrast, HEK293 cells expressing the GluN1/GluN2B combination in the presence of Npam02 (100 μM) did not exhibit potentiation of NMDAR currents (FIG. 3c, e). Similarly, Npam02 did not induce currents on its own and NMDAR currents attributed to the GluN1/GluN2B-receptors were successfully blocked by GluN2B specific antagonist ifenprodril (IF; 3 μM) (FIG. 3c, e).

Figure 4:
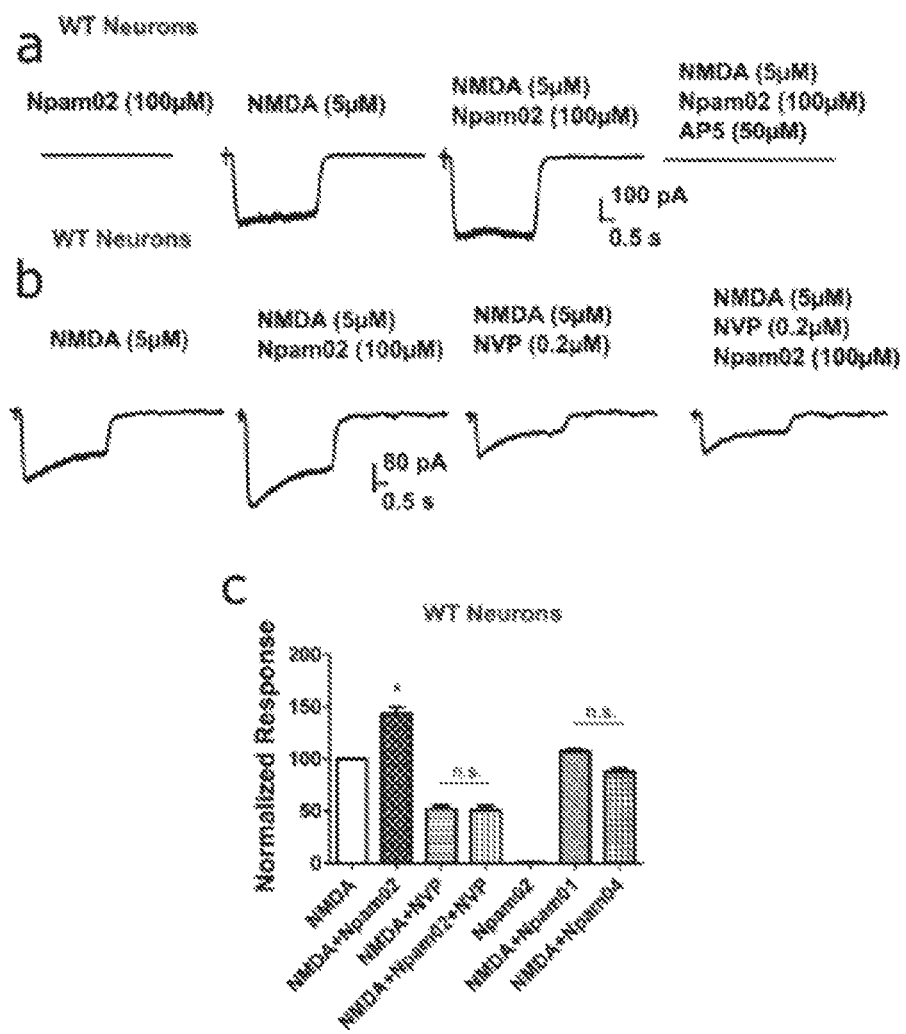
FIG. 4 Npam02 enhanced neuronal NMDAR function in cultured hippocampal neurons and the potentiation effect was blocked by GluN2A antagonist.

3.2 Evaluation of the Potentiation Effect of Npam02 in Mature Cortical Wild-Type and GluN2B-Lacking Neurons Using Whole-Cell Voltage Clamp Recordings To test whether the compound could potentiate NMDARs in mature 14-18 day old cortical neurons at a time when GluN2A receptors are highly expressed, the inventor used NVP-AAM007 (a selective GluN1/GluN2A antagonist at lower concentrations) to block the GluN1/GluN2A-containing receptors. As shown in FIG. 4a, bath application of Npam02 (100 μM) modestly modulated NMDAR currents in the presence of co-agonists NMDA (5 uM) and glycine (2 μM) in hippocampal neurons (n=6, 43.04±6.55%; P<0.001); compared to NMDA control group.

Consistent with the HEK293 cell data, Npam02 was not able to induce inward or outward currents on its own (FIG. 4a). Furthermore, application of APV (50 μM) blocked all currents indicating that the potentiation was mediated through NMDARs and not through secondary effects attributed to other endogenous proteins. On the other hand, the potentiation effect of Npam02 was able to be blocked by the presence of NVP (0.2 μM; n=6, 0.06±1.36%; P>0.05), suggesting that the potentiation effect came from GluN2A-containing NMDARs (FIG. 4b).

Npam01 and Npam04 were also tested in a similar fashion but unlike Npam02, had no observable potentiation or depression effect of the NMDAR-currents (FIG. 4c). This suggested that the potentiation effect of Npam01 and Npam04 previously observed in HEK293 cells expressing GluN1 and 2A NMDARs, could be potentially masked by the inhibition effect on GluN1/GluN2B-containing NMDARs in neurons causing a zero net change in NMDAR currents.

Figure 5:
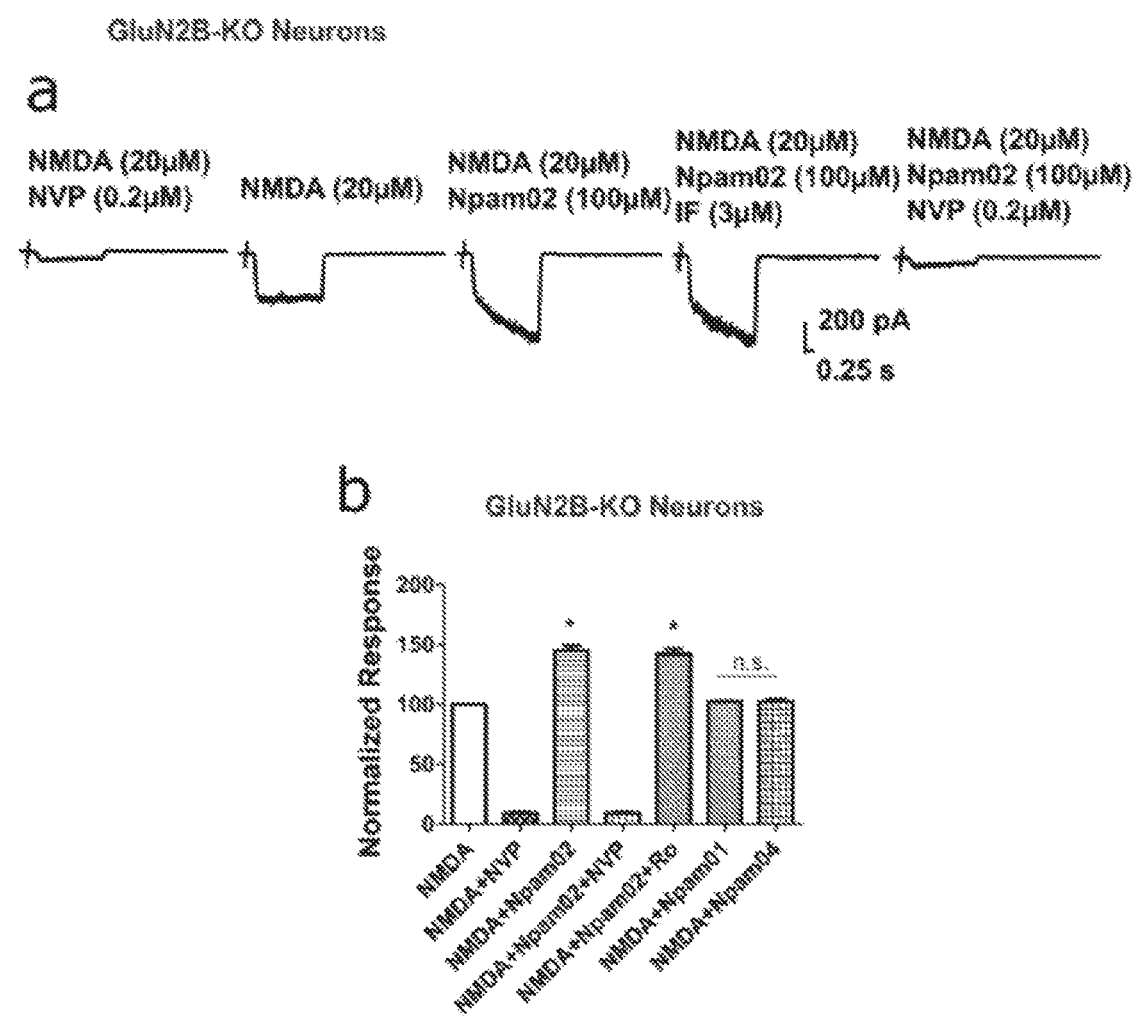
FIG. 5 Npam02 application in genetic deletion of GluN2B subunit cortical culture neurons potentiates GluN2A NMDARs mediated currents.

To further assess whether the potentiation effect on Npam02 was selective towards GluN1/GluN2A-containing NMDARs, Npam02 was tested in neurons lacking the GluN2B subunit. Co-application of NVP-AAM007 (0.2 μM) and NMDA (20 μM) in the conditional GluN2B-knockout neurons, almost completely blocked the NMDAR-currents, (n=4; 90.73±1.11%; P<0.001) (FIG. 5a, b), suggesting that there are still small portion of the residual currents came from the GluN2B. Bath application of Npam02 (100 μM) had a positive modulation effect on NMDAR currents in the presence of co-agonists NMDA (20 μM) and glycine (2 μM) in neurons from GluN2B-lacking mice (n=4; 44.72±4.29%; P<0.001) (FIG. 5a, b) compared to NMDA control group. This was consistent with observations in HEK293 cells expressing GluN1/GluN2A-NMDARs and the potentiation effect observed in wild-type neurons.

Furthermore, to isolate the pure GluN2A-component even further, co-application of the GluN2B-antagonist ifenprodril (IF) with Npam02 resulted in a potentiation effect similar to that observed previously (n=4; 42.22±4.03%; P<0.001) (FIG. 5a, b) compared to NMDA control group.

Finally, GluN2B-knockout cortical neurons were used to determine whether Npam02 is selective for the GluN1/GluN2A-containing NMDARs. Selective GluN2A antagonists were used to block the GluN2A mediated currents and confirm whether the compound discriminated between the two subtypes. Bath application of two co-agonists with GluN2A-NMDAR antagonist NVP-AAM007 (0.2 µM) and Npam02 prevented the potentiation of NMDAR currents by Npam02 (100 µM; n=4; 88.87±3.45% P>0.001) (FIG. 5a, b) compared to NMDA control. This suggests that the residual GluN2B-NMDAR current was not potentiated.

Figure 6:
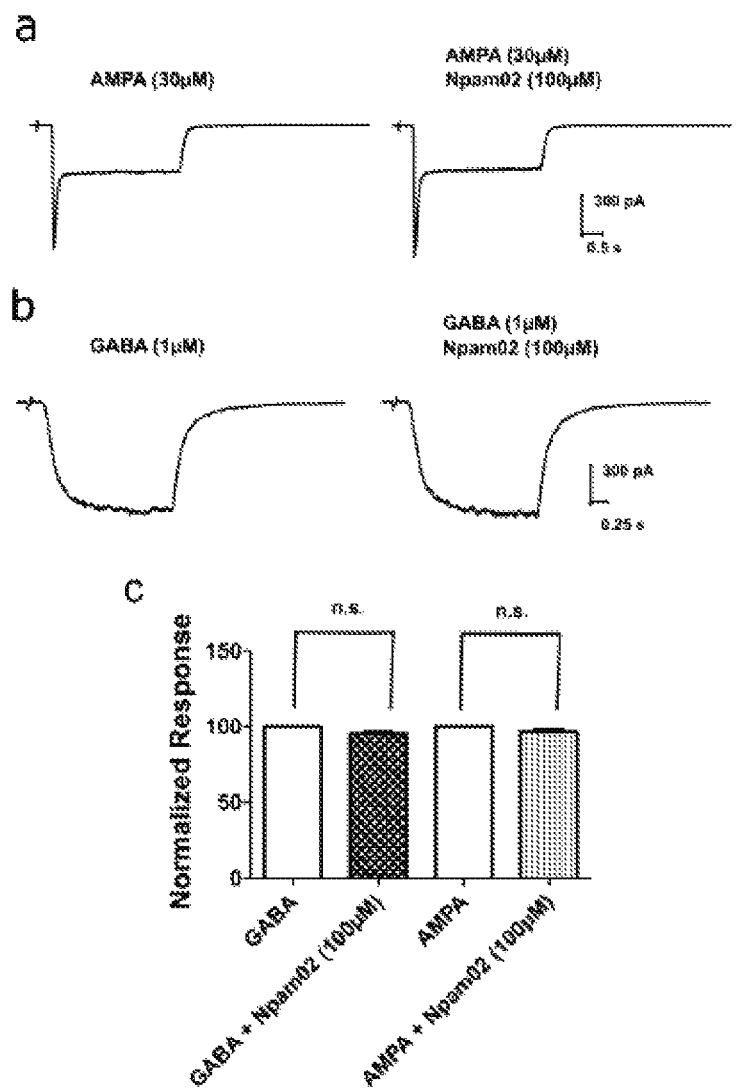
FIG. 6 Npam02 does not affect current responses induced by AMPA and GABA in neuronal cultures.

3.3 Npam02 had No Visible Modulation Effects on AMPAR and GABAR-Mediated Currents in Mature Cortical Neurons Next, the inventor evaluated the selectivity profile for Npam02 on two other key ionotropic receptors of the central nervous system (CNS): α-amino-3-hydroxy-5-methyl-4-isoxazolepropionic acid receptor AMPAR, which are known to be a non-NMDA type ionotropic transmembrane receptor for glutamate that mediates fast synaptic transmission in the central nervous system (CNS) and GABA receptors which are the principal inhibitory ligand-gated ion channel receptor. Whole-cell patch clamp recording was conducted in cultured hippocampal neurons. The tests revealed that Npam02 had no observable effects on either AMPAR (FIG. 6a, c) or GABAR (FIG. 6b, c) mediated currents.

3.4 Npam02 Binding Position in the Interface Site of the GluN1/GluN2A

Figure 7:
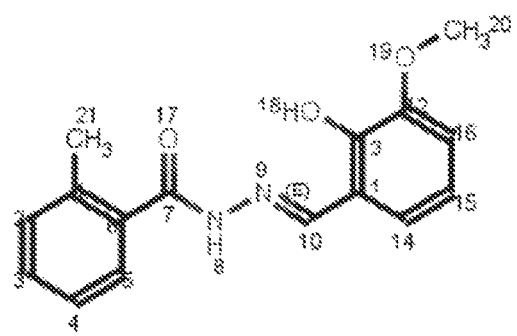

In the structure analysis, it was observed that the GluN1/GluN2A dimer interface was largely surrounded by hydrophobic residues such as (GluN2A$_{F115}$, GluN2A$_{M112}$, GluN2A$_{P79}$, GluN1$_{F113}$, GluN1$_{Y1099}$, GluN1$_{L135}$, GluN2A$_{F177}$, GluN2A$_{P178}$) which are spread all over the pocket and around the Npam02 ligand. In fact, the Npam02 ligand is situated in hydrophobic cage depicted by GluN2A$_{F115}$, GluN2A$_{P79}$, GluN1$_{F113}$ and GluN1$_{Y109}$. This cage is characterized by residues that consist of ring structures in their side chains. This feature was of particular interest because ideally a ring from a ligand within this cage could potentially anchor itself within this area via strong hydrophobic interactions mediated by two Π systems (aryl-aryl). Npam02 appears to conform to this possibility, as its aryl ring (positions 1-6 in FIG. 7) is situated within this area and is hydrophobically linked with all the aforementioned residues which surround Npam02's aryl ring (positions 1-6 in FIG. 7). More specifically, for interactions between two Π systems (aryl-aryl) from the GluN2A$_{F115}$ and the aryl ring from Npam02 (positions 1-6 in FIG. 7), the T-shaped edge-to-face conformation interacts strongly and appears to be energetically attractive and favorable. A similar effect was seen in the opposite side of ligand where the other aryl ring (positions 11-16 in FIG. 7) interacted strongly with a GluN1$_{L135}$, GluN2A$_{F177}$, and GluN2A$_{P175}$. GluN1$_{L135S}$ seems it could interact directly with the second aryl ring of Npam02 via an edge-to-face interaction and the other residues from GluN2A interact hydrophobically as well but most likely to a lesser extent due to their distance further away from the ligand. Conversely, the GluN2A$_{Q111}$ shows a polar hydrogen bond accepting interaction with the proton of the hydroxyl group (position 18 in FIG. 7) of Npam02.

3.5 Site-Directed Mutagenesis of the Predicted Binding Site in the N-Terminal Domain (NTD)

Figure 8A:
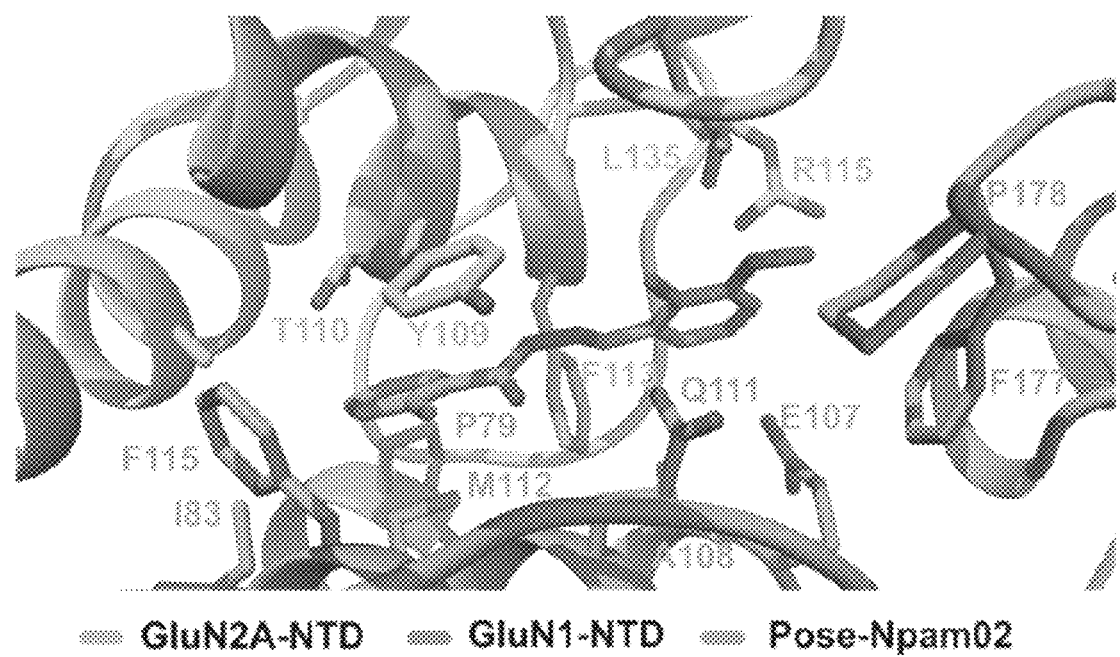
FIG. 8 GluN2A F177 and Q111 form the Npam02 binding pocket between the GluN1 and GluN2A interface of NMDAR receptors in the NTD.
Figure 8B:
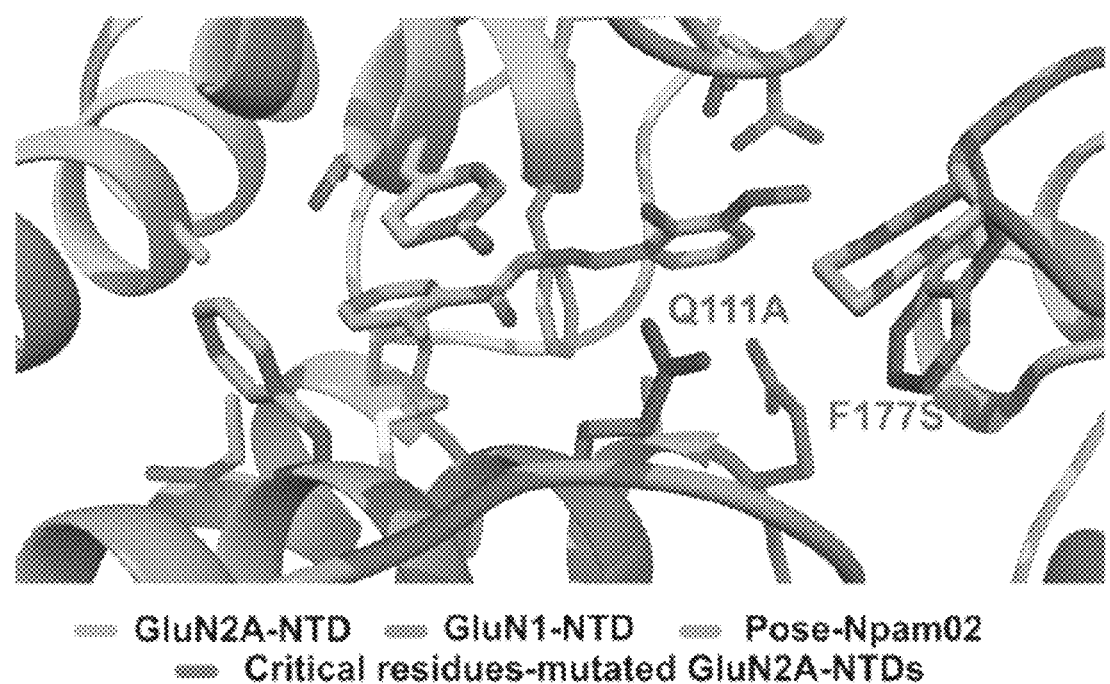
Figure 8C:
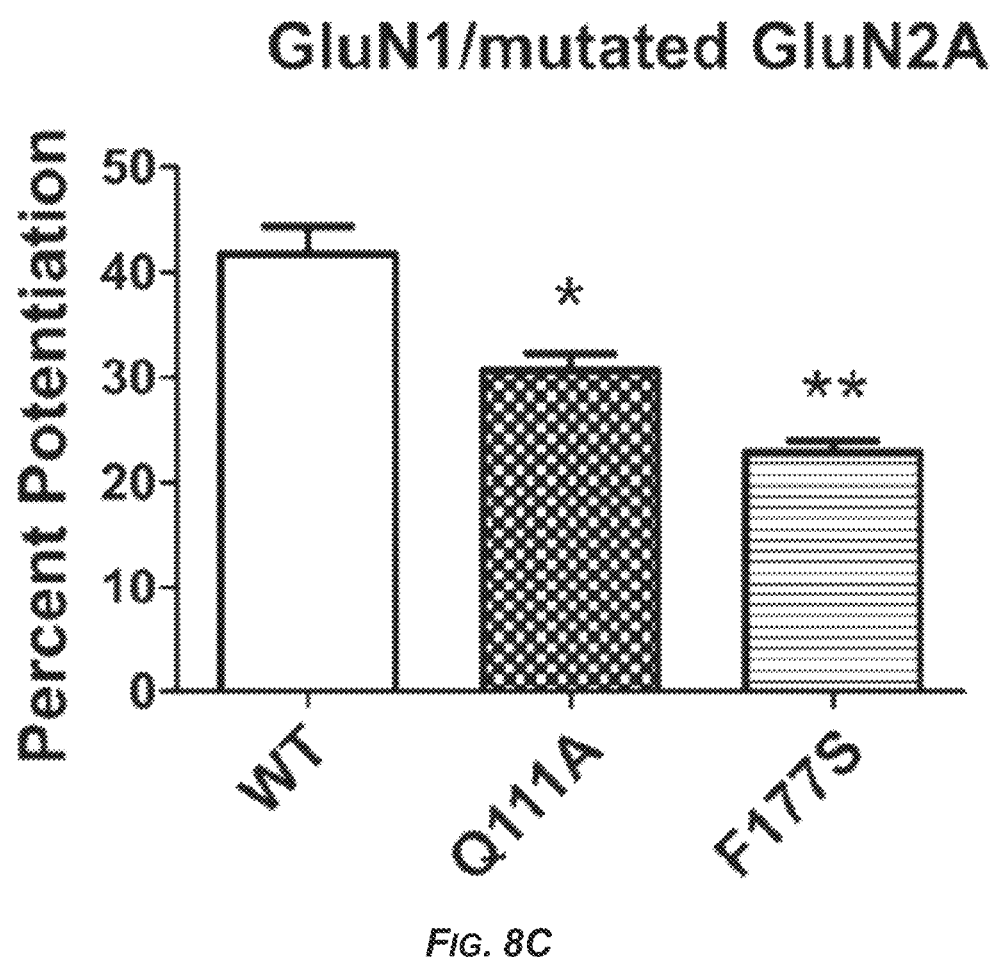

To validate whether the drug is binding to the dimer interface between GluN1 and GluN2A, a site-directed mutagenesis of the N-terminal domain (NTD) pocket was performed. Two residues which were deemed crucial for direct interaction with the drug were selected. Extensive induced-fit docking suggested that Npam02 can occupy and exploit the space between the upper-lobe (R1) of the NTD (FIG. 8a). The inventors therefore tested whether potentiation of the GluN1/GluN2A-containing NMDAR by Npam02 is altered by mutations at residues that surround the pocket interface by choosing side chains for substitutions that occlude the interactions for the compound but do not otherwise perturb the overall protein structure. Docked model of Npam02 in the predicted modulation site showed that two residues GluN2A(Gln$_{111}$) and GluN2A(F$_{177}$) (FIG. 8b) directly interact with Npam02, where the GluN2A(Gln$_{111}$) makes a hydrogen-bond with the hydroxyl group (position 18 in FIG. 7) and GluN2A(F$_{177}$) may elicit hydrophobic interactions towards the aromatic ring (positions 11-16 in FIG. 7). Indeed, a noticeable reduction of the degree of modulation was achieved through both mutations compared to the modulation effect observed to the wild-type GluN1/GluN2A receptor. The modulation effect of Npam02 (100 µM) in the wild-type neurons was (n=7, 41.75±2.62%) (FIG. 8c) significantly reduced when GluN2A was mutated from Gln$_{111}$Ala (n=7, 30.69±1.60%, P>0.05) (FIG. 8c) and reduced further with the Phe$_{177}$Ser mutation (n=7, 22.86±1.12%, P>0.01) (FIG. 8c). This incorporation of these two mutations and the subsequent reduction of the modulation effect of Npam02, suggests that Npam02 could bind to this interstice interface site.

Example 4 Characterization of Npam43

4.1 Npam43 Selectively Potentiates GluN1/GluN2A-Containing NMDAR-Mediated Currents in Transfected HEK293 Cells.

Co-application of Npam43 (10 µM) with co-agonists dramatically enhanced NMDA-mediated currents in HEK cells expressing GluN1/GluN2A receptors compared to glutamate application alone as shown in FIG. 9, suggesting that Npam43 can act as a Npam. In contrast, HEK cells expressing the GluN1/GluN2B subtype in the presence Npam43 (10 µM) did not exhibit potentiation of NDMAR currents (FIG. 9). Similarly, Npam43 did not evoke currents on its own. The enhancement of GluN1/GluN2A NMDAR-mediated currents in HEK cells showed a dose dependent relationship in the presence of Npam43 that reached saturation at ~350% relative to the co-agonists alone baseline and the EC$_{50}$ was pEC50 of ~0.614±0.05 µM (0.24±0.05 µM) as shown in FIG. 9. No dose-dependent enhancement of currents with Nmap43 was observed from GluN2B-containing NMDARs recordings.

Figures 10A, 10B:
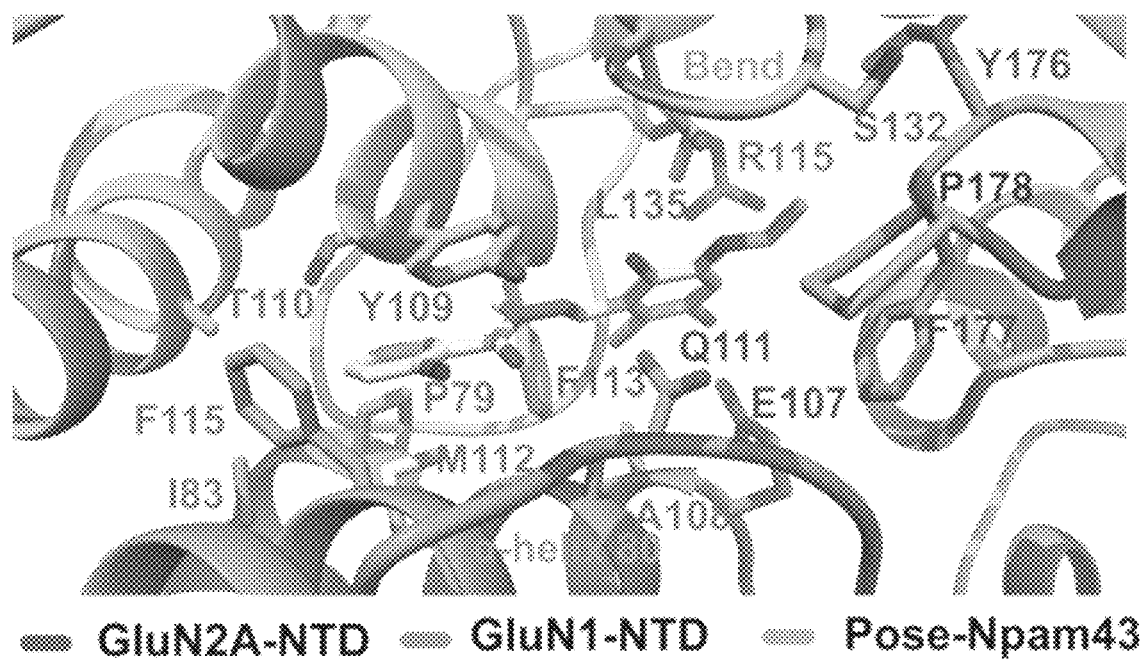
FIG. 10 Critical amino acid residues at the GluN1/GluN2A interface in the N-terminal domain that reduced the potentiation effects of Npam43.

4.2 Critical Amino Acid Residues at the GluN1/GluN2A Interface in the N-Terminal Domain that Reduced the Potentiation Effects The inventors tested whether potentiation of the GluN1/GluN2A-containing NMDAR by Npam43 is altered by mutations at residues that surround the pocket interface by choosing side chains for substitutions that occlude the interactions with the compound but do not otherwise perturb the overall protein structure. Primary sequence of GluN1 and GluN2A subunits is shown in FIG. 10a and bolded residues were defined as being required for the site pocket based on the GluN1/GluN2A 3-D model (FIG. 10b). Docked model of Npam43 in the predicted modulation site showed that GluN1-($Leu_{135}$) (FIG. 10b), which forms a bend just before beta-strand 5, may play a role in interacting with the ligand.

Figure 10C:
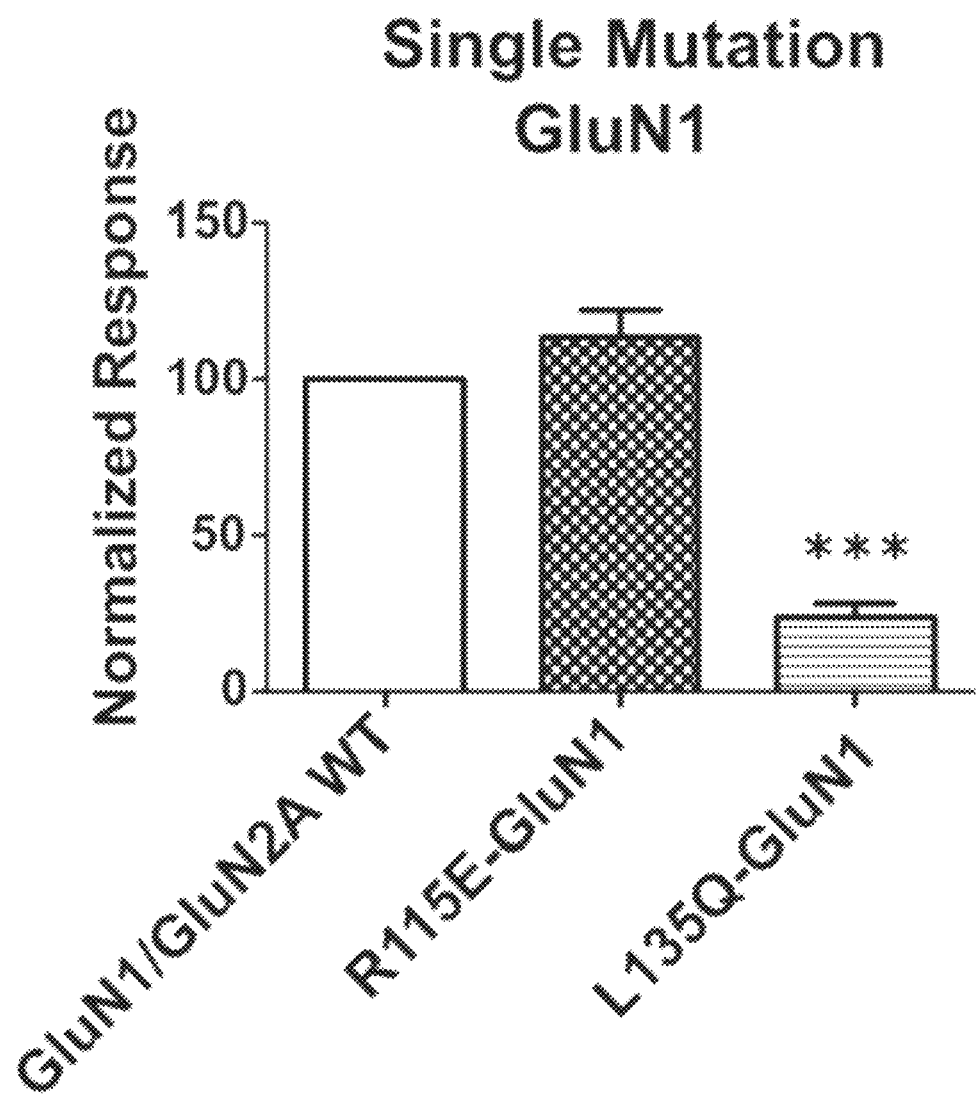
Figure 10D:
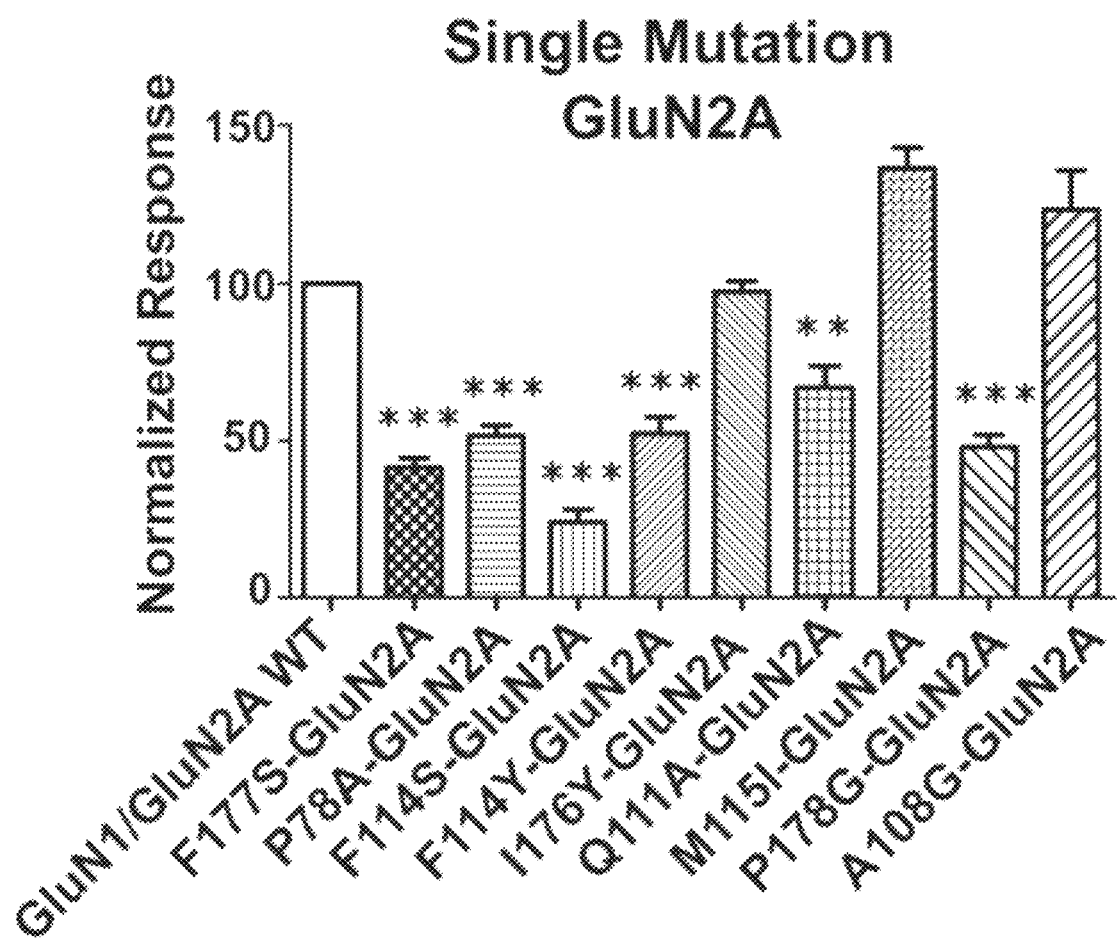
Figure 11A:
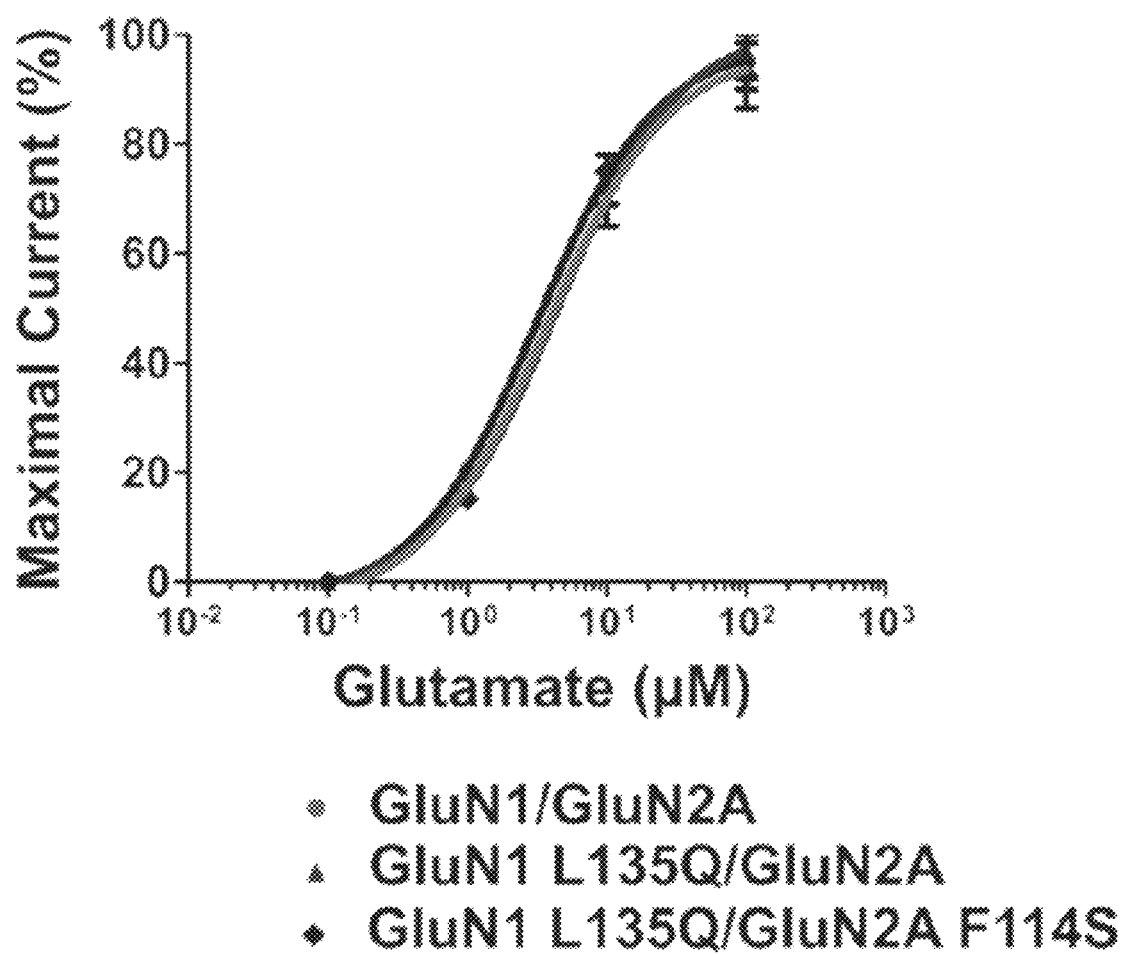
FIG. 11 Dose-response of glutamate in HEK293 cells expressing wild-type GluN1/GluN2A, mutant GluN1 (L135Q) and mutant GluN1 (L135Q)/GluN2A (F115S).

Indeed, a pronounced reduction of the degree of modulation was achieved with GluN1-($Leu_{135}Gln$), which significantly decreased positive modulation by more than 70% (n=6; −77.5±2.12%; P<0.001; normalized to Npam43 response in wild-type GluN1/GluN2A), suggesting that this amino acid is crucial for hydrophobic contacts with the compound (FIG. 10c). The model also showed that GluN2A-($Gln_{111}$) in α-helix 80 made a key H-bond interaction with Npam43 (FIG. 10b) and thus when $Gln_{111}$ was mutated to GluN2A-($Gln_{111}Ala$) a decrease in potentiation was also observed (FIG. 10d), consistent with a role for this region in mediating binding of the ligand (n=6: −38.4±0.78%, P<0.001; normalized to Npam43 response in wild-type GluN1/GluN2A). Furthermore, GluN2A-($Phe_{115}Ser$) mutation located in α-helix 80 reduced positive modulation by (n=6: −67.4±11.8%; P<0.001; normalized to Npam43 response in wild-type GluN1/GluN2A), which suggests that hydrophobic character in this position was essential (FIG. 10d). FIG. 11a shows that GluN1-($Leu_{135}Gln$) and GluN2A-($Phe_{115}Ser$) mutations both independently and together were not a direct reflection of a change in the overall protein structure but rather effected ligand binding. This was demonstrated by the absence of a shift in dose-response of L-glutamate from these two mutations compared with wild-type GluN1/GluN2A.

Figure 10E:
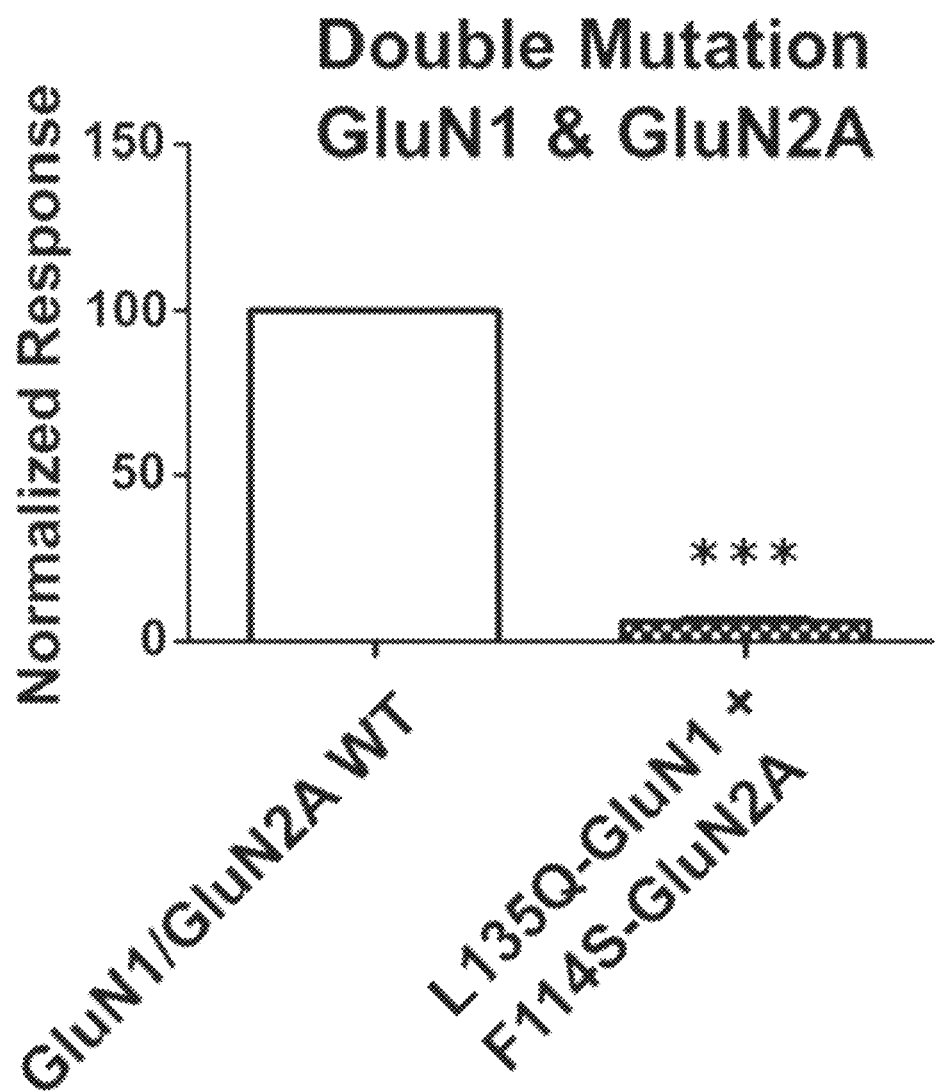
Figure 10F:
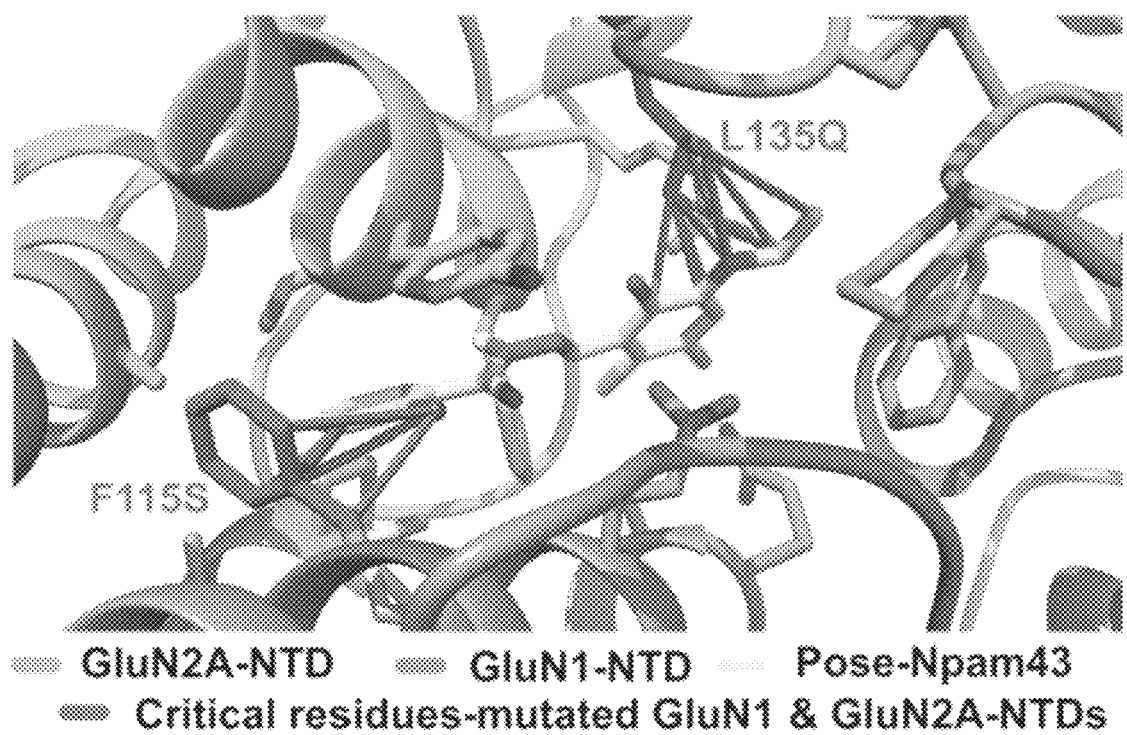
Figure 11B:
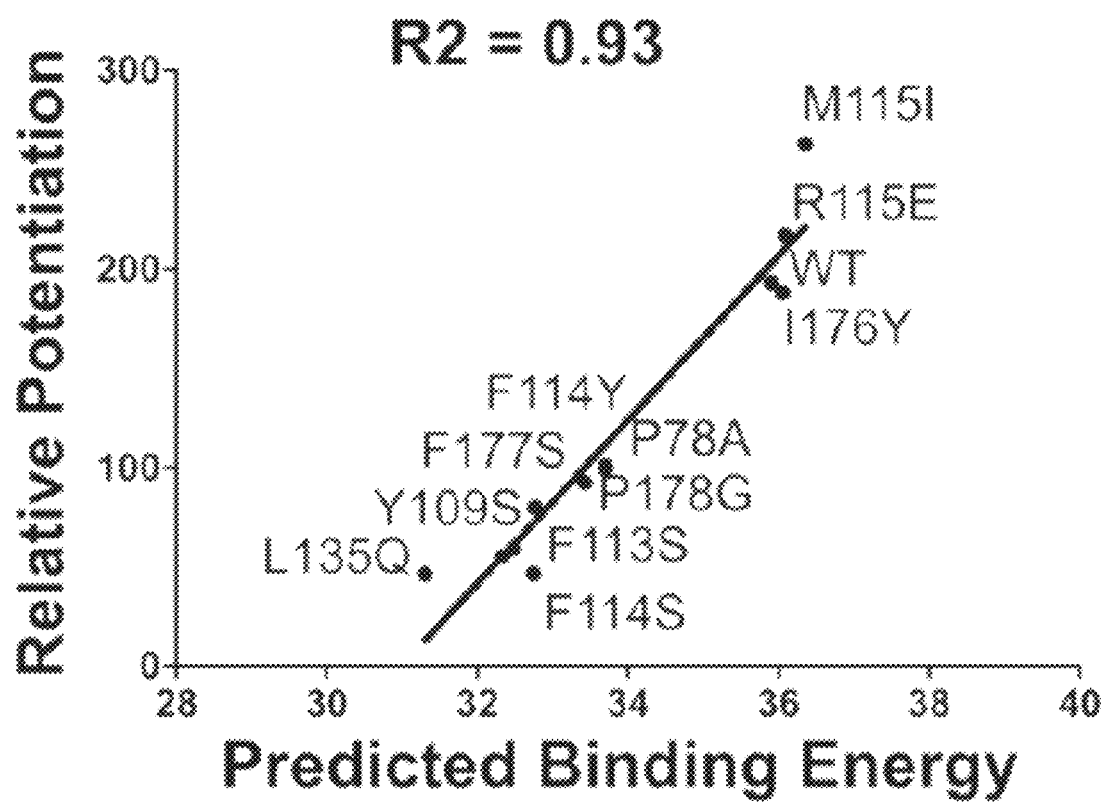

Another 8 mutations, within the defined pocket, summarized in Table 3 and shown in FIG. 10d, also showed significant reduction in potentiation which ranged from (10-62%), strongly suggesting that the ligand binding occurs at this junction in the upper-lobe (R1) of the NTD. Four negative control mutations GluN1-($Arg_{115}Glu$), GluN2A-($Met_{112}Ile$), GluN2A-($Ile_{176}Tyr$) and GluN2A-($Ala_{108}Gly$), which were defined as residues within the binding pocket that did not contribute to ligand binding were also mutated to further demonstrate the accuracy of the model binding site (FIG. 10d). There were no single point mutation Table 3 that was able to abolish the binding of Npam43 so therefore a double mutation; one from GluN1 ($Leu_{135}Gln$) and one from GluN2A ($Phe_{115}Ser$) was constructed and tested to see whether residual positive modulation could be further diminished. The double mutation of the NTD, which individually impair the interaction, further reduced binding of Npam43 as reflected by the additive reduction in potentiation (n=6; −93.9±10.3%; P<0.001; normalized to Npam43 response in wild-type GluN1/GluN2A) (FIG. 10e: FIG. 10f highlights these two point mutations, their relative positions and their strong influential interactions in the binding site). To determine whether this decrease was due to Npam43 binding or to de-sensitivity of the receptor, the dose-response relationship to glutamate activation was investigated with the double mutation with respect to the wild-type. FIG. 11a shows the absence of a significant shift in glutamate dose-response for the double mutation compared to GluN1/GluN2A wild-type receptor, suggesting that the mutation did not affect protein function. To evaluate the accuracy of the structural model used for GluN1/GluN2A NTD, a correlation plot was performed between the relative potentiation of Npam43 observed from the mutated forms of GluN1 or GluN2A in HEK293 cells and the binding energy was predicted from the docking analysis (FIG. 11b). There was a strong correlation $R_2$=0.93 between the observed potentiation and the predicted binding energy suggesting that the model was accurate enough to model the compound inside this binding pocket (FIG. 11b).

TABLE 3

Npam43-induced potentiation of the GluN1 or GluN2A mutants

| | Relative potentiation | Interaction: Direct/Type | Net Difference potentiation | N |
|---|---|---|---|---|
| GluN1$^{WT}$/GluN2A$^{WT}$ | 209 ± 6.7% | | | 6 |
| GluN1/GluN2A$^{Q111A}$ | 129 ± 6.7% | Yes/H-bond | −38.4 ± 0.78% | 4 |
| GluN1/GluN2A$^{F115Y}$ | 100 ± 4.2% | Yes/Hyd-C | −52.2 ± 0.52% | 6 |
| GluN1/GluN2A$^{F177S}$ | 79.9 ± 2.6% | Yes/Hyd-C | −61.7 ± 0.03% | 5 |
| GluN1/GluN2A$^{I176Y}$ | 189 ± 3.8% | No/— | −10.1 ± 0.12% | 3 |
| GluN1/GluN2A$^{M112I}$ | 255 ± 19% | Yes/Hyd-C | +22.2 ± 0.94% | 3 |
| GluN1/GluN2A$^{P178G}$ | 95.5 ± 3.8% | Yes/Hyd-C | −54.3 ± 0.42% | 4 |
| GluN1/GluN2A$^{P79A}$ | 99.3 ± 2.8% | Yes/Hyd-C | −52.5 ± 0.20% | 5 |
| GluN1/GluN2A$^{F115S}$ | 68.1 ± 14.1% | Yes/Hyd-C | −67.4 ± 11.8% | 6 |
| GluN1/GluN2A$^{A108G}$ | 210 ± 9.0% | No/— | +0.48 ± 0.01% | 3 |
| GluN1$^{R115E}$/GluN2A | 255 ± 3.5% | No/— | +22.0 ± 0.40% | 4 |
| GluN1$^{L135Q}$/GluN2A | 47.1 ± 2.8% | Yes/Hyd-C | −77.5 ± 2.12% | 7 |
| GluN1$^{L135Q}$/GluN2A$^{F115S}$ | 12.7 ± 1.8% | Yes, Yes/Hyd-C, Hyd-C | −93.9 ± 10.3% | 5 |

4.3 Modulation of Npam43 on GluN1/GluN2A-Containing NMDARs Potentiates NMDAR-Mediated Currents in Cultured Rat Hippocampal Neurons.

Figure 12:
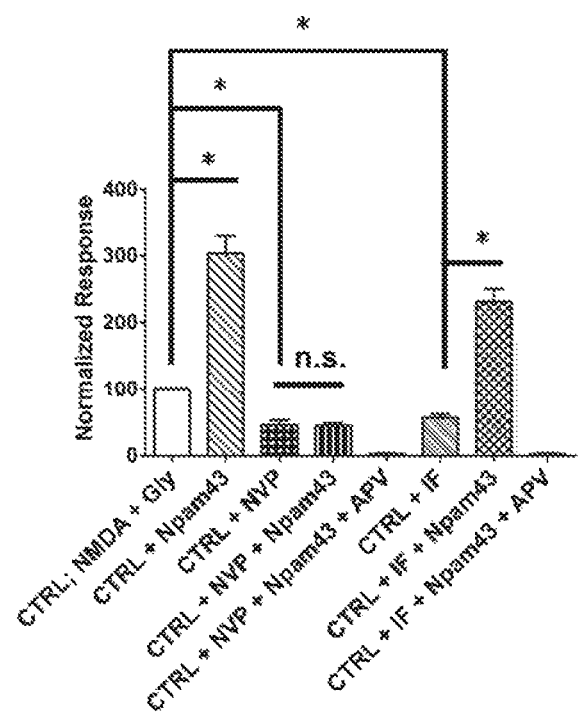
FIG. 12 Npam43 specifically targets GluN2A-containing NMDARs in cultured hippocampal neurons.

FIG. 12 demonstrates that Npam43 selectively potentiates GluN1/GluN2A NMDARs in hippocampal neurons. FIG. 12 shows an increase in potentiation in the presence of Npam43 or through co-application of Npam43 and the GluN1/GluN2B-specific antagonist, ifenprodril (IF; 3 μM). FIG. 12 further shows that treatment with the GluN1/GluN2A-specific antagonist, NVP-AAM077 and the NMDA blocker, AP5, reduces potentiation and eliminate the currents, respectively. A dose-response analysis revealed that Npam43 dose-dependently enhanced the NMDAR currents with an $EC_{50}$ of 0.25±0.12 μM (FIG. 13) and reaches a saturation point at 10 μM (n=6; 322±27% above control level baseline). Additionally, the NMDA dose-response curve was found to be $pEC_{50}$=1.484±0.082 μM or 30.5±11.7 μM in which in the presence of Npam43 (5 μM), shifted left thereby enhancing the affinity of NMDA agonist shown in FIG. 13.

4.4 Npam43 Increases Intracellular $Ca^{2+}$ Via GluN1/GluN2A-Containing NMDARs

Figure 14:
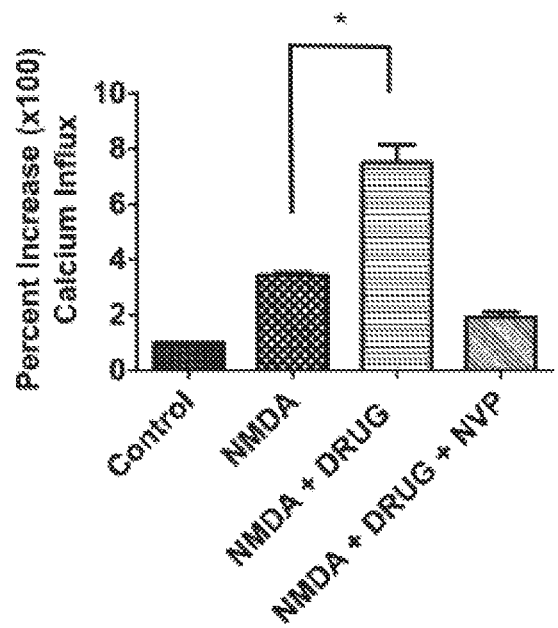
FIG. 14 Npam43 increases intracellular $Ca^{2+}$ via GluN1/GluN2A-containing NMDARs FIG. 15 Npam43 enhances CREB phosphorylation (pCREB), a well characterized indicator for the cell survival signaling activation, in cortical neurons.

A cell-based $Ca^{2+}$ influx assay using primary cultured rat neurons was used to determine if modulation of Npam43 contributes to an increase of intracellular $Ca^{2+}$ and whether this affect was mediated through GluN1/GluN2A-containing NMDARs. NMDA (10 μM) and glycine (2 μM) were added to cell cultures to activate NMDARs. Application of Npam43 to cultured neurons increased the $Ca^{2+}$ influx fluorescence signal shown in FIG. 14. To determine whether this influx of $Ca^{2+}$ was through GluN1/GluN2A-containing NMDARs, the inventors co-applied GluN2A antagonist NVP-AAM0077 and observed marked reduction of $Ca^{2+}$ influx in response to Npam43 suggesting that GluN2A receptors mediate the enhanced calcium influx shown in FIG. 14.

Example 5 Neuroprotective Effects of Npam43

5.1 Phosphorylation of CREB (pCREB)

Figure 15:
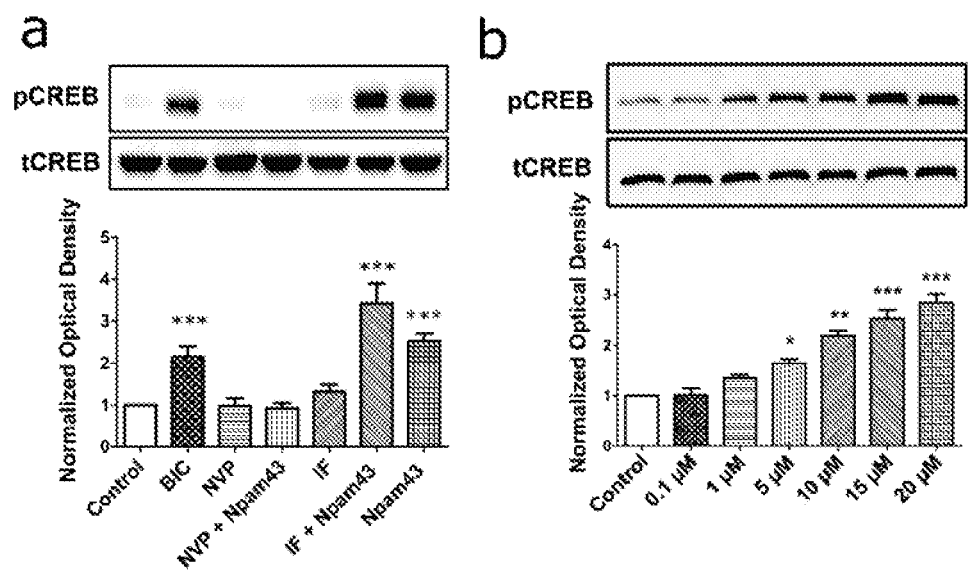

Phosphorylation of CREB is a reliable index of cell survival pathway activation. FIG. 15a demonstrates that CREB phosphorylation (pCREB) increases with Npam43 treatment in the presence or absence of the GluN1/GluN2B antagonist, ifenprodril. FIG. 15a further shows that the GluN1/GluN2A-specific antagonist, NVP-AAM007, reduces Npam43-induced pCREB in comparison to the positive control, bicuculline (BIC; 10 μM). FIG. 15b demonstrates a dose-dependent effect of Npam43 in relation to increased pCREB.

5.2 Reduction of NMDA-Induced Excitotoxicity and $H_2O$-induced Cytotoxicity

Figure 16:
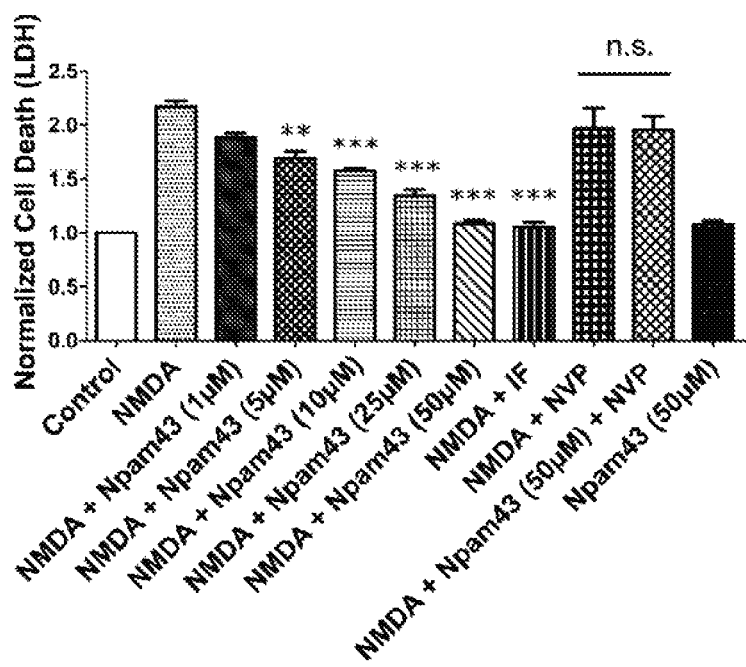
FIG. 16 Npam43 protects against NMDA-induced excitotoxicity in cortical neurons
Figure 17:
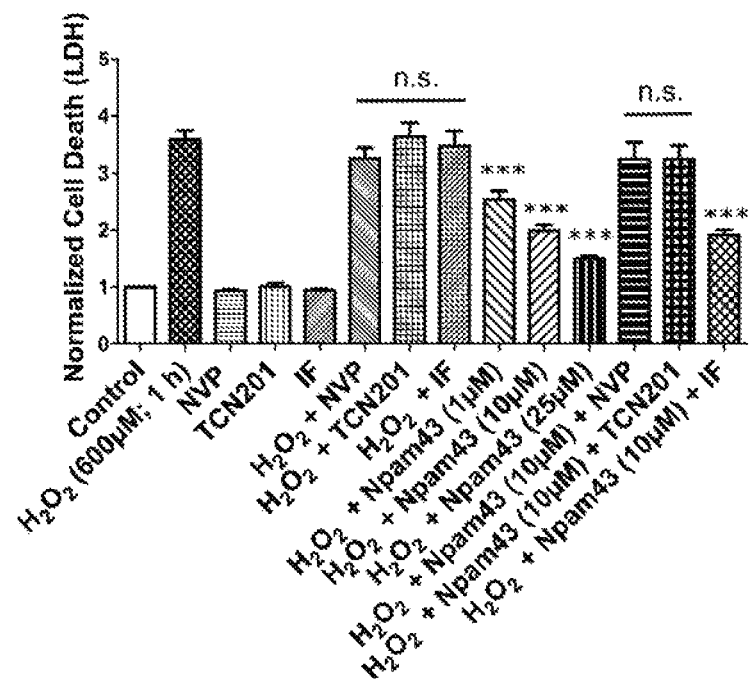
FIG. 17 Npam43, by increasing the activation of GluN2A-containing NMDARs, also protects against non-NMDA-dependent, $H_2O_2$-induced oxidative cytotoxicity in cortical neurons.

FIGS. 16-17 show that NMDA-induced excitotoxicity and $H_2O_2$-induced non-NMDAR dependent cytotoxicity in cortical neurons is reduced with treatment of Npam43 in the absence of the GluN1/GluN2A antagonist, NVP-AAM007. FIG. 16 further shows a dose-dependent effect of Npam43 in relation to NMDA-induced excitotoxicity. FIG. 17 shows that exposure to $H_2O_2$ increases neuronal cell death. FIG. 17 further shows that $H_2O_2$-induced cytotoxicity is reduced in the presence of Npam43, except with co-treatment of GluN1/GluN2A antagonists (NVP-AAM077, 0.2 μM; and TCN-201, 10 μM).

Example 6 Characterization of Npam43 in Slices (Ex-Vivo)

Figure 18:
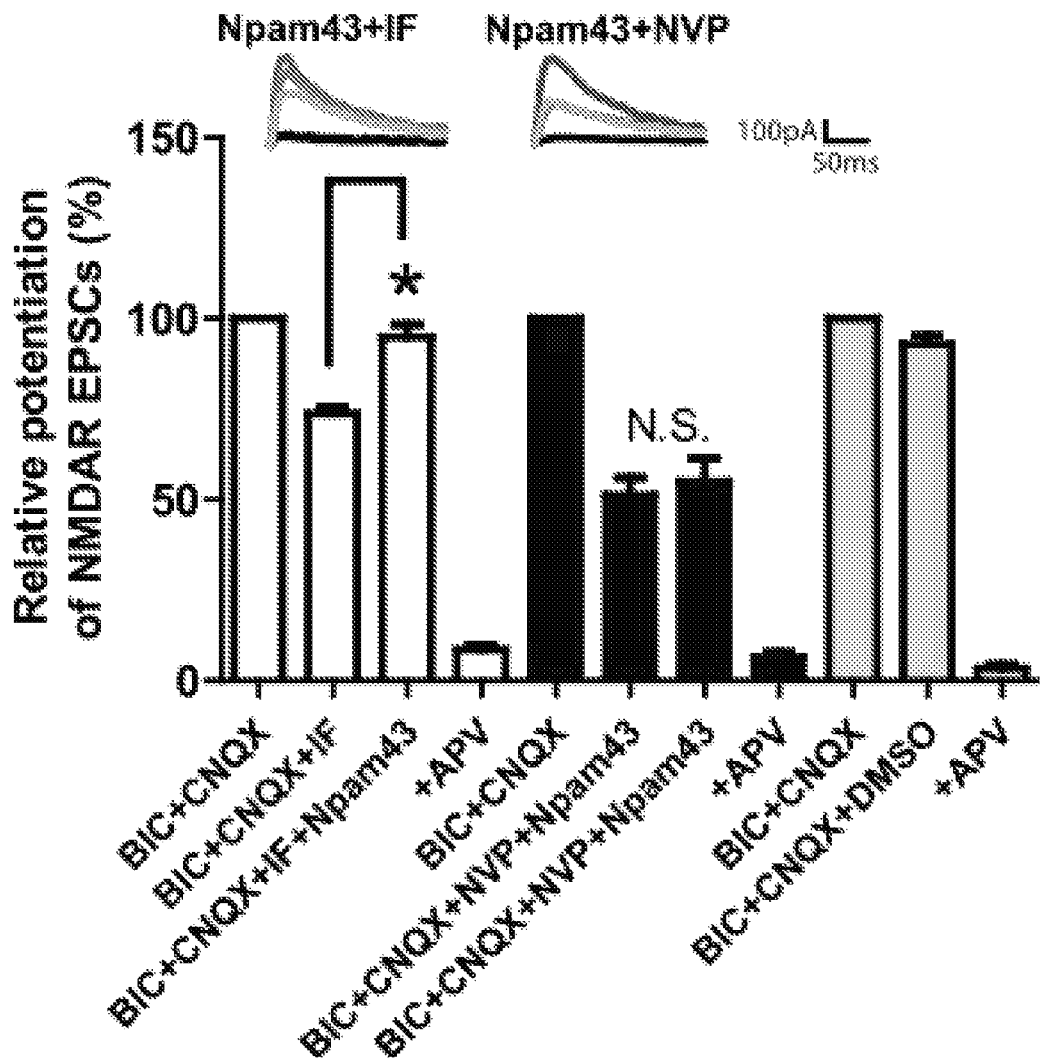
FIG. 18 Npam43 enhances the GluN2A component of synaptic transmission in hippocampal slices FIG. 19 Npam43 facilitates long-term potentiation (LTP) in hippocampal slices FIG. 20 Npam43 enhances the NMDA-induced currents in CA1 neurons of hippocampal slices of wild-type, but not GluN2A-knockout mice.
Figure 19:
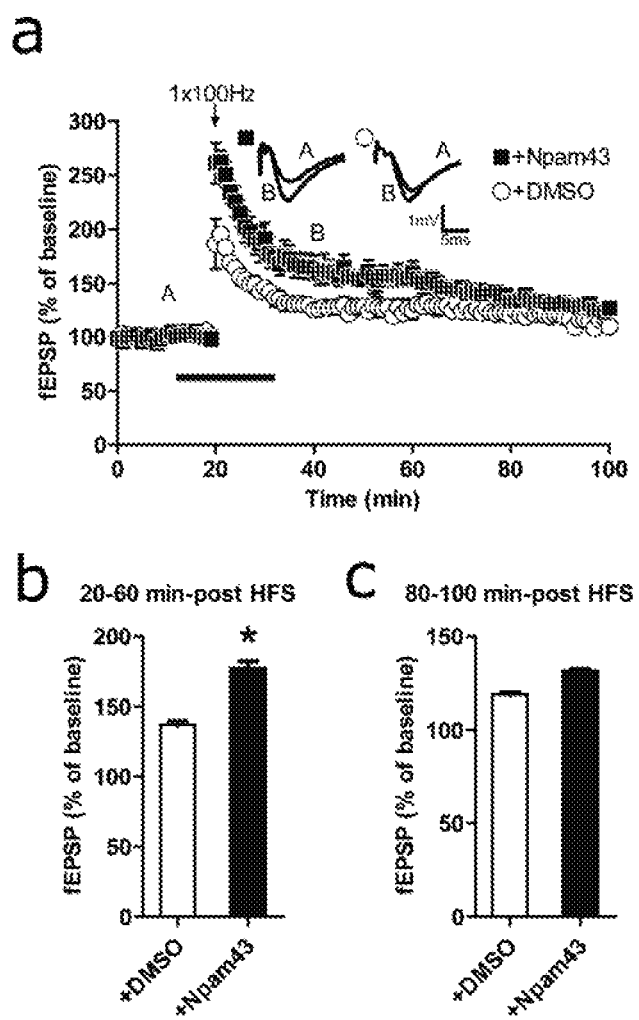

6.1 Both the GluN2A Component of Synaptic Transmission and Long-Term Potentiation (LTP) are Enhanced Electrophysiological recordings were performed to directly assay the effects of Npam43 on NMDAR currents in brain hippocampal slices, the inventors pharmacologically isolated GluN2A and GluN2B components of synaptic transmission in the presence of GluN2A or GluN2B antagonists (NVP-AAM007 (NVP), 0.2 μM; or ifenprodril, (IF) 3 μM). FIG. 18 demonstrates that Npam43 selectively potentiated the GluN2A component of NMDAR currents and no effects on the GluN2B NMDARs in mouse hippocampal slices. As activation of GluN2A has been shown to facilitate synaptic plasticity, electrophysiological recordings were also conducted to demonstrate that potentiation of GluN2A can facilitate long-term potentiation (LTP) and thus help to promote synaptic strength. FIG. 19 shows that Npam43 can facilitate the induction of LTP in mouse hippocampal slices.

Figure 20:
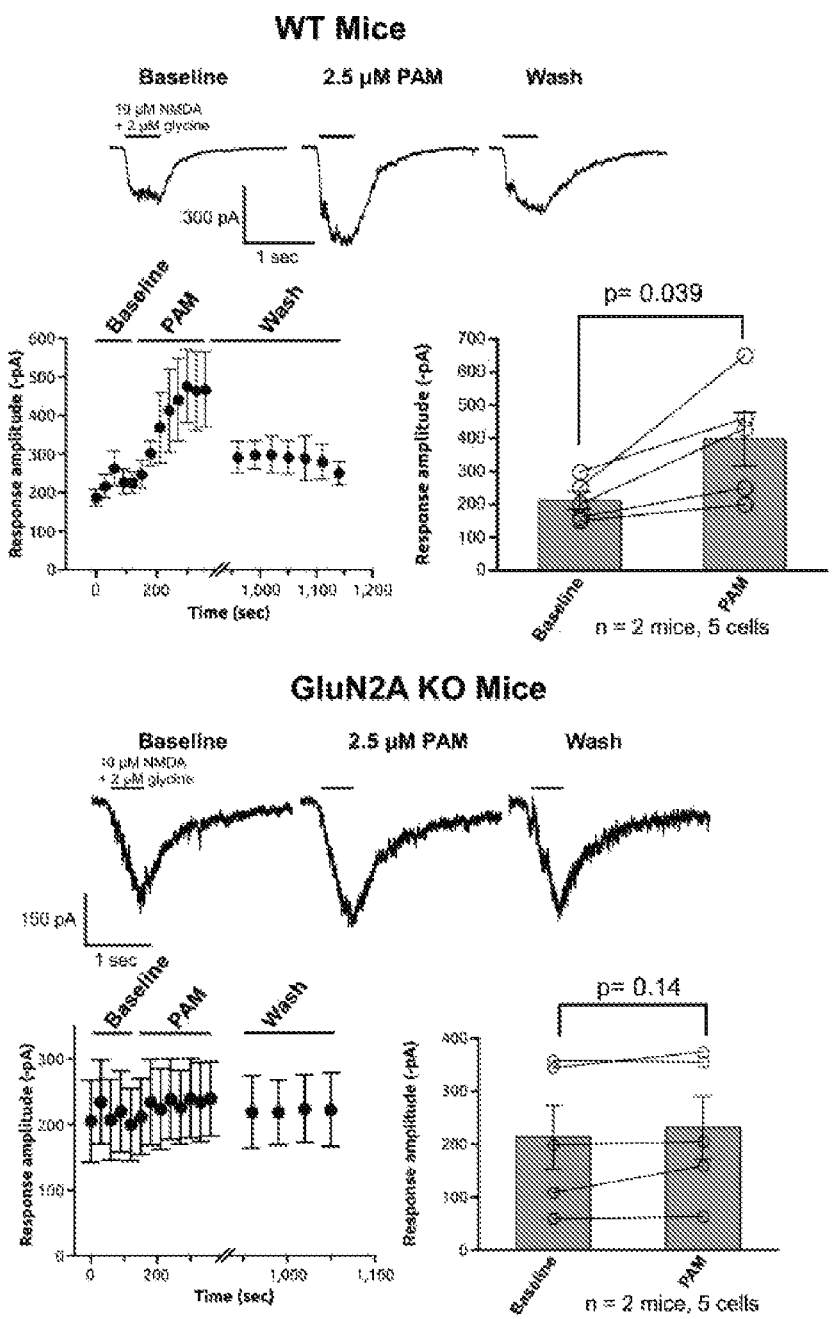

6.2 Potentiation Effect of Npam43 is on GluN2A NMDARs Demonstrated by Cortical Slices from Knockout (KO) GluN2A Mice To directly test the selectivity of Npam43 on synaptic activated NMDARs, recordings were performed in slices from GluN2A knockout (KO) mice as well as wild-type (WT) mice. FIG. 20 shows that in WT mice, a clear potentiation of NMDAR EPSC was observed when Npam43 was applied to brain slices. In GluN2A KO mice there was a no effect of Npam43 application on NMDAR EPSC suggesting its potentiation effect is attributed to GluN2A NMDARs.

6.3 Npam43 Increased pCREB Levels in Hippocampal Slices

Figure 21:
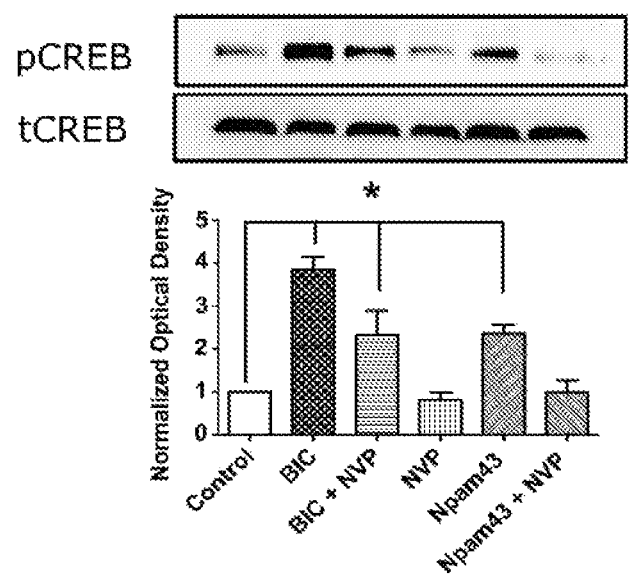
FIG. 21 Npam43 increased pCREB levels in hippocampal slices acutely prepared from mature rats.

Immunocytochemical analysis of CREB phosphorylation (pCREB) on Serine 133 at basal levels in hippocampal slices treated with bicuculline (BiC; 10 μM; 30 min exposure) or Npam43 (10 μM; 30 min exposure) in the presence and absence of NVP-AAM077 (0.2 μM) as shown in FIG. 21. Stimulation with BiC of neurons increased pCREB levels and this effect was reduced by b NVP-AAM007 (0.2 μM). Treatment with Npam43 (10 μM) significantly enhanced pCREB levels which was completely blocked in the presence of NVP-AAM077 (0.2 μM) as shown in FIG. 21.

Example 7 Pharmacological Profiling of Npam43

Npam43 Crosses the Brain-Blood Barrier Following IV-Injection in Mature Rats

Figure 22:
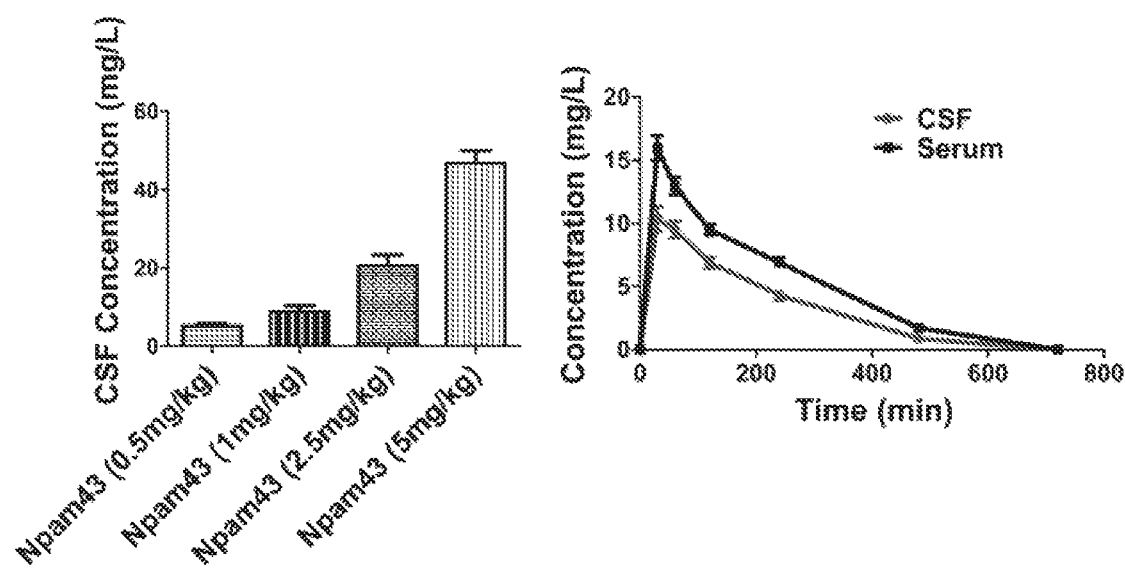
FIG. 22 Npam43 crosses the brain-blood barrier following N-injection in mature rats FIG. 23 Npam43 enhances pCREB levels in hippocampal tissue and cortical tissues following IV-injection in mature rats.

An in-vivo pharmacological profile of Npam43 was evaluated using Sprague Dawley mature (~300 g) rats. Npam43 was injected intravenously (i.v) at different doses ranging from 0.5-5 mg/kg and cerebrospinal fluid (CSF) and serum samples were extracted and analyzed using a high performance liquid chromatography electrochemical detection assay (HPLC-ECD). The pharmacokinetic analysis of Npam43 following intravenous administration demonstrated that it was effective at penetrating the blood-brain-barrier (BBB) and had a moderate metabolic stability in the CSF and serum as shown in FIG. 22. A linear relationship between the dose injected and the final concentration in the CSF was observed 1 h after injection. The half-life of Npam43 was estimated as 2.95±0.6 h in the CSF which was similar to the decay in serum as shown in FIG. 22.

Example 8 In-Vivo Efficacy of Npam43

8.1 Npam43 Enhances pCREB Levels in Hippocampal Tissue and Cortical Tissues.

Figure 23:
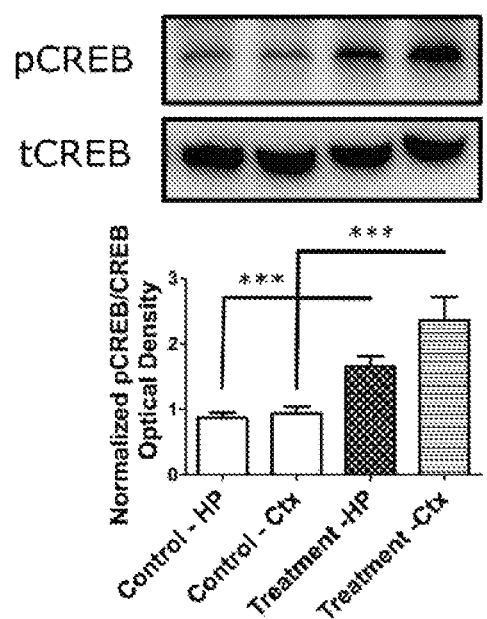

Hippocampal and cortical brain sections were harvested 1 h post-treatment via i.v. injection of Npam43 (1 mg/kg) and samples were probed for pCREB and tCREB levels via immunoblotting as shown in FIG. 23. Consistent with in-vitro assays, pCREB levels were elevated.

8.2 Reduction of Neuronal Damage after Ischemic Brain Insult

Figure 24:
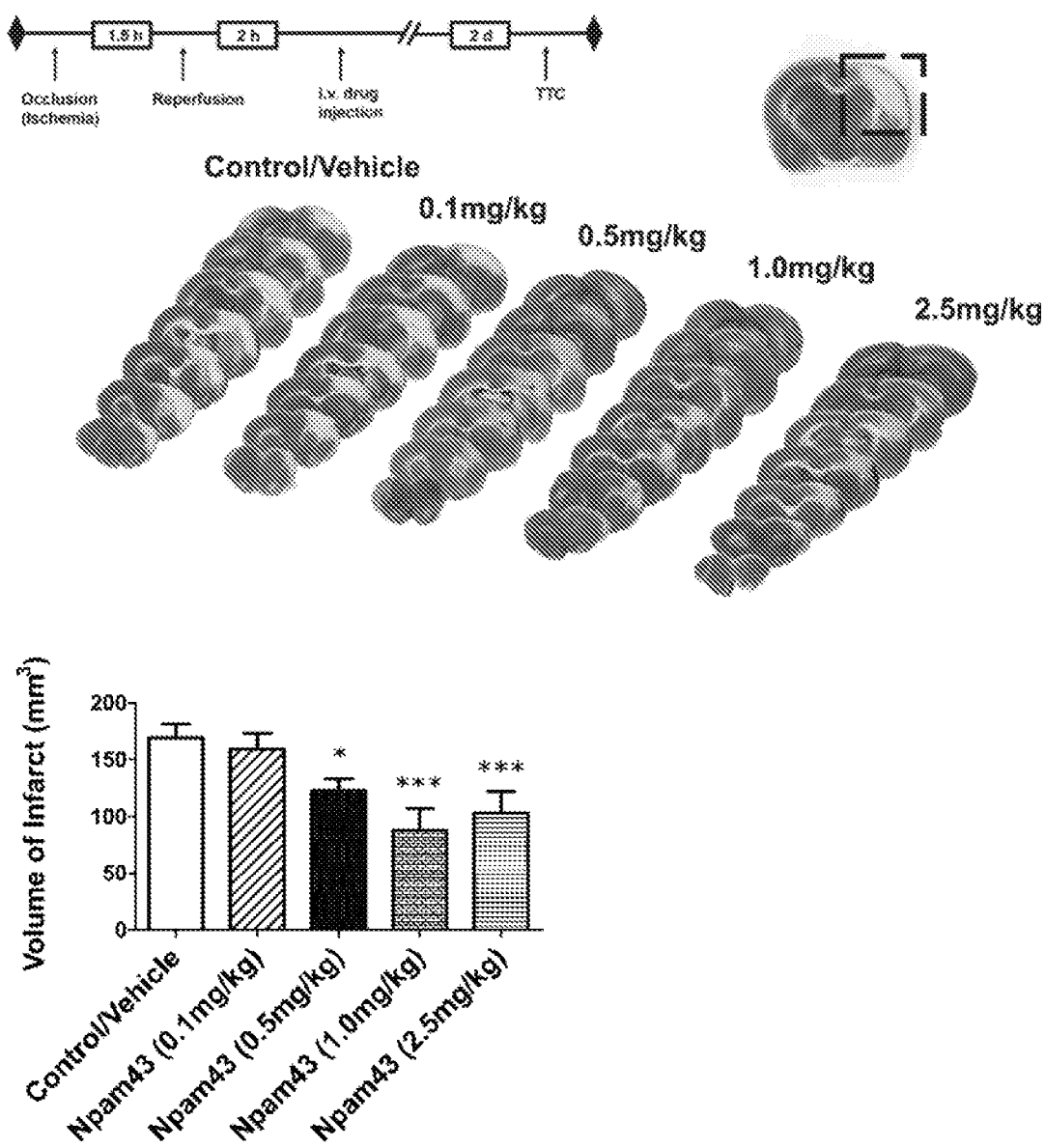
FIG. 24 Npam43 reduces the infract volume of ischemic brain of mice in-vivo.
Figure 25:
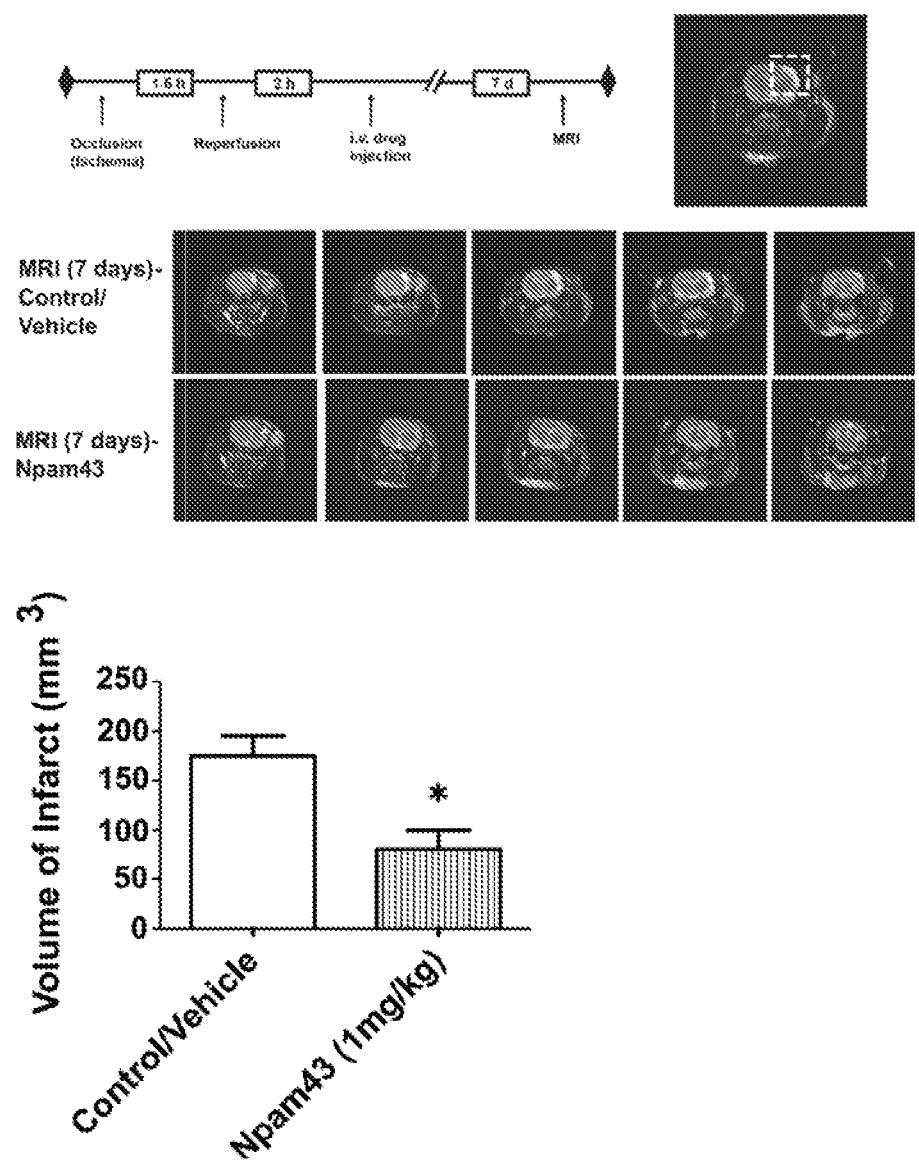
FIG. 25 Npam43 reduces post-stroke infarct volume using a long-term evaluation point.

Infarct size can be used as a measure of post-ictus brain damage. FIGS. 24-25 show that treatment with Npam43 reduces infarct volume in a rat model of middle cerebral artery occlusion (MCAo) compared to treatment with vehicle/saline controls. FIG. 24 demonstrates a dose-dependent effect of Npam43 on infarct volume at 24 h post ischemia. FIG. 25 shows that Npam43 reduces infarct size using a long term evaluation point (7 days) with MRI scanning.

8.3 Improved Behavioral Performance Following Focal Ischemic Brain Insult

Figure 26:
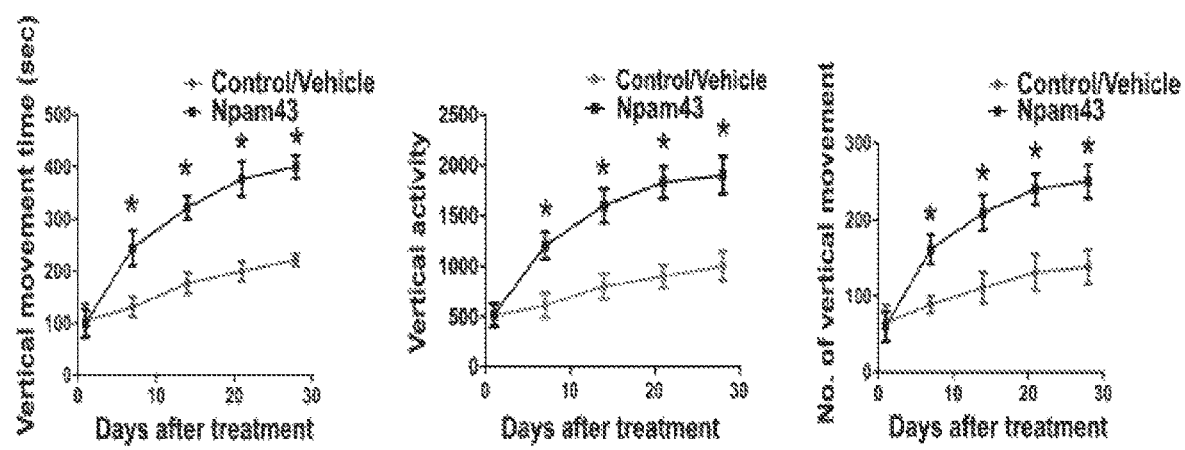
FIG. 26 Post-stoke treatment with Npam43 improves behavioral performance in vivo 28 days after stroke onset.

Neurobehavioral assays were performed to assess functional recovery of neurons post-stroke. FIG. 26 demonstrates that Npam43-treated rats show increased post-stroke locomotory behavior in comparison to untreated control rats 28 days after stroke onset.

The invention claimed is:

1. A method for treating a disorder or condition caused by or related to N-methyl-D-aspartate receptor (NMDAR) dysfunction in a subject in need thereof, the method comprising administering to said subject a compound or a pharmaceutically acceptable salt thereof, wherein the compound is selected from the group consisting of:

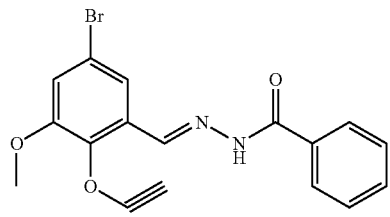

Npam01C (E)-N'-(5-bromo-2-(ethynyloxy)-3-methoxybenzylidene)benzohydrazide

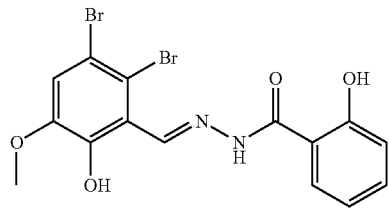

Npam02C (E)-N'-(2,3-dibromo-6-hydroxy-5-methoxybenzylidene)-2-hydroxybenzohydrazide

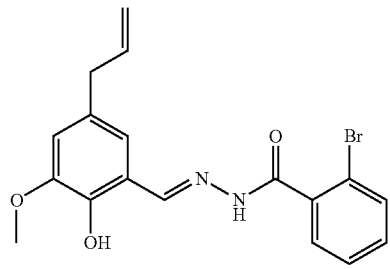

Npam03

(E)-N'-(5-allyl-2-hydroxy-3-methoxybenzylidene)-2-bromobenzohydrazide

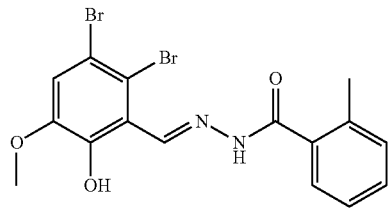

Npam04C (E)-N'-(2,3-dibromo-5-ethoxy-6-hydroxybenzylidene)-2-methylbenzohydrazide -continued

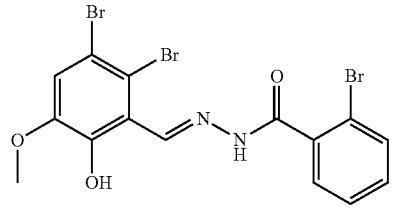

Npam05

(E)-2-bromo-N'-(2,3-dibromo-6-hydroxy-5-methoxybenzylidene)benzohydrazide

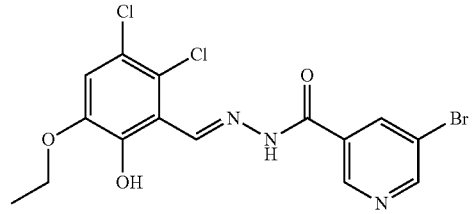

Npam06

(E)-5-bromo-N'-(2,3-dichloro-5-ethoxy-6-hydroxybenzylidene)nicotinohydrazide

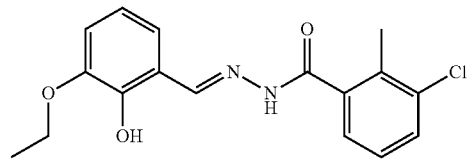

Npam07

(E)-3-chloro-N'-(3-ethoxy-2-hydroxybenzylidene)-2-methylbenzohydrazide

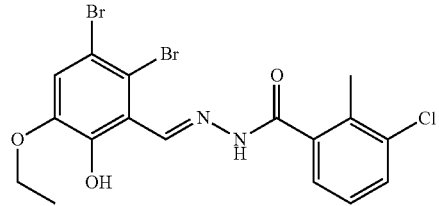

Npam10

3-chloro-N'-[(1E)-(2,3-dibromo-5-ethoxy-6-hydroxyphenyl)methylidene]-2-methylbenzohydrazide

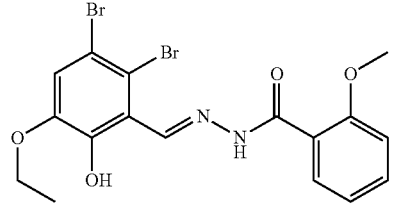

Npam12

(E)-N'-(2,3-dibromo-5-ethoxy-6-hydroxybenzylidene)-2-methoxybenzohydrazide

87
-continued

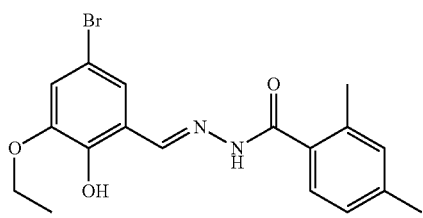

(E)-N′-(5-bromo-3-ethoxy-2-hydroxybenzylidene)-2,3-dimethylbenzohydrazide

Npam15

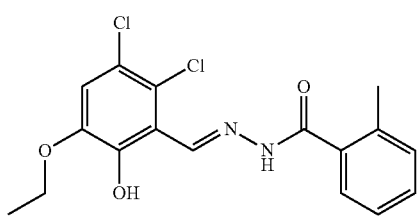

(E)-N′-(2,3-dichloro-5-ethoxy-6-hydroxybenzylidene)-2-methylbenzohydrazide

Npam17

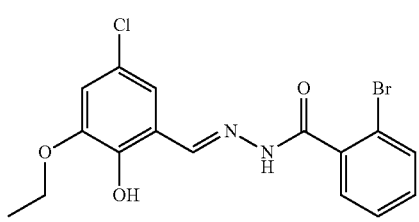

(E)-2-bromo-N′-(5-chloro-3-ethoxy-2-hydroxybenzylidene)benzohydrazide

Npam18

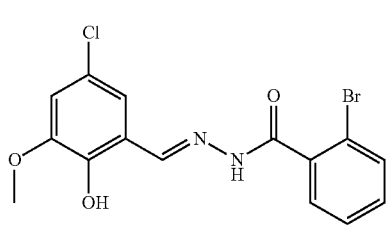

(E)-2-bromo-N′-(5-chloro-2-hydroxy-3-methoxybenzylidene)benzohydrazide

Npam20

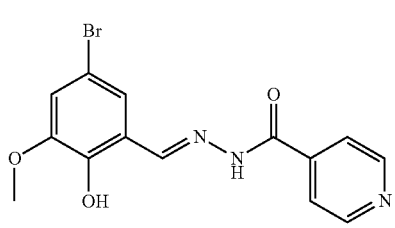

N′-[(1E)-(5-bromo-3-ethoxy-2-hydroxyphenyl)methylidene]pyridine-4-carbohydrazide Npam28

88
-continued

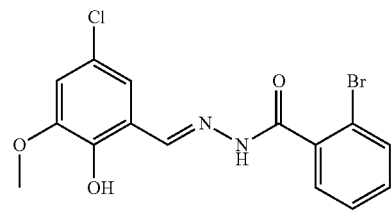

(E)-2-bromo-N′-(5-chloro-2-hydroxy-3-methoxybenzylidene)benzohydrazide

Npam29

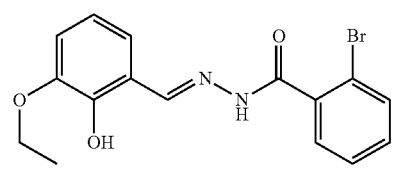

2-bromo-N′-[(1E)-(3-ethoxy-2-hydroxyphenyl)methylidene]benzohydrazide

Npam31

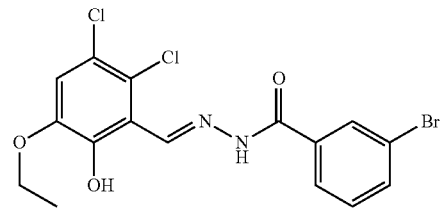

(E)-3-bromo-N′-(2,3-dichloro-5-ethoxy-6-hyrdoxybenzylidene)benzohydrazide

Npam32

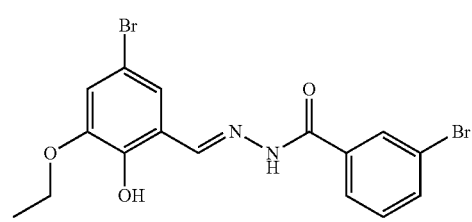

(E)-3-bromo-N′-(5-bromo-3-ethoxy-2-hyrdoxybenzylidene)benzohydrazide

Npam38

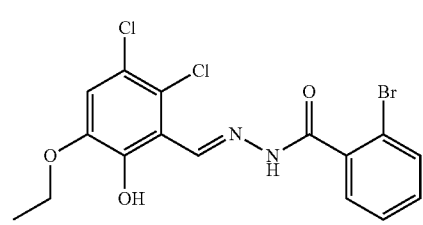

(E)-2-bromo-N′-(2,3-dichloro-5-ethoxy-6-hyrdoxybenzylidene)benzohydrazide

Npam43

Npam44

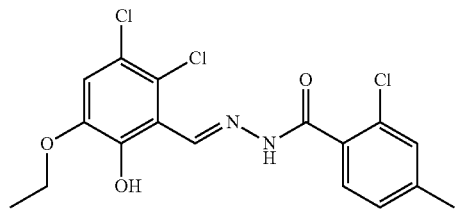

(E)-2-chloro-N'-(2,3-dichloro-5-ethoxy-6-
hyrdoxybenzylidene)-4-methylbenzohydrazide Npam51

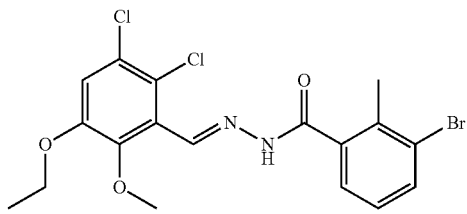

3-bromo-N'-[(1E)-(2,3-dichloro-5-ethoxy-6-
methoxyphenyl)methylidene]-2-methylbenzohydrazide Npam46

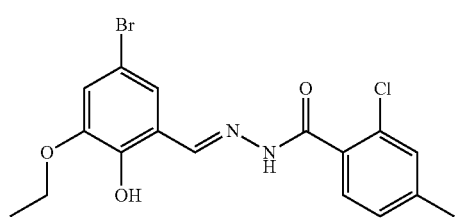

(E)-N'-(5-bromo-3-ethoxy-2-hyrdoxybenzylidene)-
2-chloro-4-methylbenzohydrazide

Npam52

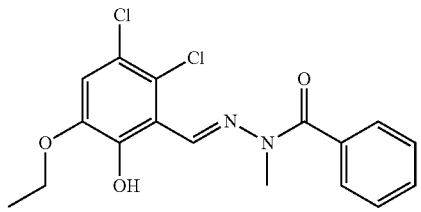

N'-[(1E)-(2,3-dichloro-5-ethoxy-6-
hydroxyphenyl)methylidene]-N-methylbenzohydrazide Npam48

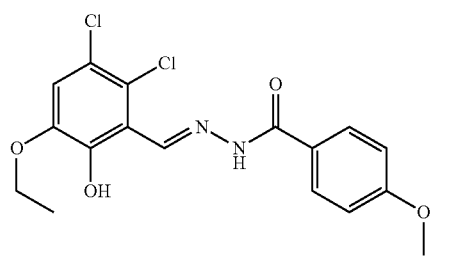

(E)-N'-(2,3-dichloro-5-ethoxy-6-
hyrdoxybenzylidene)-4-methoxybenzohydrazide

Npam53

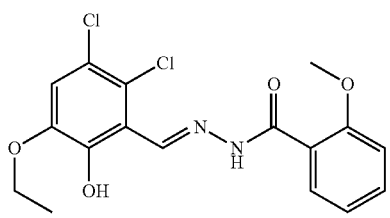

(E)-N'-(2,3-dichloro-5-ethoxy-6-
hydroxybenzlidene)-2-methoxybenzohydrazide

Npam49

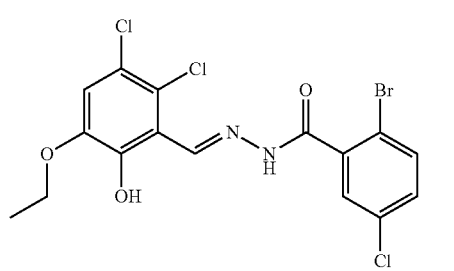

2-bromo-5-chloro-N'-[(1E)-(2,3-dichloro-5-ethoxy-6-
hyrdoxyphenyl)benzohydrazide Npam54

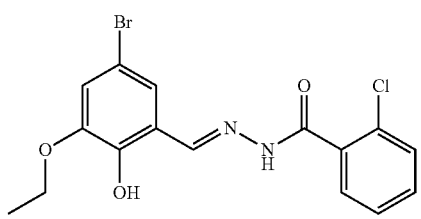

N'-[(E1)-(5-bromo-3-ethoxy-2-
hydroxyphenyl)methylidene]-2-chlorobenzohydrazide

Npam50

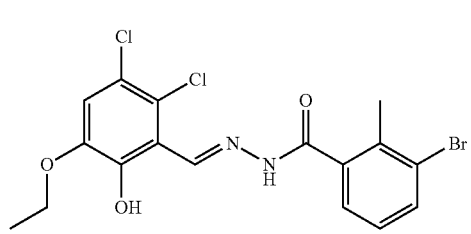

3-bromo-N'-[(1E)-(2,3-dichloro-5-ethoxy-6-
hyrdoxyphenyl)methylidene]-2-methylbenzohydrazide Npam55

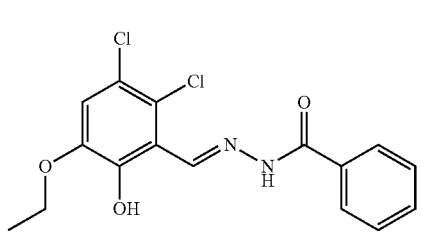

(E)-N'-(2,3-dichloro-5-ethoxy-6-
hydroxybenzylidene)benzohydrazide

-continued

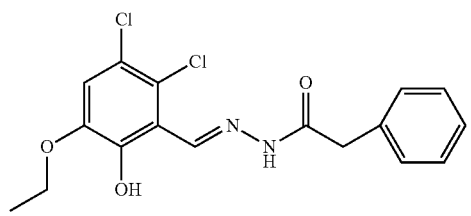

N'-[(E1)-(2,3-dichloro-5-ethoxy-6-hydroxyphenyl)methylidene]-2-phenylacetohydrazide

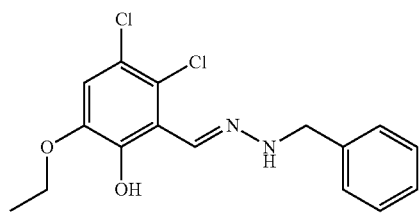

2-[(1E)-(2-benzylhydrazin-1-ylidene)methyl]-3,4-dichloro-6-ethoxyphenol

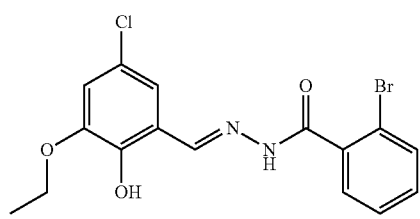

(E)-2-bromo-N'-(5-chloro-3-ethoxy-2-hydroxybenzylidene)benzohyrazide

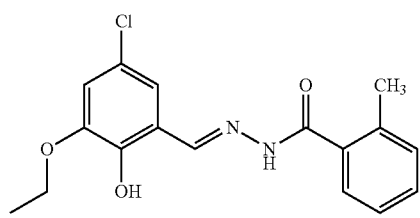

(E)-N'-(5-bromo-3-ethoxy-2-hydroxybenzylidene)-2-methylbenzohydrazide

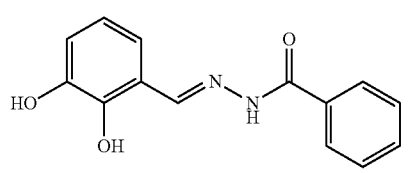

(E)-N'-(2,3-dihydroxybenzylidene)benzohyrazide

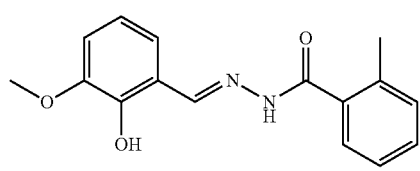

(E)-N'-(2-hydroxy-3-methoxybenzylidene)-2-methylbenzohyrazide

-continued

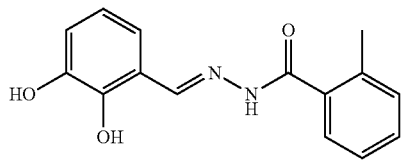

(E)-N'-(2,3-dihydroxybenzylidene)-2-methylbenzohyrazide

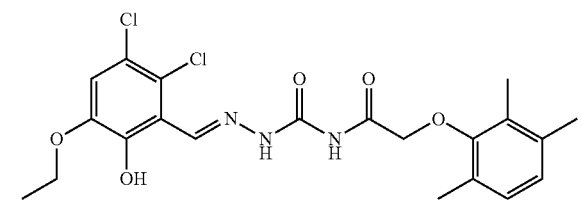

(E)-2-(2,3-dichloro-5-ethoxy-6-hyrdoxybenzylidene)-N-(2-(2,3,6-trimethylphenoxy)acetyl)hydrazinecarboxamide

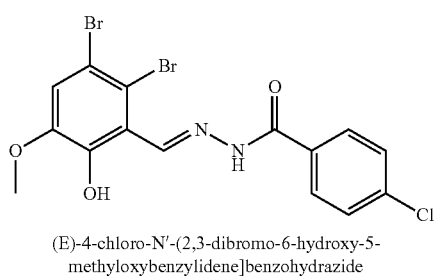

(E)-4-chloro-N'-(2,3-dibromo-6-hydroxy-5-methyloxybenzylidene]benzohydrazide

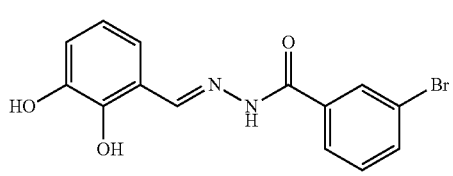

(E)-3-bromo-N'-(2,3-dihydroxybenzylidene]benzohydrazide

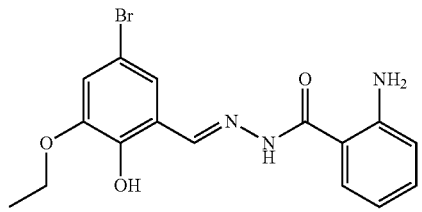

(E)-2-amino-N'-(5-bromo-3-ethoxy-2-hydroxybenzylidene]benzohydrazide

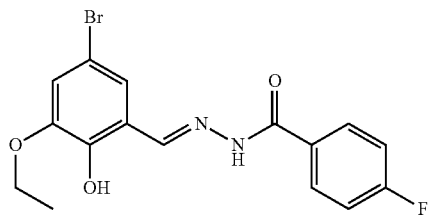

(E)-N'-(5-bromo-3-ethoxy-2-hydroxybenzylidene]-4-fluorobenzohydrazide

Npam23

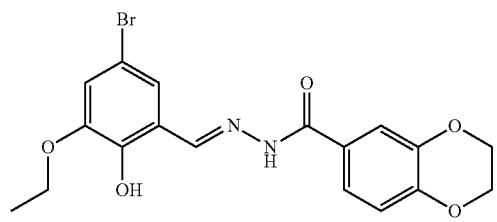

(E)-N'-(5-bromo-3-ethoxy-2-hyrdoxybenzylidene)-2,3
-dihydrobenzo[b][1,4]dioxine-6-carbohydrazide Npam24

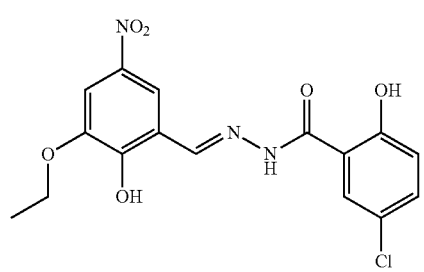

(E)-5-chloro-N'-(3-ethoxy-2-hydroxy-5-
nitrobenzylidene]2-hydroxybenzohydrazide

Npam25

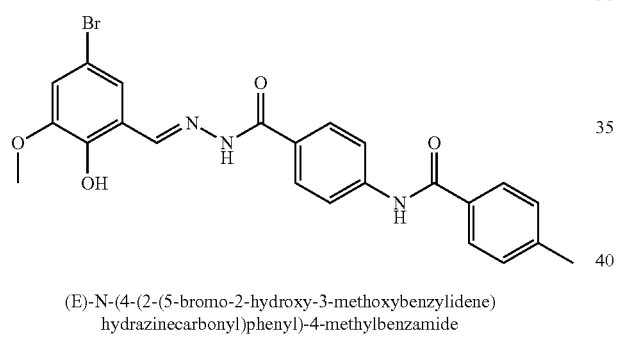

(E)-N-(4-(2-(5-bromo-2-hydroxy-3-methoxybenzylidene)
hydrazinecarbonyl)phenyl)-4-methylbenzamide Npam26

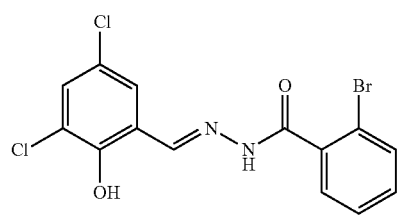

(E)-2-bromo-N'-(3,5-dichloro-2-
hydroxybenzylidene)benzohydrazide

Npam27

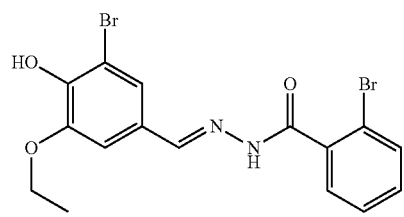

(E)-2-bromo-N'-(3-bromo-5-ethoxy-4-
hydroxybenzylidene)benzohydrazide

Npam30

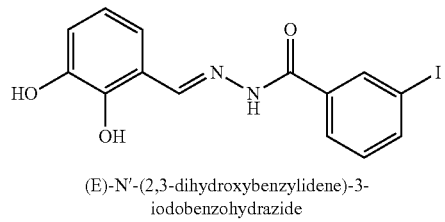

(E)-N'-(2,3-dihydroxybenzylidene)-3-
iodobenzohydrazide

Npam31

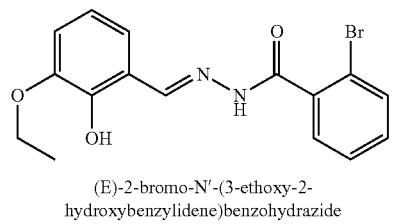

(E)-2-bromo-N'-(3-ethoxy-2-
hydroxybenzylidene)benzohydrazide

Npam34

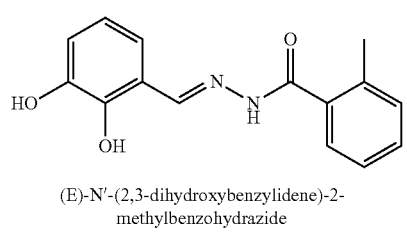

(E)-N'-(2,3-dihydroxybenzylidene)-2-
methylbenzohydrazide

Npam35

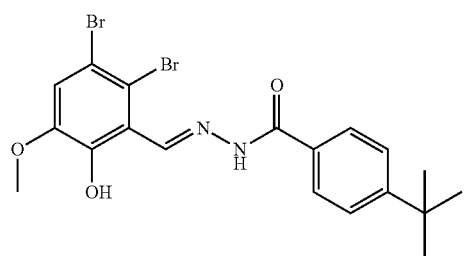

(E)-4-(tert-butyl)-N'-(2,3-dibromo-6-hydroxy-5-
methoxybenzylidene)benzohydrazide Npam36

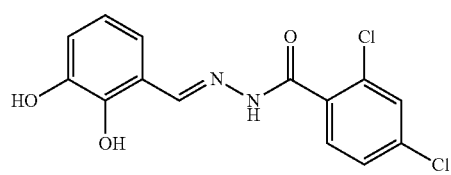

(E)-2,4-dichloro-N'-(2,3-
dihydroxybenzylidene)benzohydrazide

Npam37

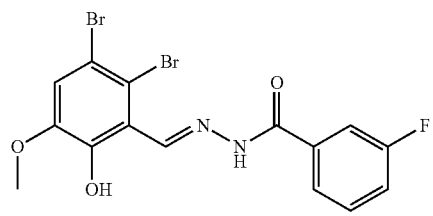

(E)-N'-(2,3-dibromo-6-hyrdoxy-5-
methoxybenzylidene)-3-fluorobenzohydrazide

Npam39

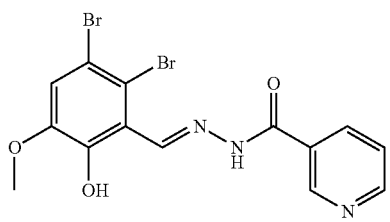

(E)-N'-(2,3-dibromo-6-hydroxy-5-methoxybenzylidene)nicotinohydrazide

Npam40

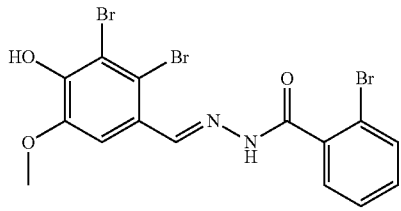

(E)-2-bromo-N'-(2,3-dibromo-4-hydroxy-5-methoxybenzylidene)benzohydrazide

Npam42

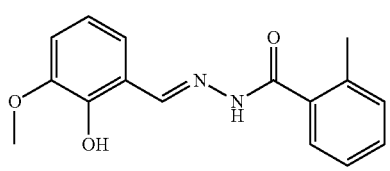

(E)-N'-(2-hydroxy-3-methoxybenzylidene)-2-methylbenzohydrazide

Npam45

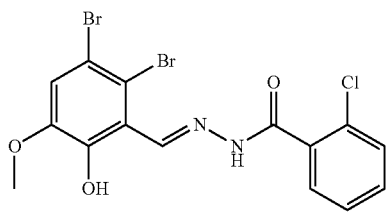

(E)-2-chloro-N'-(2,3-dibromo-6-hydroxy-5-methoxybenzylidene)benzohydrazide

Npam47

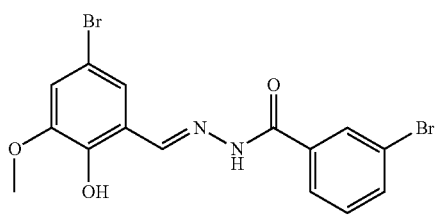

(E)-3-bromo-N'-(5-bromo-2-hydroxy-3-methoxybenzylidene)benzohydrazide

Npam58

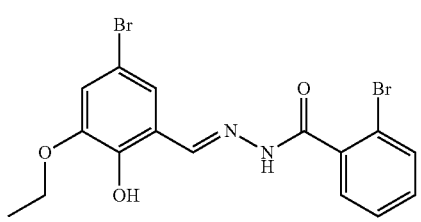

(E)-2-bromo-N'-(5-bromo-2-ethoxy-2-hydroxybenzylidene)benzohydrazide

Npam59

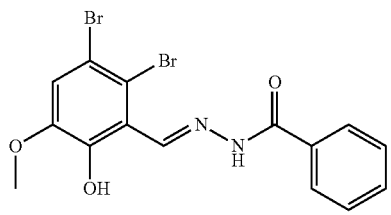

(E)-N'-(2,3-dibromo-6-hydroxy-5-methoxybenzylidene)benzohydrazide

Npam64

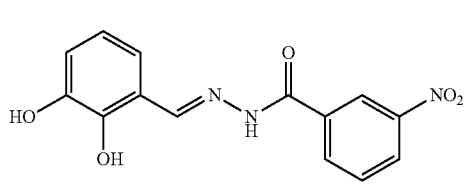

(E)-N'-(2,3-dihydroxybenzylidene)-3-nitrobenzohydrazide

Npam65

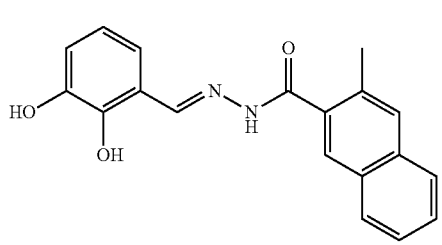

(E)-N'-(2,3-dihydroxybenzylidene)-3-methyl-2-naphthohydrazide

Npam66

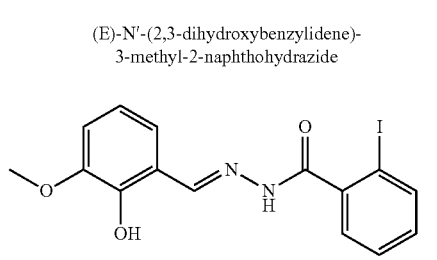

(E)-N'-(2-hydroxy-3-methoxybenzylidene)-2-iodobenzohydrazide

Npam68

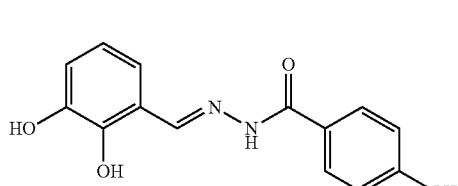

(E)-N'-(2,3-dihydroxybenzylidene)-4-hydroxybenzohydrazide

Npam69

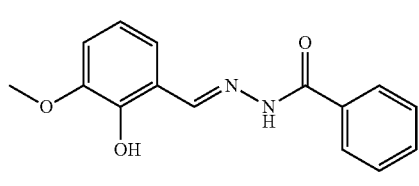

(E)-N'-(2-hydroxy-3-methoxybenzylidene)benzohydrazide

-continued

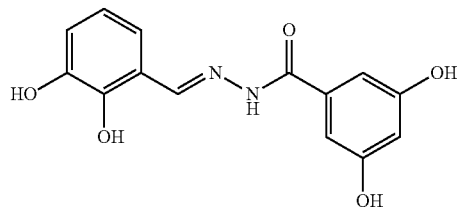

(E)-N'-(2,3-dihydroxybenzylidene)-
3,5-dihydroxybenzohydrazide

Npam70

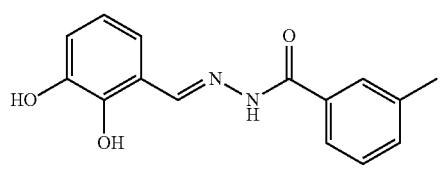

(E)-N'-(2,3-dihydroxybenzylidene)-
3-methylbenzohydrazide

Npam71

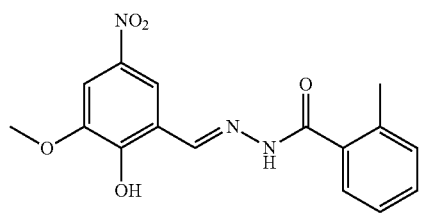

(E)-N'-(2-hydroxy-3-methoxy-5-nitrobenzylidene)-
2-methylbenzohydrazide

Npam72

-continued

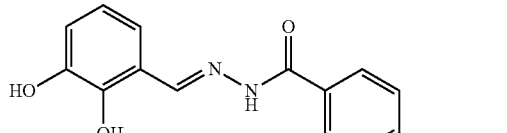

(E)-4-bromo-N'-(2,3-dihydroxybenzylidene)-
benzohydrazide

Npam73

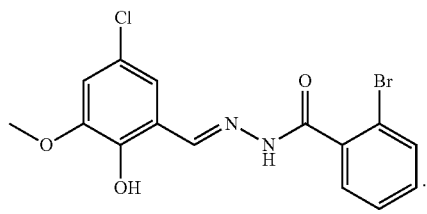

(E)-2-bromo-N'-(5-chloro-2-hydroxy-3-
ethoxybenzylidene)benzohydrazide

Npam75

2. The method of claim 1, wherein the compound is an NMDAR allosteric modulator.

3. The method of claim 2, wherein the compound is a selective GluN2A-containing NMDAR positive modulator.

4. The method of claim 2, wherein the disorder or condition is a neurological disorder associated with excitotoxicity.

5. The method of claim 2, wherein the disorder or condition is selected from the group consisting of impairments in learning and memory, migraine, epilepsy, Alzheimer's disease, Huntington's disease, Parkinson's disease, brain trauma, acute brain insults, schizophrenia, neuropathic pain, depression, and drug addiction.

6. The method of claim 2, wherein the disorder or condition is stroke.

\* \* \* \* \*